United States Patent
Wang et al.

(10) Patent No.: US 11,168,357 B2
(45) Date of Patent: Nov. 9, 2021

(54) OMEGA AMPLIFICATION

(71) Applicant: Atila Biosystems, Inc., Palo Alto, CA (US)

(72) Inventors: Youxiang Wang, Palo Alto, CA (US); Xin Chen, San Jose, CA (US); Rong Wang, Mountain View, CA (US); Zhijie Yang, Palo Alto, CA (US); Yu Zhao, Mountain View, CA (US)

(73) Assignee: Atila Biosystems, Inc., Palo Alto, CA (US)

(*) Notice: Subject to any disclaimer, the term of this patent is extended or adjusted under 35 U.S.C. 154(b) by 226 days.

(21) Appl. No.: 16/303,647

(22) PCT Filed: May 24, 2017

(86) PCT No.: PCT/US2017/034276
§ 371 (c)(1),
(2) Date: Nov. 20, 2018

(87) PCT Pub. No.: WO2017/205510
PCT Pub. Date: Nov. 30, 2017

(65) Prior Publication Data
US 2019/0203271 A1 Jul. 4, 2019

Related U.S. Application Data

(60) Provisional application No. 62/340,997, filed on May 24, 2016.

(51) Int. Cl.
| | | |
|---|---|---|
| C12Q 1/6818 | (2018.01) | |
| C12Q 1/6844 | (2018.01) | |
| C12Q 1/68 | (2018.01) | |
| C12Q 1/6806 | (2018.01) | |
| C12Q 1/6853 | (2018.01) | |
| C12Q 1/686 | (2018.01) | |

(52) U.S. Cl.
CPC ............ *C12Q 1/6818* (2013.01); *C12Q 1/68* (2013.01); *C12Q 1/6806* (2013.01); *C12Q 1/686* (2013.01); *C12Q 1/6846* (2013.01); *C12Q 1/6853* (2013.01); *C12N 2310/16* (2013.01); *C12Q 2525/205* (2013.01)

(58) Field of Classification Search
CPC ...... C12Q 1/6818; C12Q 1/68; C12Q 1/6806; C12Q 1/6853; C12Q 1/686; C12Q 1/6846; C12Q 2525/205; C12Q 1/6823; C12Q 1/6844; C12N 2310/16
See application file for complete search history.

(56) References Cited

U.S. PATENT DOCUMENTS

| 6,130,047 A | 10/2000 | Nadeau et al. |
|---|---|---|
| 2011/0136118 A1 | 6/2011 | Kreader et al. |
| 2012/0276538 A1 | 11/2012 | Nadeau |
| 2014/0057256 A1 | 2/2014 | Shim et al. |
| 2014/0072967 A1 | 3/2014 | Kolpashchikov et al. |
| 2014/0255928 A1 | 9/2014 | Belousov et al. |
| 2014/0295447 A1* | 10/2014 | Hayashizaki .......... C07H 21/04 435/6.12 |
| 2016/0108468 A1 | 4/2016 | Kankia |

FOREIGN PATENT DOCUMENTS

| CN | 104962607 A | 10/2015 |
|---|---|---|
| EP | 1087020 A2 | 3/2001 |
| WO | WO 2015/019247 A1 | 2/2015 |
| WO | WO-2018114674 A1 | 6/2018 |

OTHER PUBLICATIONS

Notami et al., Nucleic Acids Res., 28:e63, i-vii (Year: 2000).*
International Search Report and Written Opinion received for PCT Patent Application No. PCT/US2017/034276, dated Aug. 25, 2017, 11 pages.
Faltin et al. "Mediator Probe PCR: A Novel Approach for Detection of Real-Time PCR Based 1-3 on Label-Free Primary Probes and Standardized Secondary Universal Fluorogenic Reporters," Clinical Chemistry, Aug. 24, 2012 (Aug. 24, 2012), vol. 58, Iss. 11, pp. 1546-1556. (Entire document).
Extended European Search Report and Written Opinion received for PCT Patent Application No. PCT/US2017/034276, dated Apr. 9, 2020, 22 pages.
Huang et al., (2015). "Attomolar Detection of Proteins via Cascade Strand-Displacement Amplification and Polystyrene Nanoparticle Enhancement in Fluorescence Polarization Aptasensors," Analytical Chemistry, 87(16):8107-8114.
Kolpashchikov, (2008). "Split DNA Enzyme for Visual Single Nucleotide Polymorphism Typing," Journal of the American Chemical Society, 130(10):2934-2935.
Partial Supplementary European Search Report and Written Opinion received for PCT Patent Application No. PCT/US2017/034276, dated Mar. 12, 2019, 18 pages.
Walker et al., (1992). "Strand Displacement Amplification—An Isothermal, In Vitro DNA Amplification Technique," Nucleic Acids Research, 20(7):1691-1696.
Wang et al., (2011). "Homogeneous Label-Free Genotyping of Single Nucleotide Polymorphism Using Ligation-Mediated Strand Displacement Amplification with DNAzyme-Based Chemiluminescence Detection," Analytical Chemistry, 83(6):1883-1889.
Wang et al., (2015). "Multiple Endonuclease Restriction Real-Time Loop-Mediated Isothermal Amplification A Novel Analytically Rapid, Sensitive, Multiplex Loop-Mediated Isothermal Amplification Detection Technique," The Journal of Molecular Diagnostics, 17(4):392-401.

* cited by examiner

*Primary Examiner* — Cynthia B Wilder
(74) *Attorney, Agent, or Firm* — Morrison and Foerster LLP

(57) ABSTRACT

The present disclosure provides compositions, methods and kits for Omega amplification technologies. In addition, the present disclosure provides compositions, methods and kits for universal FQ probe and for G-quadruplex detection methods for use in isothermal amplification technologies.

17 Claims, 26 Drawing Sheets

Specification includes a Sequence Listing.

AATATGGGAACACAGGTACGTGTGGGAAGTACATTTTGGGAATAATGTAAT
                                                    HPV18-F3
TGATTGTAATGACTCTATGTGCAGTACCAGTGACGACACGGTATCCGCT
                              HPV18-F2
ACTCAGCTTGTTAAACAGCTACAGCACACCCCTCACCGTATTCCAGCA
                              HPV18-F1
CCGTGTCCGTGGGCACCGGCAAAGACCTACGGCCAGACGTCGGCTGCT
     HPV18-R1
ACACGACCTGGACACTGTGGACTCGCGGAGAAGCAGCATTGTGGACC
             HPV18-R2
TGTCAACCCACTTCTCGGGTGCAGTGCACCTACAGGCAACAACAAAAG
     HPV18-R3
ACGGAAACTCTGTAGTGGTAACACTACGCCCTATAATACATTTAAAAGGT

GACAGAAACAGTTTAAAAATGTTTACGGTACAGATTGCGAAAACATAGCG

ACCACTATAGAGA

FIG. 8

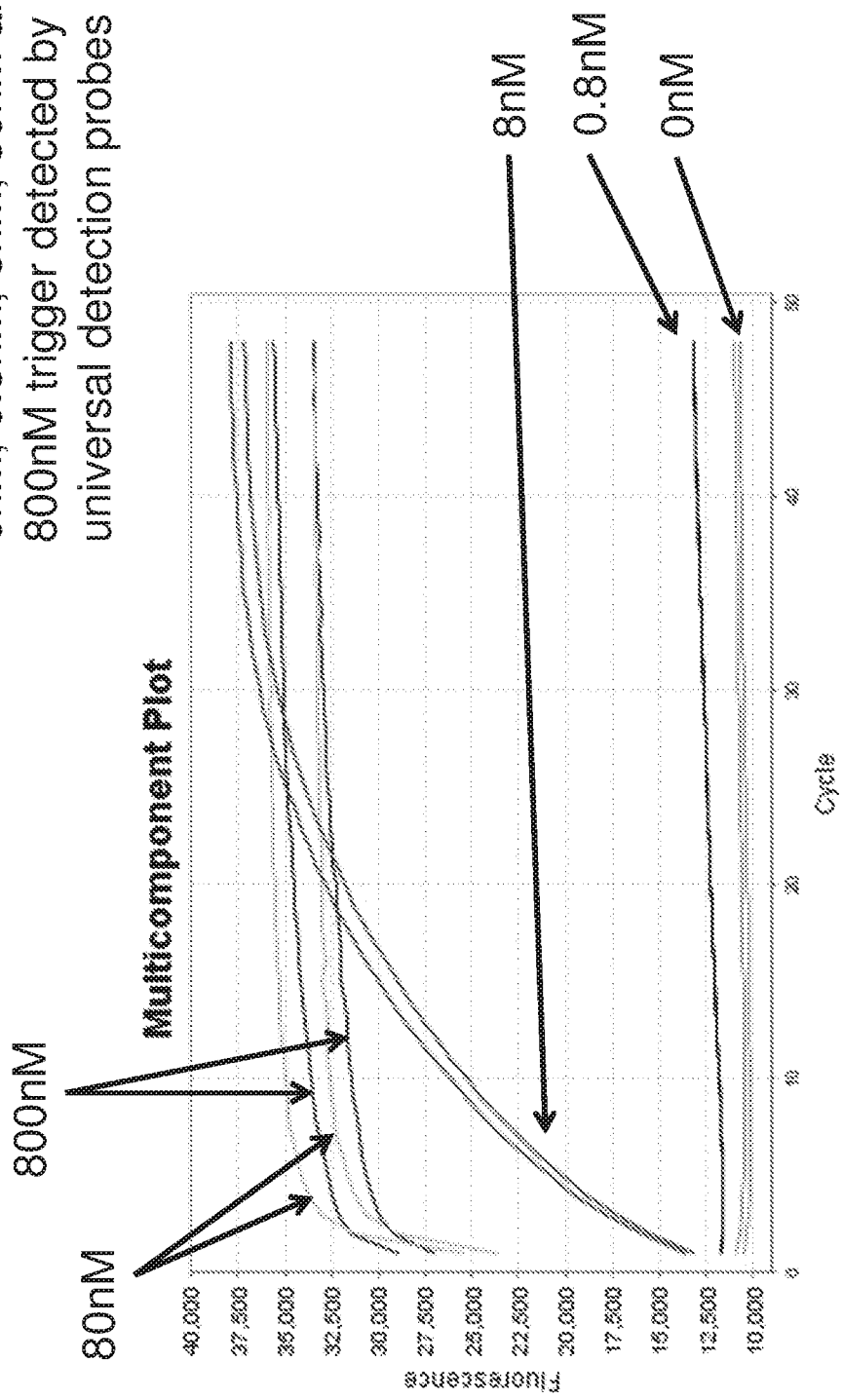

OMEGA AMPLIFICATION

CROSS REFERENCE TO RELATED APPLICATIONS

This application is a U.S. National Phase patent application under 35 U.S.C. § 371 of PCT/US2017/034276, filed May 24, 2017, which claims the benefit priority to expired provisional patent application 62/340,997, filed May 24, 2016, the disclosures of which are incorporated herein by reference in their entirety.

FIELD

The present disclosure relates generally to compositions and methods related to nucleic acid amplification technologies (NAATs). In particular, it relates to improvements in detection of nucleic acids amplified using NAATs with a preferred emphasis on foldback primer mediated isothermal amplification technologies.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 737962000100SEQLIST.txt, date recorded: Nov. 19, 2018 size: 20 KB).

BACKGROUND

A technique known as loop mediated isothermal amplification (LAMP) has become the focus of significant research and development in the diagnostics and testing industry due to advantages that LAMP has over prior technologies, such as PCR. LAMP is a robust technique that can he practiced in a single reaction tube with minimal processing of the nucleic acid. Further, LAMP is an isothermal amplification technology and therefore does not require expensive thermocyclers used for PCR. LAMP has been adapted for a number of applications, such as SNP detection. An exemplary LAMP-based SNP detection method is disclosed in U.S. Pat. No. 7,175,985, where even a single mismatch at the 5' end of one of the looping primers was sufficient to inhibit amplification (see, e.g., Example 1 of U.S. Pat. No. 7,175,985). This highlights the view in the art of the importance of the ability of the foldback primers to form a new, free 3' hydroxyl (OH) from which complementary strand synthesis can occur.

Since the development of LAMP, a number of related techniques and improvements have been developed. SMAP is similar to LAMP except that it is asymmetric. SMAP uses a single looping primer and a "folding" primer that folds back on itself rather than onto the template. SMAP can be combined with MutS for detection of nucleic acid polymorphisms in samples (see, e.g., WO2005/063977). GEAR is a variation on LAMP amplification where the two foldback primers fold back on downstream complementary sequences so that only three internal regions are needed. GEAR can also be included with loop acceleration primers so that flanking "kicker" acceleration primers are not needed. All of these NAATs are related because at least one of the primers (and typically two) has an additional region at its 5' terminus that folds back onto the replicated nucleic acid (template sequence), When the complementary strand is generated, this becomes a free 3' end in the complementary strand that folds back and allows further amplification to occur. This ability of the foldback primers to generate a new, free 3' OH from which further strand synthesis can occur is viewed as an important feature in these amplification reactions.

These foldback amplification technologies are more complicated than PCR, as each amplicon typically requires four primers (or six primers) with six (or even eight) regions of homology. This complicates multiplexing of these technologies due to the requirement for multiple primers for each reaction. Further, the use of strand displacing polymerases prohibits the use of hydrolysis probes (e.g., TAQMAN™), which rely upon the 5' to 3' exonuclease activity of the amplification polymerase. The concatenated products of foldback amplification technologies confound differentiation of multiple amplification targets on a gel. In one multiplexed assay, amplicons were selected with restriction sites that allow resolution of the concatenated products into products that can readily be separated and identified on a gel (H. Iseki et al. (2007)). However, this assay required additional processing steps. In another multiplex assay, duplexed probes were used which have a quencher in one strand and a fluorescent probe in the second strand. During amplification, the strands are displaced, allowing the fluorescent probe to fluoresce (Biosensors and Bioelectronics 30 (2011) 255-260). This process complicates manufacturing, as at least one of the probes requires a double stranded portion and specific fluorescent probes need to be designed for each detection reaction.

Thus, there is a need for additional technologies that improve detection of nucleic acids amplified using NAATs generally, and particularly for technologies that improve detection of fold back amplification technologies without requiring additional primers, regions of homology, or more complicated probes which necessitate synthesis of two strands.

SUMMARY

The disclosed invention provides methods of monitoring isothermal amplification of a target I)NA in real time through monitoring interaction between specific detection probe and universal detection probes or chemicals. The current inventions enable to detect multiple targets isothermal amplification in real time. The methods generally comprise providing a reaction mixture comprising a target nucleic acid, and a specific detection probe, and the universal detection probes. The signal generated through interaction between the specific detection probe and universal detection probe monitors the isothermal amplification of a target nucleic acid in real time. The specific detection probe comprises a specific probe sequence, which can be an arbitrary sequence, that is linked to the 5' of a target specific primer or probe. The specific probe sequence may also hybridize with a provided second oligonucleotide that is complementary to the specific probe sequences. The provided second oligonucleotide may be linked with the specific probe sequence through a linker covalently. The linker may or may not block polymerase extension. The universal detection probe (a universal fluorescent quencher (FQ) probe) comprises two oligonucleotide strands, wherein a first oligonucleotide strand comprises a quencher probe positioned at a 3' end and wherein a second oligonucleotide strand of the universal FQ probe comprises a fluorophore conjugated at a 5' end and is complementary to the first oligonucleotide stand at its 5' portion. Alternatively, the first oligonucleotide strand comprises a fluorophore probe positioned at a 3' end and wherein a second oligonucleotide strand of the universal FQ probe comprises a quencher conjugated at a 5' end and is complementary to the first oligonucleotide stand at its 5' portion. In some embodiments, the 3' portion of the second oligonucleotide stand contains a full sequence or part of the specific probe sequence or the specific probe complementary sequence. In some embodiments, a ratio of the amount of the second oligonucleotide strand to the amount of the first oligonucleotide strand that is added to the reaction mixture may be less than 1:1, A DNA polymerase may also be added to the reaction mixture. Fluorescence emitted by the reaction mixture including the specific probe and the FQ probe and the target DNA can be measured. In some embodiment, the universal detection probe may be single strand oligonucleotides, wherein the quencher and fluorophore may be labeled at 3' or 5' end or at middle of the oligonucleotides. In another embodiment, the universal detection probes comprises more than one set of oligonucleotides, wherein the specific detection probe triggers the sequential interaction amount the sets of oligonucleotides to generate detection signal. In another embodiment, the specific probe sequence may be used as a template to interact with the universal detection probes.

In the presence of strand displacing DNA polymerase, once the specific probe containing template-specific primer is involved in the amplification reaction, the complementary sequence of the specific probe sequence is generated. When a second oligo complementary to the specific probe sequence is already hybridized to the specific probe sequence, the second oligo will be displaced away from the specific probe. The synthesized or displaced sequence complementary to the specific probe sequence will interact with the universal FQ probe, generating detectable fluorescent signal. In another embodiment, the generated complementary sequence of the specific probe sequence during amplification will interact with universal detection probe to generate detection signal. Alternatively, the synthesized or displaced sequence complementary to the specific probe sequence contains certain structural features, such as G-quadruplex or other aptamer binding capabilities. Detection of the formation of such nucleic acids' structural features can reflect the proceedings of the target amplification reactions.

The interaction between the complementary sequence of the specific probe sequence and the universal FQ probe can be DNA polymerase independent, such as in the case of molecular beacon and Yin-yang probes. In this case, the hybridization of the complementary sequence of the specific probe sequence to the universal FQ probe causes separation or structural change between the fluorescent and quench moieties in the FQ probe, giving the fluorescent signal. The interaction between the complementary sequence of the specific probe sequence and the universal FQ probe can alternatively be DNA polymerase dependent. In this case, the newly synthesized/displaced complementary sequence of the specific probe sequence serves as a primer on the universal FQ probe and extends on the FQ probe as template, displacing the quench moiety away from the fluorescent moiety of the FQ probe and giving the fluorescent signal. In another case, the newly synthesized/displaced complementary sequence of the specific probe sequence serves as a template for the universal FQ probe and extends on the specific probe sequence to generate the fluorescent signal changes.

The interaction between the complementary sequence of the specific probe sequence or displaced sequence and the universal probe can be utilized to further amplify the signal. The newly synthesized complementary sequence of the specific probe sequence or displaced sequence can be subjected to other signal amplification reactions such as rolling cycle amplification (RCA), exponential amplification reaction (EXPAR), and FQ invader sequence amplification.

Another aspect of the present disclosure is the attachment of specific probe sequences to target-specific primers, such as FIP or BIP in loop-mediated isothermal amplification (LAMP) and related amplification technologies such as SMAP and GEAR technologies. In some embodiments, both the specific probe sequence labeled target-specific primer and the non-labeled target specific primer are included in the reaction mixture. The ratio of the amount of the specific probe sequence labeled target-specific primer and the amount of the non-labeled target specific primer may be adjusted depending on the amplification and detection applications needs.

LAMP (or SMAP and GEAR) technologies require that the 5' regions, especially the 5' terminal nucleotide, of the foldback primers (FIP and BIP) anneal by forming base pairs to the synthesized sequences when the primer is extended on the target template. When the complementary strand of such strand is synthesized, the 3' region can form base pairs with a region in the same strand, and the 3' terminal nucleotide can be used effectively as a primer to carry out amplification as specified by LAMP. Introduction of artificial sequences at the 5' region of FIP or BIP therefore will result in a 3' terminal region having a complementary artificial sequence extruding out and which does not anneal to the upstream sequences. This should prevent the newly synthesized 3' terminus from being used as a primer for strand extension.

Surprisingly, the introduction of extra artificial sequences to the 5' regions of FIP and BIP has only a minimum effect on amplification efficiency. The 5' region of the artificial sequence attached to the foldback primers is a distinguished feature as compared to LAMP, SMAP or GEAR technology. We termed this new technology the OMEGA amplification technology. The extruding sequence that is unique to OMEGA amplification technology allows introduction of additional sequences that can be used for detection (especially for multiplex reaction), further acceleration of the amplification reaction, and other uses.

Another aspect of the present disclosure is to improve foldback primer amplification (LAMP, GEAR, SMAP, OMEGA) speed and sensitivity. In one embodiment, more than one sets of kicker primer (forward kicker primer and reverse kicker primer) are used in the amplification reaction. In another embodiment, the kicker primer has additional sequence at 5'end and behavior as a foldback primer that can hybridize to the downstream of the same strand DNA molecule when the kick primer is extended during the amplification by DNA polymerase, In another embodiment, the additional sequence at 5' end of kick primer can be any artificial sequences that can accelerate or inhibit the amplification reaction. In another aspect, loop accelerate primer has additional sequence at 5' end that can hybridize to the downstream of the same strand DNA molecule when the loop accelerate primer is extended after foldback primer amplification initiated by DNA polymerase. In another aspect, the complementary of the loop accelerate primer can be used as primer to initiate additional reaction and amplification. In another aspect, the additional sequence at 5' end of the loop primer can be any artificial sequence that can accelerate or inhibit the amplification reaction. In another aspect, additional sequences can be added to the stem primers. The additional sequence can hybridize to the downstream sequences or any artificial sequences as long as they can help to speed up the amplification reactions. In another aspect, additional primer that is the same to folding sequence of FIB or BIP or the same as extruding sequence can be added into the reactions, In another aspect, the amplification reaction mixture can include both modified and unmodified primers mentioned previously. The ratios can be used to adjust the amplification reaction speed or sensitivity. For instance, the loop primers in the reaction mixture can include both with extra sequence at 5' end or without additional sequence at 5' end, The ratio of with additional sequence and without additional sequence can be adjusted depending on amplification and detection applications.

DESCRIPTION OF THE DRAWINGS

The patent or application file contains at least one drawing executed in color. Copies of this patent or patent application publication with color drawing(s) will be provided by the Office upon request and payment of the necessary fee. The following drawings form part of the present specification and are included to further demonstrate certain aspects of the present disclosure. The disclosure may be better understood by reference to one or more of these drawings in combination with the detailed description of specific embodiments presented herein.

FIG. 8 shows an exemplary primer design for HPV18 amplification and detection (SEQ ID NO: 86).

FIG. 23A shows an exemplary experiment result using universal detection probes in a real-time isothermal reaction based on the format as shown in FIG. 14. 0 nM (green), 0.8 nM (black), 8 nM (red), 80 nM (light blue) and 800 nM (dark blue) invader trigger was detected in a 25 ul reaction containing 0.1 µM spine sequence, 0.1 nM spine cover, 0.8 µM universal primer. The reaction was carried out at 60° C. for 48 minutes with FAM fluorescence measured at 60 second interval in an ABI StepOne Real-time PCR Instrument™.

DEFINITIONS

Figure 1A:
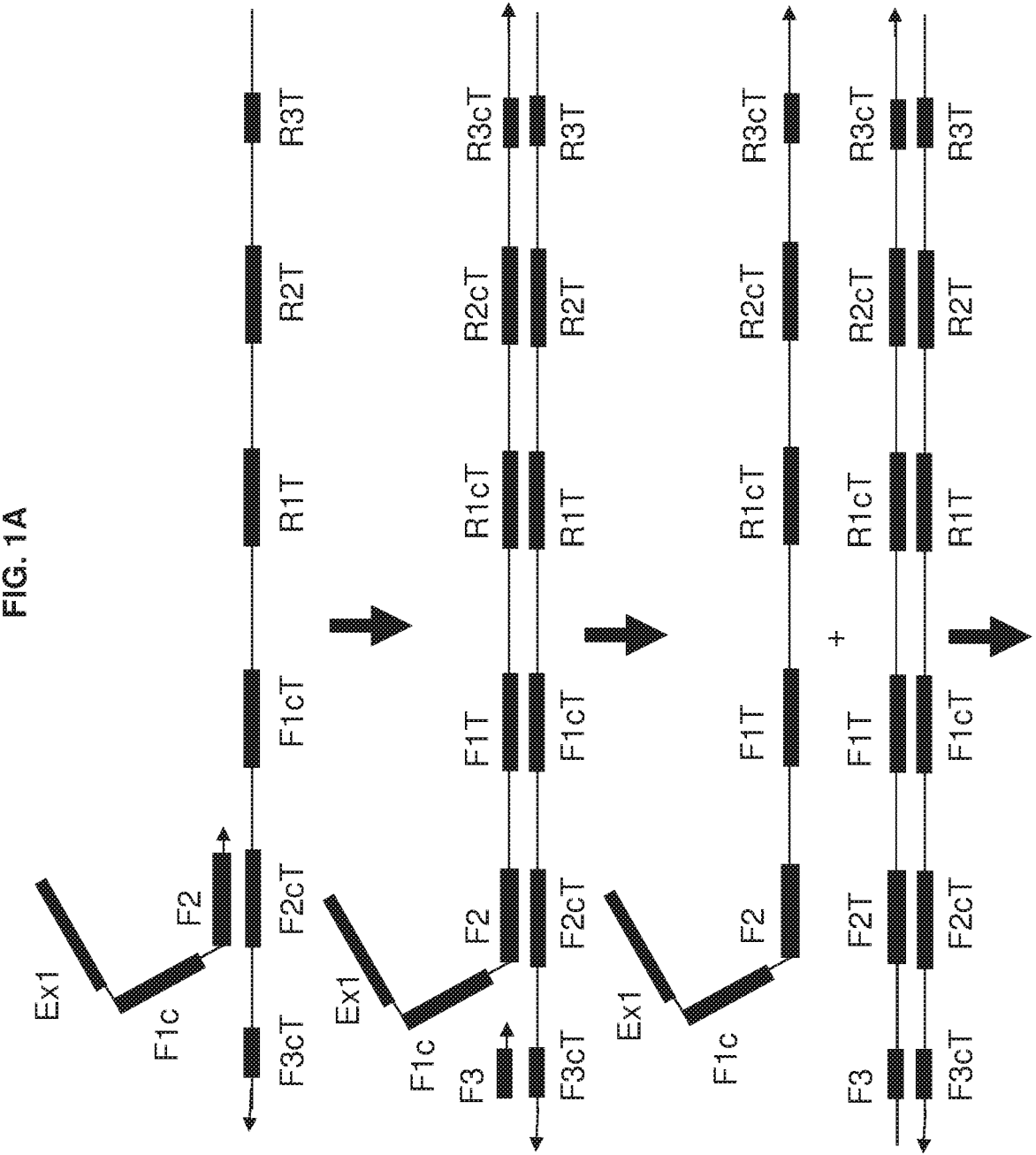
FIG. 1A and FIG. 1B show an exemplary implementation of omega amplification based upon a primer set of one extruding primer and one foldback primer.

As used herein, the terms "complementary" or "complementarity" are used in reference to polynucleotides (e.g., a sequence of nucleotides such as an oligonucleotide or a target nucleic acid) related by the base-pairing rules. For example, the sequence "A-G-T" is complementary to the sequence "T-C-A." Complementarity may he "partial," in which only some of the nucleic acids' bases are matched according to the base pairing rules, Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids.

Hybridization and the strength of hybridization (the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (see e.g., Anderson and Young, Quantitative Fitter Hybridization, in Nucleic Acid Hybridization (1985)). Other references include more sophisticated computations which take structural as well as sequence characteristics into account for the calculation of $T_m$.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

The term "oligonucleotide" encompasses a singular "oligonucleotide" as well as plural "oligonucleotides as used herein is defined as a molecule comprised of two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof. Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring, As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. The term "oligonucleotide" may be DNA and/or RNA and/or analogs thereof and/or DNA RNA chimeric/or single stranded or double stranded/or partial double strand and partial single strand. The term oligonucleotide does not denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, it may contain detection reagents for signal generation/amplification, and it may function to prevent hybridization or impede primer extension if appropriately situated and/or modified. Specific oligonucleotides of the present invention are described in more detail below. As used herein, an oligonucleotide can be virtually any length, limited only by its specific function in the amplification reaction or in detecting an amplification product of the amplification reaction. As intended by this disclosure, an oligonucleotide does not consist solely of wild-type chromosomal DNA or the in vivo transcription products thereof. Oligonucleotides may be modified in any way, as long as a given modification is compatible with the desired function of a given oligonucleotide as can be easily determined. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl (2'-O-ME) substitution to the ribofuranosyl moiety. See "Method for Amplifying Target Nucleic Acids Using Modified Primers," (Becker, Majlessi, & Brentano, 2000, U.S. Pat. No. 6,130,038). Other sugar modifications include, but are not limited to 2'-amino, 2'-fluoro, (L)-alpha-threofuranosyl, and pentopuranosyl modifications. The nucleoside subunits may be joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. (DNA analogs having a pseudo peptide backbone are commonly referred to as "peptide nucleic acids" or "PNA" and are disclosed by Nielsen et al., "Peptide Nucleic Acids," (Nielsen, Buchardt, Egholm, & Berg, 1996, U.S. Pat. No. 5,539,082). Other linkage modifications include, but are not limited to, morpholino bonds. Non-limiting examples of oligonucleotides or oligomers contemplated by the present invention include nucleic acid analogs containing bicyclic and tricyclic nucleoside and nucleotide analogs (LNAs). See Imanishi et al., "Bicyclonucleoside and Oligonucleotide Analogues," (Imanishi & Obika, 2001, U.S. Pat. No. 6,268,490); and Wengel et al., "Oligonucleotide Analogues," (Wengel & Nielsen, 2003, U.S. Pat. No. 6,670,461). Any nucleic acid analog is contemplated by the present invention provided the modified oligonucleotide can perform its intended function, e.g., hybridize to a target nucleic acid under stringent hybridization conditions or amplification conditions, or interact with a DNA or RNA polyrnerase, thereby initiating extension or transcription. In the case of detection probes, the modified oligonucleotides must also be capable of preferentially hybridizing to the target nucleic acid under stringent hybridization conditions. The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically. A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected; the detection of this sequence may be by either direct or indirect means). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence. The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Stability of a nucleic acid duplex is measured by the melting temperature, or "$T_m$."

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral.

The term "foldback primer" as used herein, refers to a primer containing a region that can hybridize to the downstream of the same strand DNA molecule when this primer is extended during the amplification by DNA polymerase. Exemplary foldback primers include, without limitation, the FIP and BIP primers in LAMP and GEAR amplification, the turn-back primer in SMAP amplification and extruding primers in Omega amplification.

The term "foldback primer amplification" as used herein, describes as any isothermal amplification that uses one or more than one primers that have a region which can hybridize to the downstream of the same strand. DNA molecule when this primer is extended during the amplification by DNA polymerase. Exemplary foldback primer amplification include, without limitation, LAMP, SMAP, GEAR, and OMEGA. In one embodiment, a foldback primer may be used in the NEAR reaction. In such case, NEAR amplification is also counted as foldback primer amplification.

The term "hairpin" as used herein, describes a structure formed by a polynucleotide whose 5' and 3' regions form a substantial double-helix. A hairpin primer is a primer containing a hairpin structure as part or whole of the primer and this hairpin structure can exist at 5' region or internal region of the primer. The 5' region of hairpin sequences will not hybridize to the same strand downstream sequences after 3' end polymerase extension.

The term "extruding primer or extruding probe" as used herein, refers to an oligonucleotide that is used as a primer or a probe containing three regions. The first region at 3' end hybridizes with target DNA for polymerase extension. The second region, in the middle of the extruding primer or probe, can hybridize to the downstream of the same strand DNA molecule when this primer is extended during the amplification by DNA polymerase. The third region at 5' end, called an extruding sequence, does not hybridize to the downstream of the same strand DNA molecule when this primer or probe is extended during the amplification by DNA polymerase. The third region may have any kind of folding structure or may be single stranded or double stranded or may contain any modified nucleotides. Any primer in foldback primer amplification with extra sequences added at its 5' end that does not hybridize to the downstream of the same strand DNA molecule when this primer is extended during the amplification by DNA polymerase will be counted as an extruding primer or extruding probe. Additional artificial sequences or any unnatural nucleotides can be included between first region and second region.

The term "extruding sequence" as used herein, refers to an oligonucleotide sequence located at the 5' end of an extruding primer or extruding probe that does not hybridize to the downstream of the same strand DNA molecule when this primer is extended during the amplification by DNA polymerase. The extruding sequence may include natural or unnatural nucleotides or modified nucleotides such as Inosine. The extruding sequences may be chimeric sequences. Extruding sequence may include nicking site, promoter sequences or any other functional sequences or nucleotides that may be used to facilitate target amplification and detection.

The term "substantially single-stranded" when used in reference to a nucleic acid region means that the nucleic acid region exists primarily as a single strand in contrast to a double-stranded region which exists as two strands of nucleic acid which are held together by inter-strand base pairing interactions.

The term "thermostable" when used in reference to an enzyme, such as a DNA polymerase, indicates that the enzyme is functional or active (e.g., can perform catalysis) at an elevated temperature, e.g., at about 55° C. or higher.

The term "target nucleic acid" refers to a nucleic acid molecule which contains a sequence which has at least partial complementarity with at least a probe oligonucleotide and may also have at least partial complementarity with an invader oligonucleotide. The target nucleic acid may comprise single- or double-stranded DNA or RNA.

The term "amplicon nucleic acids" as used herein refers to any and all of the copies of the template nucleic acid strand or complement of generated by the amplification reactions from target nucleic acids.

The term "specific probe sequence" or "specific detection sequence" refers to either an oligonucleotide or its complementary sequence or an oligonucleotide paired with its complementary sequence oligonucleotide which links to 5' end a primer or a probe and interacts with a universal detection probe or a chemical or an oligonucleotide or its complementary sequence which itself can be detected because of sequence or structures features existed in this specific detection sequence. The specific detection sequence may have internal modification with a moiety to stop polymerase extension. The specific detection sequence may include unnatural nucleotides.

The term "a specific detection probe or a detection probe" refers to a probe or a primer includes a specific detection sequence that can be used to monitor amplification reaction through monitoring signal change from a specific detection probe or a detection probe or interaction between specific detection sequence and universal detection probe. In another embodiment, the specific detection probe includes a specific detection sequence that may have special structure features which interacts with special chemicals or ligands to monitor amplification reaction. Example of the special structure feature is G-quadruplex structures or aptamer structures such as ATP aptamer. in Omega amplification, monitoring amplification can monitor a detection probe signal change directly without monitoring interaction between a detection probe and a universal detection probe. For instance, a detection probe is a primer with a universal FQ probe attached at 5' end of primers. In this case, two oligonucleotide strands, wherein a first oligonucleotide strand comprises a quencher probe positioned at a 3' end and a second oligonucleotide strand of the universal FQ probe comprises a fluorophore positioned at a 5' end and is complementary to the first oligonucleotide stand at its 5' portion. The 3' region of the second oligonucleotide strand of the universal FQ probe will hybridize to template as a primer to be extended by a strand displacement polymerase.

The term "universal FQ probe" as used herein refers to two oligonucleotide strands, wherein the first FQ oligonucleotide strand comprises a quencher moiety and the second FQ oligonucleotide strand comprises a fluorophore, or the first FQ oligonucleotide strand comprises a fluorophore and the second FQ oligonucleotide strand comprises a quencher moiety. The first and second oligonucleotide strands are complementary and when annealed the quencher moiety quenches the fluorescence of the fluorophore. The first and second strands are configured so that the first strand can be displaced from the second strand or vice versa allowing the fluorophore to fluoresce. In certain embodiments, one strand anneals to a 3' portion of the other strand allowing an FQ primer to anneal and displace the one strand annealed to the 3' portion of the other strand. In certain embodiments, the first and second oligonucleotide strands of the universal FQ probe are part of a single oligonucleotide strand folded back on itself. Either strand may include secondary structure or aptamer sequences to facilitate its replacement by FQ invader. The second oligonucleotides may include secondary structure or modified nucleotides to facilitate replacement of the FQ invader kicker once it is extended using the second oligonucleotides as template.

The term "universal detection probe" as used herein refers to an oligonucleotide that will interact with specific probe sequences directly or indirectly. Universal detection probes preferably will not interact with the template nucleic acid. The universal detection probes can be single stranded or double stranded oligonucleotides. These oligonucleotides can include natural or un-natural nucleotides. The universal detection probe can have secondary structures such as stem loop hairpin structures. The universal detection probes can include one or more than one oligonucleotides. The specific detection probe can initiate sequential interaction amount these universal detection probes if more than one universal detection probes included in order to generate detectable amplification signal. The interaction between specific probe sequence and universal detection probes can be polymerase dependent or independent of polymerase activity. When polymerase involves the interaction between specific probe sequences and universal detection probes, both specific probe sequences and universal detection probe can be used either as a primer or a template. A typical example of a universal detection probe is the universal FQ probe that may include four basic components—a universal primer (FQ invader kicker), a trigger (FQ invader, a part of the specific detection probe), a spine sequence (the second strand FQ probe), and a spine cover (the first strand of the FQ probe). A trigger refers to an oligonucleotides that can interact with the spine and initiate a cascade of signal amplification and detection reactions. The trigger is portion of the specific detection probe sequences or reverse complementary sequence of the portion of the specific detection probe sequences, or it can be any sequence generated or released during amplification. The spine is an oligonucleotides containing complementary sequence of the FQ invader kicker, the FQ invader, and the spine cover (the first strand of the FQ probe). A spine cover is hybridized with spine and prevents the FQ invader kicker from being extended when the trigger is not hybridized with spine. When the trigger is available and hybridizes with the spine, separates the spine cover form the spine, and allows the FQ invader kicker to hybridize with the spine and to get extended by a DNA polymerase with strand displacement activity. In turn, the trigger gets displaced and hybridizes with another un-reacted spine. Some formats may combine two of the basic components in a single oligonucleotides via a stem loop structure. Some formats of the universal detection probe may already have a trigger hybridized with its complementary sequence as part of the spine or as a separate oligonucleotides in order to exponentially amplify fluorescent signal. Some formats of the universal detection probe may carry the fluorophore and quencher on spine and spine cover, or vice versa, whereas other formats may carry fluorophore and quencher in the FQ invader kicker, or a separate universal FQ probe is provided to generate fluorescent signal. Some formats may only carry fluorophore without a quencher in the system, and use intercalating dye as a fluorescence quencher (patent pub. NO.: US 2012/0282617 A1).

The term "FQ invader" refers to a part of specific probe sequence released or generated during amplification. The FQ invader interacts with the universal detection probe or universal FQ probe wherein the FQ invader anneals to the second strand of the FQ probe, displaces the first strand of the FQ probe from the FQ probe and in turn separates the fluorophore from the quencher, allowing the fluorophore to fluoresce. Alternatively, the FQ invader can be used as a template to interact with universal detection probe to generate detection signal.

The term "FQ invader kicker" refers to a specific oligonucleotide that will hybridize to the second strand of the FQ probe only after the FQ invader anneals to the second strand of the FQ probe. Under strand displacement amplification condition, FQ invader kicker is a primer to use the second stand of the FQ probe as a template to be extended to replace FQ invader. The newly replaced FQ invader can be cycled to initiate another round signal generation. The FQ invader kicker may attach fluorescent dye to generate detectable amplification signal. The FQ invader kicker may include artificial sequences at its 5' end. The FQ invader kicker may include mismatch near its 3' end when it hybridizes to the second strand of the FQ probe.

The term "FQ invader kicker replacement" refers to a primer or a probe or a reaction that will replace the FQ invader kicker once the FQ invader kicker is extended along the second strand of the FQ probe. The FQ invader kicker replacement can occur based on nicking extension replacement reaction, aptamer reaction, strand exchange reaction, etc.

The term "sequence variation" as used herein refers to differences in nucleic acid sequence between two nucleic acids. For example, a wild-type structural gene and a. mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "displacement" as used herein refers to the release of an oligonucleotide or part of an oligonucleotide from the base-paring interaction with its complimentary sequences by the action of certain polymerases with strand-displacement activity during nucleic acid synthesis.

The term "nucleotide analog or unnatural nucleotide" as used herein refers to modified or non-naturally occurring nucleotides such as 7-deaza purines (e.g., 7-deaza-dATP and 7-deaza-dGTP), inosine, etc. Nucleotide analogs include base analogs and comprise modified forms of deoxyribonucleotides as well as ribonucleotides.

The term "sample" in the present specification and claims is used in its broadest sense. On the one hand it is meant to include a specimen or culture (e.g., microbiological cultures). On the other hand, it is meant to include both biological and environmental samples. "Patient samples" include any sample taken from a subject and can include blood, saliva, cerebral spinal fluid, pleural fluid, milk, lymph, sputum, semen, stool, swabs, Broncho Alveolar Lavage Fluid, tissue samples, or urine. Other suitable patient samples and methods of extracting them are well known to those of skill in the art. A patient or subject from whom the sample is taken may he a human or a non-human animal. When a sample is not specifically referred to as a patient sample, the term also comprises samples taken from other sources. Examples include swabs from surfaces, water samples (for example waste water, marine water, lake water, drinking water), food samples, cosmetic products, pharmaceutical products, fermentation products, cell and microorganism cultures and other samples in which the detection of a microorganism is desirable. Biological samples may be obtained from all of the various families of domestic animals, as well as feral or wild animals, including, but not limited to, such animals as ungulates, bear, fish, lagomorphs, rodents, etc.

The term "source of target nucleic acid" refers to any sample which contains nucleic acids (RNA or DNA). Particularly preferred sources of target nucleic acids are biological samples including, but not limited to blood, saliva, cerebral spinal fluid, pleural fluid, milk, lymph, sputum, semen, stool, swabs, Broncho Alveolar Lavage Fluid, tissue samples, or urine.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "polymerization means" refers to any agent capable of facilitating the addition of nucleoside triphosphates to an oligonucleotide. Preferred polymerization means comprise DNA polymerases.

As used herein, the term "purified" or "to purify" refers to the removal of contaminants from a sample, The term "recombinant DNA molecule" as used herein refers to a DNA molecule which is comprised of segments of DNA joined together by means of molecular biological techniques.

"Nucleic acid sequence" as used herein refers to an oligonucleotide or polynucleotide, and fragments or portions thereof, which may be single- or double-stranded, and represent the sense or antisense strand. As used herein nucleic acids can be DNA, RNA. and chimeras thereof. Nucleic acids can be naturally produced or artificially synthesized. Nucleic acids can include or be entirely comprised of non-naturally occurring nucleotides as long as the regions that need to anneal can anneal under the reaction conditions. By way of example, nucleic acids may have a backbone is formed partially or entirely by phosphorothioate bonds. The number of nucleotides making up a nucleic acid as disclosed herein is not limited unless expressly specified. For example, the nucleic acids of the template molecule can be intact eukaryotic chromosomes. Similarly, "amino acid sequence" as used herein refers to peptide or protein sequence.

"Peptide nucleic acid" ("PNA") as used herein refers to a molecule which comprises an oligomer to which an amino acid residue, such as lysine, and an amino group have been added. These small molecules, also designated anti-gene agents, stop transcript elongation by binding to their complementary strand of nucleic acid [Nielsen PE et al. (1993) Anticancer Drug Des. 8:53-63].

DETAILED DESCRIPTION

The various implementations of foldback primer amplification all rely upon generation of a new, free 3' OH for extension when the foldback primer is extended during the amplification by DNA polymerase from which additional complementary strand synthesis can occur. Certain aspects of the compositions, reactions, methods, and kits disclosed herein are based upon the surprising discovery that the foldback primer amplification efficiency is not dramatically affected when one or more of the foldback primers have one or more extra nucleotides at its 5' end that prevents such generation of a new, free 3' OH for extension (despite Example 1 of U.S. Pat. No. 7,175,985 indicating that even a single nucleotide mismatch at the 5' terminus of a foldback primer can inhibit amplification). The inventors of the present application surprisingly discovered that an extruding sequence can be added at the 5' terminus of the foldback primer where the extruding sequence does not hybridize to the downstream of the same strand DNA molecule when this foldback primer is extended during the foldback primer amplification by DNA polymerase. This prevents one important mode of amplification since the foldback primer after replication does not provide a new free 3' OH for replication due to the presence of the extruding sequence. However, even without this additional 3' OH mode of extension downstream of the same DNA strand molecular amplification, the omega amplification reactions disclosed herein can still be nearly as fast as the amplification reaction where the foldback primer does not have the extruding sequence. In certain aspects, the omega amplification is at least 20% as fast, at least 30% as fast, at least 40% as fast, at least 50% as fast, at least 60% as fast, at least 70% as fast, at least 80% as fast, at least 90% as fast, or even at least 100% as fast as the corresponding foldback amplification without any extruding sequences on the foldback primers.

Omega amplification distinguishes from LAMP, SMAP and GEAR. since at least one of the foldback primers will include an extruding sequence at its 5' terminus that will not hybridize to the downstream of the same strand DNA molecule when this primer is extended during the amplification by DNA polymerase. Omega amplification reactions as used herein are a subset of foldback primer amplification reactions. in some embodiments, the extruding sequence is found at one (or both ends) of an amplicon nucleic acid. The extruding sequence preferably will not hybridize to the downstream of the same strand DNA molecule when this primer is extended during the amplification by DNA polymerase or at least will not anneal to the template nucleic acid in proximity to the amplified portion of the template nucleic acid.

The extruding sequence is at least 1, 2, 3, 4, 5, 7, 8, 9 10, 12, 14, 16, 18, 20, 25, 30, 35, 40, 45, 50, 60, 70, 80, 90, 100, 150, or 200 nucleotides. The extruding sequence can be less than 500, 450, 400, 350, 300, 250, 200, 150, 100, 90, 80, 70, 60, 50, 45, 40, 35, 30, 25, or 20 nucleotides. In certain aspects, the extruding sequence can be 1 to 100 nucleotides, 2 to 75 nucleotides, 3 to 50 nucleotides, or 4 to 30 nucleotides in length. The extruding sequence can be of any sequence as long as the sequence will not provide a free '3 OH to hybridize to the downstream of the same strand DNA molecule when this primer is extended during the omega amplification reaction. By way of example, the extruding sequence in a forward foldback primer will not anneal to the region immediately 3' of the F1T region of the template second strand. In some embodiments, the extruding sequence comprises a G-quadruplex, a T7 promoter sequence, a nicking site, or an FQ sequence. In some embodiments, the extruding sequence will be Guanidine-rich (G-rich) because G-rich extruding sequences can accelerate the omega amplification reactions. In some embodiment, the extruding sequence may have a hairpin structure including modified nucleotides or unnatural nucleotides.

The extruding sequence is an arbitrary sequence since it will not hybridize to the downstream of the same strand DNA molecule when this primer is extended during the amplification by DNA polymerase. The extruding sequence that is unique to OMEGA amplification technology allows introduction of any additional sequences that can be used for detection (especially for multiplex reaction), further acceleration of the amplification reaction, and other uses.

Another aspect of the present disclosure is to improve foldback primer amplification speed and sensitivity. In one embodiment, the current invention discovered that more than one sets of kick primers (forward kick primer and reverse kick primer) used in the amplification reaction can improve foldback primer amplification sensitivity. In another embodiment, the kick primer having extra sequence at 5'end that can hybridize to the downstream of the same strand DNA molecule when the kick primer is extended during the amplification by DNA polymerase that will increase reaction speed and also improve amplification sensitivity. In another aspect, the current invention discovered that loop accelerate primer has extra sequence at it's 5' end that can hybridize to the downstream of the same strand DNA molecule when the loop accelerate primer is extended during foldback primer amplification by DNA polymerase. In another aspect, a free 3' OH from the complementary of the loop accelerate primer which a complementary strand synthesized during the foldback primer amplification reaction can be used as primer to initiate additional reaction and amplification. In another aspect, extra sequences can be added to the stem primers (WO2010146349). The extra sequence of the stem primers can hybridize to the downstream sequences or any artificial sequences as long as they can help to speed up the amplification reactions. In another aspect, extra primers may be added to the reaction mixture that are the same sequence as the regions of the folding sequence of FIB or BIP or the same as extruding sequences can be added into the reactions. In another aspect, for the same primer such as a HP as an example, the amplification reaction mixture can include the FIP primer both with extruding sequence HP and without extruding sequence HP primer. The ratios of with extruding sequence FIP and without extruding sequence FIP primer can be used to adjust the amplification reaction speed or sensitivity. In another aspect, the GC content of the folding regions of the foldback primers can be used to adjust the reaction speed and sensitivity. The GC content is between 10 to 20%, 20 to 30%, 30 to 40%, 40 to 50%, 50 to 60%, 60 to 70%, 70 to 80%, ideally between 30 to 40%. For NEAR amplification, one or both primers may be designed as extruding primers. The nicking site will be located within extruding sequences. For TMA amplification, one or both primers may be designed as extruding primers. The promoter sequences will be located within extruding sequences.

Another aspect of present invention is to use OMEGA technology to detect mutations. The first nucleotide of 3' end specific probe sequence primer or probe will hybridize over the mutation site and the second nucleotide of 3'end specific probe sequence will be mismatched with the template. Once both the 3' end first and second base are mismatched with template, polymerase will not be able to extend the specific probe sequence primer or probe and no amplification signal is detected. However when the first nucleotide matches with the template, polymerase will be able to extend the specific probe sequence primer or probe and the amplification signal is detected. The same principle can be used to detect DNA methylation.

Additional aspects of the compositions, reactions, methods and kits disclosed herein are based upon novel methods of detection that can be used with the foldback amplification reactions disclosed herein including universal FQ probes and G-quadruplex probes.

Figure 1B:
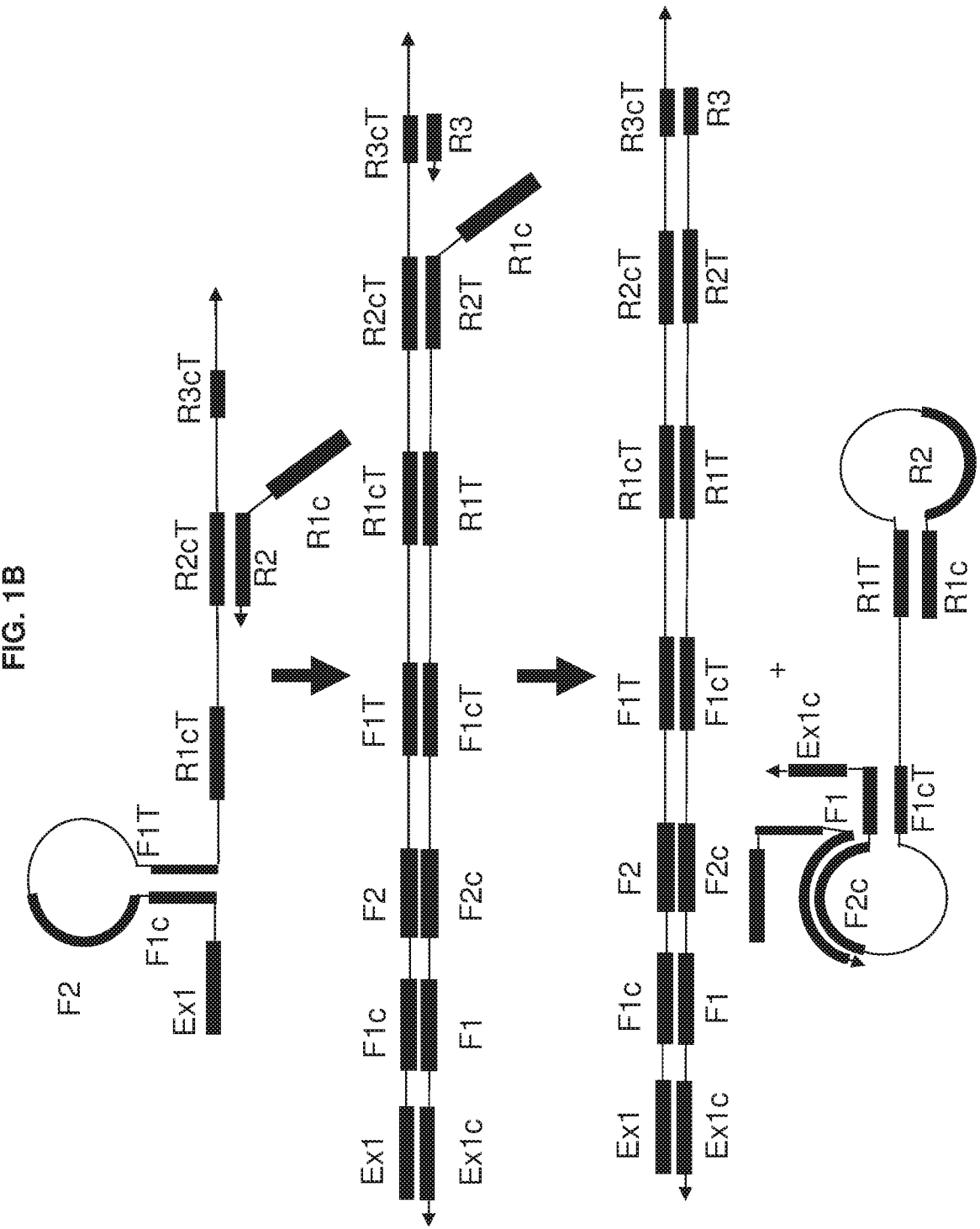

As used herein, a template nucleic acid typically has a first strand that has from 5' to 3': an optional F3 template sequence (F3T, FIG. 1), an F2 template sequence (F2T, FIG. 1), an F1 template sequence (F1T, FIG. 1), an R1 complementary template sequence (R1cT, FIG. 1), an R2 complementary template sequence (R2cT, FIG. 1), and an optional R3 complementary template sequence (R3cT, FIG. 1). A template nucleic acid typically has a second strand that has from 5' to 3': an optional R3 template sequence (R3T, FIG. 1), an R2 template sequence (R2T, FIG. 1), an R1 template sequence (R1T, FIG. 1), an F1 complementary template sequence (F1cT, FIG. 1), an F2 complementary template sequence (F2cT, FIG. 1), and an optional F3 complementary template sequence (F3cT). In some cases (e.g., GEAR amplification) the F1T and R1cT overlap or are one in the same region (with the corresponding being true for the F1cT and R1T, FIG. 1). While a template nucleic acid has a first and second strand, the amplification reactions herein can initiate when a sample only has the first strand or the second strand of the template.

The template nucleic acid to be used in the reactions disclosed herein include without limitation, cDNA, genome DNA, DNA-RNA hybrids, mRNA, miRNA, rRNA, tRNA, etc. In addition, the template nucleic acid can be inserted in a vector (and can include part of the vector and part of the insert). The target nucleic acid used in the reactions disclosed herein may be purified or crude nucleic acid or chemically synthesized. Moreover, the reactions disclosed herein can be performed with target nucleic acid in cells (in situ). In-situ genomic analysis can be performed using as the template a double-stranded or single stranded nucleic acid in cells.

When an mRNA (or other RNA) is a template nucleic acid, the mRNA may first be converted to an RNA-DNA hybrid or cDNA through use of a reverse transcriptase. Preferably, the reverse transcriptase is active under the reaction conditions and can therefore be included in the amplification reaction mixture. When the DNA polymerase used in the amplification reactions disclosed herein has a reverse transcriptase activity, the RNA-DNA hybrid or cDNA synthesis can be performed using it as a single enzyme under the same conditions as for the amplification reaction. For example, Bca DNA polymerase or BST DNA polymerase is a DNA polymerase having strand displacement activity as well as reverse transcriptase activity. As a matter of course, the amplification reactions disclosed herein can also be performed after the formation of the RNA-DNA hybrid or even after complete double-stranded cDNA by the second strand synthesis, which can be performed separately from the amplification reaction, The "amplicon nucleic acids" are any and all of the copies of the template nucleic acid strand generated by the amplification reactions disclosed herein. The first primer dependent copy of the template nucleic acid generated by the amplification reactions disclosed herein is the "principal amplicon". The first copy of the principal amplicon generated by the amplification reactions disclosed herein is the "first generation amplicon." Further copies of the first generation amplicon (and copies of these copies, etc.) generated by the amplification reactions disclosed herein are the "next generation amplicons". The amplicon nucleic acids therefore include all of the principal amplicons, the first generation amplicons, and the next generation amplicons.

As used herein nucleic acids can be DNA, RNA, and chimeras thereof. Nucleic acids can be naturally produced or artificially synthesized. Nucleic acids can include or he entirely comprised of non-naturally occurring nucleotides as long as the regions that need to anneal can anneal under the reaction conditions. By way of example, nucleic acids may have a backbone is formed partially or entirely by phosphorothioate bonds. The number of nucleotides making up a nucleic acid as disclosed herein is not limited unless expressly specified. For example, the nucleic acids of the template molecule can be intact eukaryotic chromosomes.

In some embodiments, the present invention relates to means for signal generation during nucleic acid strand-displacing amplification, such as, but not limited to, LAMP, SMAP, NEAR, NASBA, TMA, RCA, and EXPAR. In one aspect, methods of monitoring isothermal amplification of a target DNA are provided. The methods generally comprise providing a reaction mixture comprising a target DNA and one or more target-specific primers capable of amplifying the target DNA. A specific probe sequence is linked to the 5' of a target-specific primer. The specific probe sequence can be arbitrary sequences. Detection the interaction between the specific probe sequences and other oligonucleotides or chemicals monitors the isothermal amplification for nucleic acid template amplification and detection. For instance, a universal FQ probe is also provided where the probe comprises two oligonucleotide strands, wherein a first oligonucleotide strand comprises a quencher probe positioned at a 3' end and wherein a second oligonucleotide strand of the universal FQ probe comprises a fluorophore conjugated at a 5' end and is complementary to the first oligonucleotide stand at its 5' portion. The 3' portion of the second oligonucleotide stand contains a full or part of the specific probe sequence. A ratio of the amount of the second oligonucleotide strand to the amount of the first oligonucleotide strand that is added to the reaction mixture may be less than 1:1. A DNA polymerase may also be added to the reaction mixture. Fluorescence emitted by the reaction mixture including the specific probe and the FQ probe and the target DNA can be measured. The present invention contemplates use of novel detection methods for various uses, including, but not limited to clinical diagnostic purposes. In some embodiment, the universal detection probe may be single strand oligonucleotides, wherein the quencher and fluorophore may be labeled at 3' or 5' end or at middle of the oligonucleotides. In another embodiment, the universal detection probes comprises more than one set of oligonucleotides, wherein the specific detection probe initiates the sequential interaction amount the sets of the universal detection probe oligonucleotides to generate exponential amplification detection signal.

The interaction between the complementary sequence of the specific probe sequence and the universal detection probe can be DNA polymerase independent, such as in the case of molecular beacon and Yin-yang probes. In this case, the hybridization of the complementary sequence of the specific probe sequence to the universal FQ probe causes separation or structural change between the fluorescent and quench moieties in the FQ probe, giving the fluorescent signal. The interaction between the complementary sequence of the specific probe sequence and the universal FQ probe can alternatively be DNA polymerase dependent. In this case, the newly synthesized/displaced complementary sequence of the specific probe sequence serves as a primer on the universal FQ probe and extends on the FQ probe as template, displacing the quench moiety away from the fluorescent moiety of the FQ probe and giving the fluorescent signal. In another case, the newly synthesized/displaced complementary sequence of the specific probe sequence serves as a template for the universal FQ probe and extends on the specific probe sequence to generate the fluorescent signal changes.

For an efficient LAMP reaction, six primers are used (two inner primers, two outer primer and two loop primers). A specific probe sequence can be attached upstream to the loop primer sequences. LAMP reaction will result the synthesis of the complementary sequences of the specific probe sequence. When the universal FQ probe is provided, the newly synthesized complementary sequences of the specific probe sequence will hybridize onto the single-stranded region of the universal FQ probe and get extended along the FQ probe by strand-displacing polymerases, resulting in the separation of fluorescent and quenching oligos and hence the generation of fluorescence In another embodiment, the specific probe sequences are attached upstream to the sequences of inner primers in the LAMP (FIP and BIP) In another embodiment, the specific probe sequences are attached upstream to the sequences of gap primers (stem primers) in the LAMP. In another embodiment, the specific probe sequences are attached upstream to the sequence of loop primer in the SMAP reaction. In another embodiment, the specific probe sequences are attached upstream to the sequences of foldback primer (FP) in the SMAP reaction, In another embodiment, the specific probe sequences are attached upstream to the sequences of gap primers (stem primers) in the SMAP reaction. In another embodiment, the specific probe sequences are attached upstream to the sequences of inner primers in the GEAR (HP and BIP). In another embodiment, the specific probe sequences are attached upstream to the sequences of loop primers (LF and LB) in the GEAR reaction. In another embodiment, the specific probe sequences are attached upstream to any primers that do not contain a nicking enzyme recognition site in the NEAR reaction.

In another embodiment, a second oligonucleotide that is complementary to the specific probe sequence can be added and form a double-helix with the specific probe sequence. Upon the reaction, the second oligo will be displaced off the specific probe sequence and can interact with the universal FQ probe to generate fluorescence.

In another embodiment, the second oligonucleotide contains a G-quadruple sequence. Once it is replaced from the specific probe sequences and this oligonucleotides folds into a correct G-quadruplex conformation which can be detected by G-quadruplex detection methods known to those of skill in the art.

In another embodiment, the second oligonucleotides contains an aptamer sequences. Once it is replaced from the specific probe sequences and this oligonucleotides folds into a correct aptamer conformation which can be detected by aptamer detection methods known to those of skill in the art.

In another embodiment, the single stranded specific probe sequence contains an RNA transcription promoter sequence. Upon the amplification reaction, the complementary strand of this primer will be synthesized which will generate a functional RNA transcription promoter. In the presence of NTPs and the RNA polymerase that can initiate RNA transcription from this promoter, large amount of RNA transcripts will be generated. These RNA transcripts can be detected by methods known to those of skill in the art.

In another embodiment, the single stranded specific probe sequence contains a. nicking endonuclease recognition sequence. Upon the amplification reaction, the complementary strand of this primer will be synthesized which will generate a functional nicking endonuclease recognition site. In the presence of a corresponding nicking endonuclease, the double-stranded DNA will be nicked at a pre-defined position. The strand-displacing polymerase will extend the nicked DNA strand and displace a single-stranded DNA which can be used as template for further amplification. In one embodiment, the universal FQ probe is a molecular beacon. in another embodiment, the universal FQ probe is a yin-yang probe. In another embodiment, the universal probe is a circular DNA. In some embodiments, the newly synthesized complementary sequence of specific probe sequence initiates rolling circle amplification (RCA) and the resulted RCA products are detected by methods known to those of skill in the art.

In another embodiment, the universal probe is an EXPAR substrate. In some embodiments, the newly synthesized complementary sequence of specific probe sequence initiates an EXPAR cascade and the resulting EXPAR products are detected by methods known to those of skill in the art.

In another embodiment, the universal probe is a FQ invader nucleic acid. In some embodiments, the FQ invader first anneals to the single stranded portion of the FQ probe and then displaces the second strand of the FQ probe where the FQ invader overlaps with the double stranded portion of the FQ probe. Displacing the second strand of the FQ probe from the FQ probe separates the fluorophore from the quencher, allowing the fluorophore to fluoresce.

Additional aspects of this disclosure and their various embodiments are [1] A method of detecting a template nucleic acid in a sample using a strand displacement isothermal amplification reaction comprising (i) generating the reaction by combining the sample with
(a) one or more amplification primers configured to generate amplicon nucleic acids from the template nucleic acids under suitable amplification conditions, and (b) a strand displacement amplification polymerase;

(ii) maintaining the reaction under the suitable amplification conditions; and (iii) detecting whether amplification occurs or has occurred in step (ii) by monitoring during or after step (ii) interaction between (c) a specific detection probe that, under the suitable amplification conditions, hybridizes to the template nucleic acid, its compliment, the amplicon nucleic acid or its compliment, and (d) a universal detection probe.

[2] The method of [1], wherein the universal detection probe is a universal FQ probe.

[3] The method of [1] or [2], wherein the universal detection probe does not anneal to the template nucleic acid or its complement under the suitable amplification conditions

[4] The method of any one of [1-3], wherein the interaction between the specific detection probe and the universal detection probe is through hybridization during the amplification.

[5] The method of any one of [1-3], wherein the interaction between the specific detection probe and the universal detection probe is through hybridization between the complement of the specific detection probe and the universal detection probe.

[6] The method of any one of [1-3], wherein the interaction between the specific detection probe and the universal detection probe is through hybridization and polymerase extension during the amplification.

[7] The method of any one of [1-3], wherein e specific detection probe comprises an internal chemical moiety to stop polymerase extension.

[8] The method of any one of [1-7], wherein the universal detection probe comprises a first detection oligonucleotide strand and a second detection oligonucleotide strand.

[9] The method of [8], wherein (a) the first detection oligonucleotide strand comprises a quencher moiety and the second detection oligonucleotide strand comprises a fluorophore, or (b) the first detection oligonucleotide strand comprises a fluorophore and the second detection oligonucleotide strand comprises a quencher moiety, wherein the quencher moiety and the fluorophore are configured so that the quencher moiety quenches the fluorescence of the fluorophore when first detection oligonucleotide strand and a second detection oligonucleotide strand are annealed.

[10] The method of [9], wherein the ratio of the amount of the detection oligonucleotide strand comprising the fluorophore to the amount of the detection oligonucleotide strand comprising the quencher moiety is less than 1:1.

[11] The method of [9] or [10], wherein the detecting step (ii) comprises measuring fluorescence emitted during the isothermal strand displacement amplification.

[12] The method of any one of [8-11], wherein the second detection oligonucleotide strand comprises an overhanging unmatched segment that is not complementary to the first detection oligonucleotide strand.

[13] The method of any one of [8-12], wherein the specific detection probe or its complement includes an invader that hybridizes to a portion of the overhanging unmatched segment and to a portion of the second detection oligonucleotide strand that is complementary to the first detection oligonucleotide strand during or after the amplification.

[14] The method of [12], further comprising an invader kicker probe includes mismatch near its 3' end or at 3' end when it hybridizes to the second detection oligonucleotide strand.

[15] The method of [14], further comprising an invader kicker replacement probe to replace the invader kicker probe once the invader kicker probe is extended along the second detection oligonucleotide strand.

[16] A method of detecting a template nucleic acid in a sample using a strand displacement isothermal amplification reaction comprising (i) generating the reaction by combining the sample with (a) one or more amplification primers configured to generate amplicon nucleic acids from the template nucleic acids under suitable amplification conditions, and (b) a strand displacement amplification polymerase;

(ii) maintaining the reaction under the suitable amplification conditions; and (iii) detecting whether amplification occurs or has occurred in step (ii) by monitoring during or after step (ii) an aptamer probe; wherein the aptamer probe is part of a specific detection probe that, under suitable amplification conditions, hybridizes to the template nucleic acid, its compliment, an amplicon nucleic acid or its compliment.

[17] The method of [16], the aptamer probe is a G-quadruplex probe.

[18] The method of [16] or [17], wherein the G-quadruplex probe generates a detectable signal selected from the group consisting of chromogenesis, fluorescence, luminescence, and chemiluminescence.

[19] The method of any one of [1-18], wherein the strand displacement amplification polymerase is selected from the group consisting of Bst DNA polymerase, Bca(exo-) DNA polymerase, Klenow fragment of DNA polymerase I, Vent DNA polymerase, Vent(Exo-) DNA polymerase (exonuclease activity-free Vent DNA polymerase), DeepVent DNA polymerase, DeepVent(Exo-) DNA polymerase (exonuclease activity-free DeepVent DNA polymerase), φ29 phage DNA polymerase, MS-2 phage DNA polymerase, Z-Taq DNA polymerase (Takara Shuzo), and KOD DNA polymerase (TOYOBO).

[20] The method of any one of [1-18], wherein the strand displacement amplification polymerase is Bst DNA polymerase or Bca(exo-) DNA polymerase.

[21] The method of any one of [1-20], wherein one of the amplification primers is foldback primer.

[22] The method of any one of [1-21], wherein the strand displacement isothermal amplification reaction is LAMP, SMAP, GEAR, NEAR, or CPA.

[23] The method of any one of [1-21], wherein the isothermal amplification reaction is omega amplification and the pair of primers are foldback primers and at least one of the foldback primers is extruding primer.

[24] The method of [23], wherein the extruding sequence in the extruding primer comprises the specific detection probe sequences.

[25] The method of [23] or [24], wherein the extruding sequence comprises internal modification to stop polymerase extension.

[26] The method of any one of [1-25], wherein the strand displacement isothermal amplification reaction comprises one or more than one kicker accelerator primers, or one or more than one stem accelerator primers, or one or more than one loop accelerator primers.

[27] The method of [26], wherein the kicker accelerator primer or loop accelerator primer or stem accelerator primer comprises folding sequences at its 5' end to fold onto its 3' end downstream sequences after 3' end is extended by a polymerase.

[28] The method of any one of [1-20], wherein the strand displacement isothermal amplification reaction is RCA.

[29] The method of any one of [1-20], wherein the strand displacement amplification is nicking amplification and step (i) includes combining a nicking enzyme included in the reaction.

[30] The method of any one of [1-29], wherein the specific detection probe is an oligonucleotide that participates in the isothermal strand displacement amplification.

[31] An omega amplification primer set comprising a first foldback primer and a second foldback primer that allow isothermal amplification under suitable omega amplification conditions of a portion of a target nucleic acid sequence, wherein the first foldback primer comprises a first extruding sequence at its 5' terminus or the second foldback primer comprises a second extruding sequence at its 5' terminus.

[32] The omega amplification primer set of [31], wherein:
(i) the target nucleic acid sequence has a first strand, wherein the first strand is complimentary to a complementary strand;
(ii) the first foldback primer includes from 5' to 3':
  (1-b) a sequence (F1c), wherein the sequence (F1c) hybridizes to a sequence (F1T) in the complimentary strand of the target nucleic acid sequence; and
  (1-c) at the 3' terminus, a sequence (F2), wherein the sequence (F2) hybridizes to a sequence (F2cT) in the first strand of the target nucleic acid sequence,
  wherein the sequence (F1T) is 3' of a sequence (F2T) in the complimentary strand; and the sequence (F2T) is complementary to the sequence (F2cT);
(iii) the second foldback primer includes from 5' to 3':
  (2-b) a second sequence comprising: a sequence (R1c), wherein the sequence (R1c) hybridizes to a sequence (R1T) in the first strand of the target nucleic acid sequence,
  (2-c) at the 3' terminus, a sequence (R2), wherein the sequence (R2) hybridizes to a sequence (R2cT) in the complimentary strand of the target nucleic acid sequence,
  wherein the sequence (R1T) is 3' of a sequence (R2T) in the first strand; and the sequence (R2T) is complementary to the sequence (R2cT); and
(iv) the primer set further comprises:
  (X) (1-a) a first extruding sequence at the 5' terminus of the first foldback primer, wherein the first extruding sequence is at least 4 nucleotides and cannot hybridize to the first strand or the complimentary strand, and wherein the sequence (R1c) is at the 5' terminus of the second foldback primer;
  (Y) (2-a) a second extruding sequence at the 5' terminus of the second foldback primer, wherein the second extruding sequence is at least 4 nucleotides and cannot hybridize to the first strand or the complimentary strand, and wherein the sequence (F1c) is at the 5' terminus of the first foldback primer; or
  (Z) (1-a) a first extruding sequence at the 5' terminus of the first foldback primers, wherein the first extruding sequence is at least 4 nucleotides and cannot hybridize to the first strand or the complimentary strand, and (2-a) a second extruding sequence at the 5' terminus of the second primer, wherein the second extruding sequence is at least 4 nucleotides and cannot hybridize to the first strand or the complimentary strand.

[33] The omega amplification primer set of [32], wherein a portion of the sequence (F1c) can hybridize to a portion of the sequence (R1c).

[34] The omega amplification primer set of [32], wherein the sequence (F1c) and the sequence (R1c) overlap by at least 1, 2, 3, 4, 5, 6, 7, 8, 9, 10, 12, 14, 16, 18, 20, 25, or 30 nucleotides.

[35] The omega amplification primer set of any one of [31-34], wherein the first extruding sequence or the second extruding sequence is at least 3, 4, 5, 6, 7, 8, 9, 10, 12, 14, 16, 18, 20, 25, 30, 35, 40, 45, 50, 60, 80, 90, 100, 150, or 200 nucleotides.

[36] The omega amplification primer set of any one of [31-35], wherein the first extruding sequence or the second extruding sequence is less than 500, 450, 400, 350, 300, 250, 200, 150, 100, 90, 80, 70, 60, 50, 45, 40, 35, 30, 25, or 20 nucleotides.

[37] The omega amplification primer set of any one of [31-36], wherein the first extruding sequence or the second extruding sequence is 3 to 100 nucleotides, 3 to 75 nucleotides, 3 to 50 nucleotides, or 4 to 30 nucleotides in length.

[38] The omega amplification primer set of any one of [31-37], wherein the first extruding sequence or the second extruding sequence comprises a G-quadruplex, an aptamer sequence, an RNA promoter sequence, a nicking sequence, or an FQ detection sequence.

[39] The omega amplification primer set of any one of [31-38], wherein the first extruding sequence or the second extruding sequence is G rich.

[40] The omega amplification primer set of any one of [31-39], wherein the omega amplification reaction comprises one or more than one kicker accelerator primers, or one or more than one stem accelerator primers, or one or more than one loop accelerator primers.

[41] The omega amplification primer set of any one of [31-40], wherein the kicker accelerator primer or loop accelerator primer or stem accelerator primer comprises folding sequences at its 5' end to fold onto its 3' end downstream sequences after 3' end is extended by a polymerase.

[42] The omega amplification primer set of any one of [31-41], wherein the first extruding primer or the second extruding primer has hairpin structure at its 5' terminus.

[43] The foldback primer amplification primer set of any one of [31-42], wherein foldback primer includes unnatural nucleotides.

[44] The foldback primer amplification primer set of any one of [31-43], wherein folding hybridization sequence includes unnatural nucleotides.

[45] A method for determining whether a sample includes a template nucleic comprising
(i) combining the sample with the set of omega amplification primers of any one of [31-44], a strand displacement amplification polymerase, and a detection probe; and
(ii) maintaining the combination under the suitable omega amplification conditions; and
(iii) determining whether the sample includes the template nucleic acid by monitoring whether the detection probe is involved in amplification during step (ii) or has been involved in amplification after step (ii).

[46] A method for assessing the amount of a template nucleic acid in a sample comprising
(i) combining the sample with the set of omega amplification primers of any one of [31-44], a strand displacement amplification polymerase, and a detection probe; and
(ii) maintaining the combination under the suitable omega amplification conditions; and
(iii) quantifying the amount of the template nucleic acid by monitoring the detection probe during or after step (ii).

[47] The method of [45] or [46], wherein the monitoring is performed during step (ii).

[48] The method of any one of [45-47], wherein the monitoring is based on a chromogenic reaction, a turbidity reaction, a chemiluminescent reaction, or a fluorescent reaction.

[49] The method of any one of [45-47], wherein the monitoring is monitoring fluorescent signal change from the detection probe.

[50] The method of any one of [45-49], wherein the detection probe has a universal FQ primer complement attached at its 5' end.

[51] The method of any one of [44-49], wherein the detection probe is a specific detection probe and the monitoring is based on interaction between the specific detection probe or its complement and a universal FQ probe during amplification or after amplification.

[52] The method of [51], wherein the universal FQ probe comprises a first FQ oligonucleotide strand and a second FQ oligonucleotide strand.

[53] The method of [52], wherein the first FQ oligonucleotide strand and the second FQ oligonucleotide strand do not hybridize to the template strand under the suitable omega amplification conditions.

[54] The method of [52] or [53], wherein (a the first FQ oligonucleotide strand comprises a quencher moiety and the second FQ oligonucleotide strand comprises a fluorophore, or (b) the first FQ oligonucleotide strand comprises a fluorophore and the second FQ oligonucleotide strand comprises a quencher moiety, wherein the quencher moiety and the fluorophore are configured so that the quencher moiety quenches the fluorescence of the fluorophore when first FQ oligonucleotide strand and a second FQ oligonucleotide strand are annealed and the detecting comprises measuring fluorescence emitted during the isothermal strand displacement amplification.

[55] The method of [54], wherein the ratio of the amount of the FQ oligonucleotide strand comprising the fluorophore to the amount of the FQ oligonucleotide strand comprising the quencher moiety is less than 1:1

[56] The method of any one of [52-55], wherein the second FQ oligonucleotide strand comprises an overhanging unmatched segment that is not complementary to the first FQ oligonucleotide strand.

[57] The method of [56], wherein the specific detection probe or its complement includes an invader that hybridizes to a portion of the overhanging unmatched segment and to a portion of the second detection oligonucleotide strand that is complementary to the first detection oligonucleotide strand during or after the amplification.

[58] The method of [57], further comprising an invader kicker probe includes mismatch near its 3' end or at 3' end when it hybridizes to the second detection oligonucleotide strand.

[59] The method of [58], further comprising an invader kicker replacement probe to replace the invader kicker probe once the invader kicker probe is extended along the second detection oligonucleotide strand.

[60] The method of any one of [45-59], wherein the detection probe or universal detection probe includes a G-quadruplex probe or an aptamer probe.

[61] The method of any one of [45-60], wherein the first extruding sequence or the second extruding sequence comprises the detection probe.

[62] The method of any one of [45-61], wherein the template nucleic acid is a human papilloma virus (HPV).

[63] The method of [62], wherein the HPV is HPV6, HPV11, HPV16, HPV18, HPV35, or HPV73.

[64] The method of [62], wherein the set of omega amplification primers are 18FIP (SEQ ID NO:1) and ex18BIP (SEQ ID NO:4), ex18FIP (SEQ ID NO:2) and 18BIP (SEQ ID NO:3), or ex18FIP (SEQ ID NO:2) and ex18BIP (SEQ ID NO:4), optionally including a kicker acceleration primer 18KF (SEQ ID NO:9) and/or 18KB (SEQ ID NO:10), optionally including a loop acceleration primer 18LF (SEQ ID NO:5) and/or 18LB (SEQ ID NO:6), and optionally including an FQ probe comprising FAM-18LB (SEQ ID NO:7) and Q-oligo (SEQ ID NO:8).

[65] The method of [62], wherein the set of omega amplification primers are 73ovlp-exELP (SEQ ID NO: 15) and 73-BIP (SEQ ID NO:18), 7350ovlp-exFIP (SEQ ID NO:16) and 73-BIP (SEQ ID NO:18), or 73-exFIP (SEQ ID NO:17) and 73-BIP (SEQ ID NO:18), optionally including a kicker acceleration primer 73-KF (SEQ ID NO:24) and/or 73-KB (SEQ ID NO:25), optionally including a loop acceleration primer 73ovlp-LF (SEQ ID NO:19), 7350ovlp-LF (SEQ ID NO:20), 73-LF (SEQ ID NO:21), and/or 73-LB (SEQ ID NO:22), and optionally including an FQ probe comprising Fam-73-LB (SEQ ID NO:23) and. Q-oligo (SEQ ID NO:8).

[66] The method of [62], wherein the set of omega amplification primers are HPV6G-FIP (SEQ ID NO:27)and HPV6G BIP-22nt (SEQ ID NO:29), optionally including a kicker acceleration primer HPV6G-KF (SEQ ID NO:33) and/or HPV6G-KB (SEQ ID NO:34), optionally including a loop acceleration primer 73ovlp-LF (SEQ ID NO:19), 7350ovlp-LF (SEQ ID NO:20), 73-LF (SEQ ID NO:21), and/or 73-LB (SEQ ID NO:22), and optionally including an FQ probe comprising Fam-73-LB (SEQ ID NO:23) and Q-oligo (SEQ ID NO:8),

[67] The method of [62], wherein the set of omega amplification primers are 35-exFIP (SEQ ID NO: 45) and 35-BIP (SEQ ID NO: 37), optionally including a kicker acceleration primer 35-KF (SEQ ID NO: 42) and/or 35-KB (SEQ ID NO: 43), optionally including a loop acceleration primer 35-LF (SEQ ID NO: 38), 35-FBLF (SEQ ID NO: 39), 35-LB (SEQ ID NO: 40), and/or 35-FBLB (SEQ ID NO: 41), and optionally including an FQ probe comprising 35-LF-FAM (SEQ ID NO: 44)) and Q-oligo (SEQ ID NO:8).

[68] A method of generating amplicon nucleic acids from a template nucleic acid in a sample using an omega amplification reaction comprising
 (i) combining the sample with the set of omega amplification primers of any one of [31-44], and a strand displacement amplification polymerase; and
 (ii) generating amplicon nucleic acids by maintaining the combination under suitable omega amplification conditions.

[69] A method using the set of primers of any one of [32-44] to make an amplicon nucleic acid from the target nucleic acid molecule, wherein the amplicon nucleic acid is capable of forming a first stem and loop at a first end, is capable of forming either a second stem and loop or a foldback loop at a second end, and has (i) the first extruding sequence located at the terminus of the first end, and/or (ii) the second extruding sequence located at the terminus of the second end, the method comprising:
 (a) combining a sample with the target nucleic acid molecule with the set of primers of any one of [32-44];
 (b) annealing the sequence (F2) of the first primer to the sequence (F2cT) in the first strand of the target nucleic acid molecule;
 (c) extending the first primer from its 3' end, using a suitable polymerase, to form a first single-stranded nucleic acid molecule comprising the first primer at the 5' end and the sequence (R2cT);

(d) displacing the first single-stranded nucleic acid molecule from the target nucleic acid sequence;

(e) annealing the sequence (R2) of the second primer to the sequence (R2cT) in the first single-stranded nucleic acid molecule; and (f) making the replicated portion of the target nucleic acid molecule by extending the second primer from its 3' end, using a suitable polymerase, to form a second single-stranded nucleic acid molecule comprising the second primer at the 5' end and a sequence complimentary to the first primer;

wherein the displacing step (d) is carried out by:

(i) annealing the sequence (F2) of an additional first primer to the sequence (F2cT) in the first strand of the target nucleic acid molecule and extending the additional first primer from its 3' end, using a suitable polymerase, to displace the first single-stranded nucleic acid molecule:

(ii) steps (d) and (e); or (iii) (1) providing a first kicker primer comprising, at its 3' terminus, a sequence (F3), wherein the sequence (F3) hybridizes to a sequence (F3cT) and the sequence (F3cT) is 5' of the sequence (F2cT) in the first strand of the target nucleic acid sequence;

(2) annealing the sequence (F3) in the first kicker primer to the sequence (F3cT) in the first strand of the target nucleic acid molecule; and (3) extending the first kicker primer from its 3' end, using a suitable polymerase, to displace the first single-stranded nucleic acid molecule.

[70] The method of any one of [45-69], wherein the reaction is at least 20% as fast, at least 30% as fast, at least 40% as fast, at least 50% as fast, at least 60% as fast, at least 70% as fast, at least 80% as fast or even at least 100% as fast as the same reaction where the first extruding primer does not comprises the first extruding sequence at its 5' terminus and/or the second extruding primer does not comprise a second extruding sequence at its 5' terminus.

[71] The method of any one of [45-70], wherein the first extruding sequence or the second extruding sequence is at least 1, 2, 3, 4, 5, 6, 7, 8, 9, 10, 12, 14, 16, 18, 20, 25, 30, 35, 40, 45, 50, 60, 70, 80, 90, 100, 150, or 200 nucleotides.

[72] The method of any one of [45-71], wherein the first extruding sequence or the second extruding sequence is 1 to 100 nucleotides, 2 to 75 nucleotides, 3 to 50 nucleotides, or 4 to 30 nucleotides in length.

[73] The method of any one of [45-72], wherein the strand displacement amplification polymerase is selected from the group consisting of Bst DNA polymerase, Bca(exo-) DNA polymerase, Klenow fragment of DNA polymerase I, Vent DNA polymerase, Vent(Exo-) DNA polymerase (exonuclease activity-free Vent DNA polymerase), DeepVent DNA polymerase, DeepVent(Exo-) DNA polymerase (exonuclease activity-free DeepVent DNA polymerase), φ29 phage DNA polymerase, MS-2 phage DNA polymerase, Z-Taq DNA polymerase (Takara Shuzo), and KOD DNA polymerase (TOYOBO).

[74] The method of any one of [45-72], wherein the strand displacement amplification polymerase is Bst DNA polymerase or Bca(exo-) DNA polymerase.

[75] The method of any one of [45-74], wherein the sample is selected from a specimen, a culture, a patient sample, a subject sample, a biological sample, and an environmental sample.

[76] The method of [75], wherein the patient sample or the subject sample is from blood, saliva, cerebral spinal fluid, pleural fluid, milk, lymph, sputum, semen, stool, swabs, Broncho Alveolar Lavage Fluid, tissue samples, or urine.

[77] The method of any one of [45-76], wherein the combining step further comprises combining with a reaction accelerator selected from the group consisting of one or more acceleration primers, an RNA polymerase promoter, a nicking sequence, and combinations thereof.

[78] The method of [77], wherein the reaction accelerator comprises the one or more acceleration primers and the acceleration primers are selected from the group consisting of kicker acceleration primers, loop acceleration primers, and stem acceleration primers.

[79] The method of [77] or [78], wherein the reaction accelerator comprises the RNA polymerase promoter and the RNA polymerase promoter is included in the first extruding primer, the second extruding primer, the kicker acceleration primer, the loop acceleration primer, or the stem acceleration primer.

[80] The method of [77], wherein the RNA polymerase promoter is a T7 RNA polymerase promoter.

[81] The method of [77], wherein the reaction accelerator comprises the nicking sequence and the nicking sequence is included in the first extruding primer, the second extruding primer, the kicker acceleration primer, the loop acceleration primer, or the stem acceleration primer.

[82] A kit comprising the set of primers of any of [31-44].

[83] The kit of [82], further comprising a strand displacement a p cation polymerase.

[84] The kit of [83], wherein the strand displacement amplification polymerase is selected from the group consisting of Bst DNA polymerase, Bca(exo-) DNA polymerase, Klenow fragment of DNA polymerase I, Vent DNA polymerase, Vent(Exo-) DNA polymerase (exonuclease activity-free Vent DNA polymerase), DeepVent DNA polymerase, DeepVent(Exo-) DNA polymerase (exonuclease activity-free DeepVent DNA polymerase), 4)29 phage DNA polymerase, MS-2 phage DNA polymerase, Z-Taq DNA polymerase (Takara Shuzo), and KOD DNA polymerase (TOYOBO).

[85] The kit of [83], wherein the strand displacement amplification polymerase is Bst DNA polymerase or Bca (exo-) DNA polymerase.

[86] The kit of any one of [82-85], further comprising a kicker acceleration primer, a loop acceleration primer, and/or a stem acceleration primer.

[87] The kit of any one of [82-86], further comprising a detection probe.

[88] The kit of [87], further comprising a universal detection probe that interacts with the detection probe during isothermal amplification.

[89] The kit of any one of [82-88], further comprising a thermostable luciferase, luciferin and an enzyme that converts inorganic pyrophosphate to ATP.

[90] An amplicon nucleic acid derived from a target nucleic acid sequence comprising from 5' to 3':

(2) a second sequence comprising a sequence (R1c);

(3) a sequence (R2), wherein the sequence (R2) hybridizes to a sequence (R2cT) in a complimentary strand of the target nucleic acid sequence;

(4) a sequence (R1T), wherein the sequence (R1T) hybridizes to the sequence (R1c);

(5) a sequence (F1cT);

(6) a sequence (F2c), wherein the sequence (F2c) hybridizes to a sequence (F2T) in the complimentary strand of the target nucleic acid sequence; and (7) a sequence (F1), wherein the sequence (F1) hybridizes to (F1cT)
wherein the nucleic acid further comprises:
- (X) (8) a first extruding sequence at the 3' terminus, wherein the first extruding sequence is at least 4 nucleotides and cannot hybridize to the template nucleic acid or its compliment, and wherein the sequence (R1c) is at the 5' terminus;
- (Y) (1) a second extruding sequence at the 5' terminus, wherein the second extruding sequence is at least 4 nucleotides and cannot hybridize to the template nucleic acid or its compliment, and wherein the sequence (F1) is at the 3' terminus; or
- (Z) (8) a first extruding sequence at the 3' terminus, wherein the first extruding sequence is at least 4 nucleotides and cannot hybridize to the template nucleic acid or its compliment, and (1) a second extruding sequence at the 5' terminus, wherein the second extruding sequence is at least 4 nucleotides and cannot hybridize to the template nucleic acid or its compliment.

I. Foldback Primers

An aspect of the invention is the use of foldback primers in the amplification reactions described herein. An amplification reaction that includes at least one pair of foldback primers is foldback amplification.

A. LAMP Primers

LAMP primers in the simplest form include two foldback primers designed to generate loops by folding back on the template (or the portion of the template within the amplicon). The forward foldback primer for LAMP includes a 5' F1 complementary sequence (F1c, FIG. 1) that anneals to the F1T sequence of the template nucleic acid sequence and a 3' F2 sequence (FIG. 1) that anneals to the F2cT sequence of the template nucleic acid sequence. The reverse foldback primer for LAMP includes a 5' R1 complementary sequence (R1c, FIG. 1) that anneals to the R1T sequence of the template nucleic acid sequence and a 3' R2 sequence (FIG. 1) that anneals to the R2cT sequence of the template nucleic acid sequence. The forward and reverse primers may include one or more nucleotides between the F1c and F2 sequences and the R1c and R2 sequences or they may overlap where they share a common sequence. The F2T and F1T sequences and the R2T and R1T sequences of the template nucleic acid sequence may have an intervening nucleic acid sequence. Preferably, the intervening sequence should not be so long that the effective local concentration of the F1c sequence and the F1T sequence or of the R1c sequence and the R1T sequence no longer results in self-annealing of the amplified nucleic acid being preferential over annealing of two separate molecules. Thus, a preferred length of the intervening sequence between the 2 T and 1 T sequences is typically between 0 and 500 nucleotides, between 5 and 250 nucleotides, or between 10 and 100 nucleotides. However, in some cases, too short of an intervening sequence may be disadvantageous for forming a self-annealing loop. Further, it is desirable that the formed loop has a structure that enables annealing of a new forward loop primer (or a loop acceleration primer where that form of acceleration is being used) and a smooth start to strand displacement complementary strand synthesis reaction. Thus, more preferably, the primers are designed such that the distance between the 2 T and 1 T sequences is between 0 and 100 nucleotides or between 10 and 70 nucleotides. The F1C sequences or R1C sequences can be substantially complementary to the 3' end downstream sequences after the 3' end is extended by a polymerase. For mutation detection, the 5' end nucleotide of F1C or R1C can be designed to not complementary to the mutation site to result in non-amplification or less degree of amplification. The same approach can be applied for methylation detection.

B. SMAP Primers

Figure 2A:
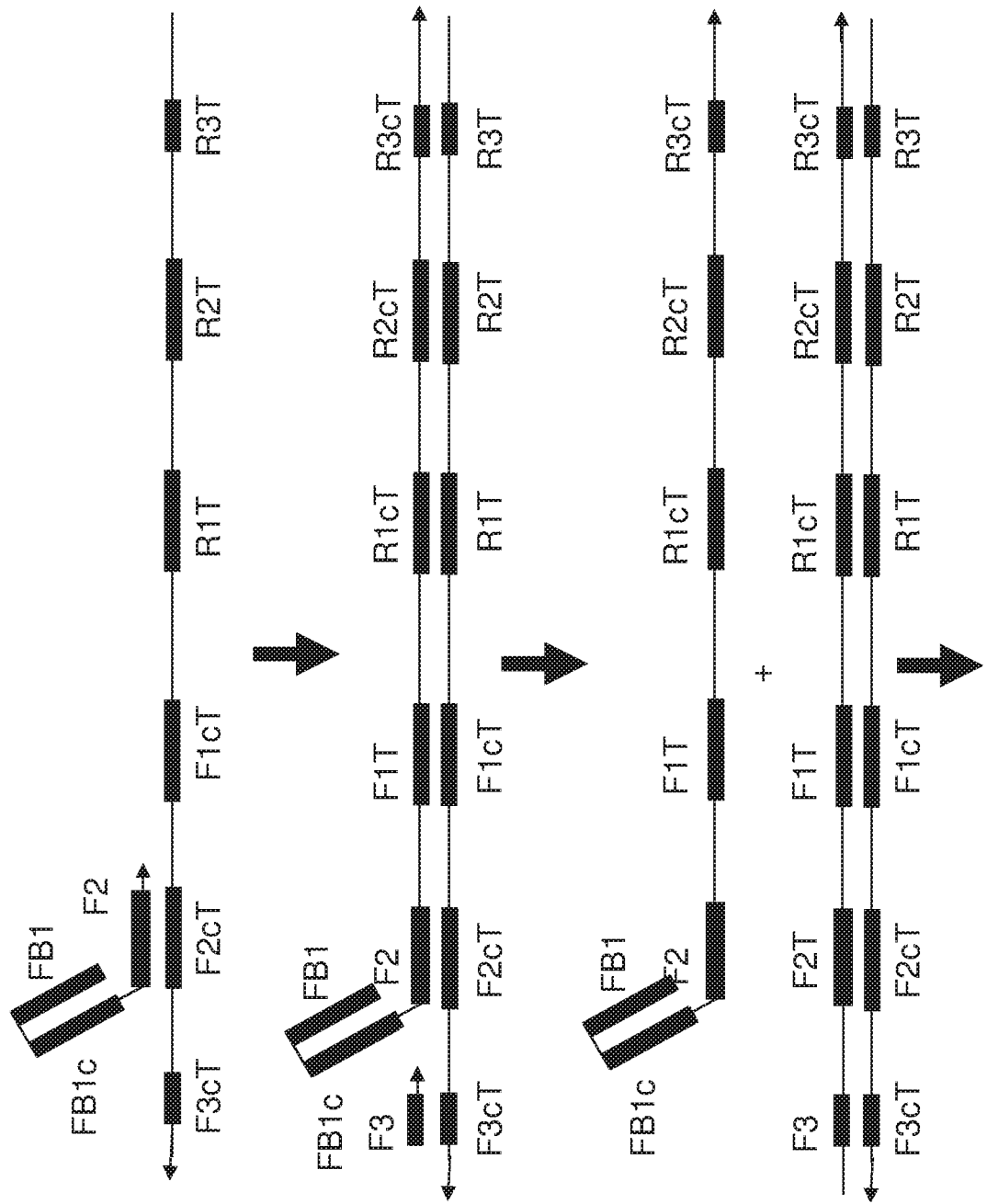
FIG. 2A and FIG. 2B show an exemplary implementation of omega amplification based upon a primer set of one extruding primer and one hairpin primer.
Figure 2B:
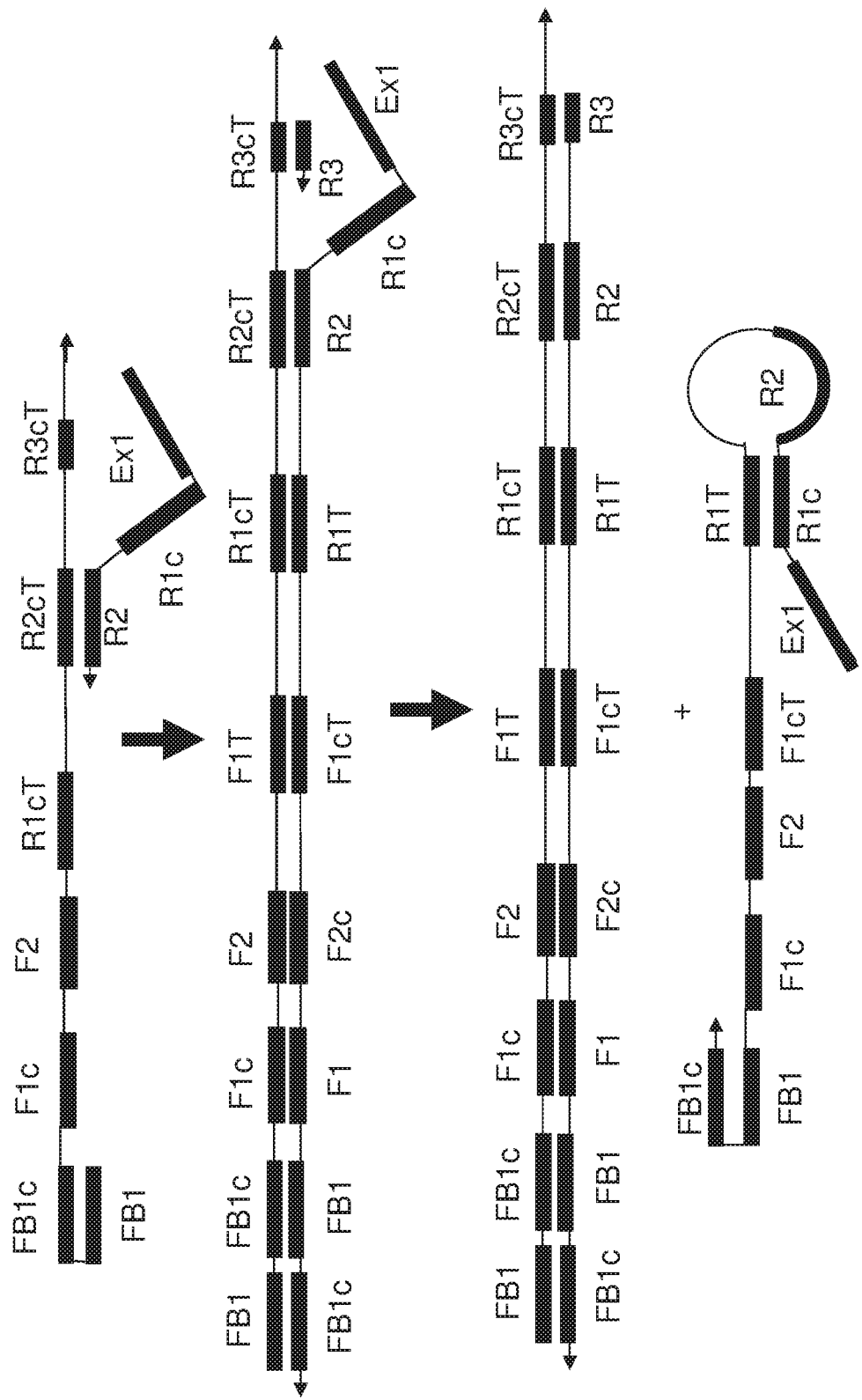

SMAP primers in the simplest form include a hairpin primer that folds back on itself and a foldback primer designed to generate loops by folding back on the template (or the portion of the template within the amplicon). The hairpin primer does not include sequences to fold onto downstream of the 3' end hairpin primer extension sequences. For convenience, the hairpin primer is referred to as the forward primer and the foldback primer is referred to as the reverse primer, but this is an arbitrary designation. The hairpin primer can be the reverse primer and the foldback primer can be the forward primer. The hairpin primer for SMAP includes a 5' FBI sequence (FIG. 2) that anneals to the FB1 complementary sequence (FB1c, FIG. 2) of the forward primer and a 3' F2 sequence (FIG. 2) that anneals to the F2cT sequence of the template nucleic acid sequence. The FB1c sequence is between the FB1 and the F2 sequences. The reverse primer for SMAP includes a 5' R1 complementary sequence (R1c, FIG. 2) that anneals to the R1T sequence of the template nucleic acid sequence and a 3' R2 sequence (FIG. 2) that anneals to the R2cT sequence of the template nucleic acid sequence. The foldback primer can include all of the features for foldback primers set out in Section I(A) above. The hairpin primer may include one or more nucleotides between the FB1c and FB1 sequences and between the FB1c and F2 sequences or they may overlap where they share a common sequence. Preferably, the intervening sequence between the FB1c and FB1 sequences should not be so long that the effective local concentration of the FB1c and FB1 sequences no longer results in self-annealing of the amplified nucleic acid being preferential over annealing of two separate molecules. Thus, a preferred length of the intervening sequence between the FB1c and FB1 sequences is typically between 0 and 500 nucleotides, between 5 and 250 nucleotides, or between 10 and 100 nucleotides. However, in some cases, too short of an intervening sequence may be disadvantageous for folding and self-annealing. Further, in some instances it is desirable that the intervening sequence between the FB1c and FB1 sequences have a structure that enables annealing of a loop acceleration primer and a smooth start to strand displacement complementary strand synthesis reaction. Thus, more preferably, the primers are designed such that the distance between the FB1c and FR1 sequences is at least 10 nucleotides, at least 15 nucleotides, at least 20 nucleotides or at least 30, at least 40 nucleotides, at least 50 nucleotides or at least 60 nucleotides in length or is between 30 and 100 nucleotides when foldback primer amplification is applied.

C. GEAR Primers

GEAR primers are subsets of SMAP primers or LAMP primers where the F1T and R1cT overlap or are one in the same (with the corresponding being true for the F1cT and R1T). The overlap between the F1T and the R1cT can be at least 1, 2, 3, 4, 5, 6, 7, 8, 9, 10, 12, 14, 16, 18, 20, 25, or 30 nucleotides or the F1T and R1cT are one in the same. Otherwise, GEAR primers can have all of the features of LAMP primers and/or SMAP primers set out in Sections I(A) and I(B), above.

D. Common Features of Annealing Portions of Primers

The foldback primers and acceleration primers all include one or more sequences that anneals to the target nucleic acid, to the amplicon nucleic acids or to both under the reaction conditions. Annealing sequences therefore will be of sufficient length and composition of nucleotides to enable such annealing with the required specificity under the amplification reaction conditions. An annealing sequence is also a priming sequence if it provides at least one free 3'—OH group that serves as the origin of strand synthesis for the strand displacement amplification polymerase. A primer will have at least one priming sequence. The minimal length of a primer recognized by known polymerases catalyzing sequence-dependent nucleic acid synthesis is around 5 nucleotides. In addition, to ensure a high probability of nucleotide-sequence specificity, it is preferred to use an annealing sequence comprising ten nucleotides or more. Thus, the annealing sequence will preferably be at least 10 nucleotides, at least 20 nucleotides, at least 30 nucleotides, at least 40 nucleotides, at least 50 nucleotides, at least 60 nucleotides, or even at least 70 nucleotides in length. On the other hand, longer nucleotide sequences are more expensive to chemically synthesize and therefore the upper limits disclosed herein are preferable. Preferably, the annealing sequences are from 5 to 200 nucleotides long, and more preferably are from 10 to 50 nucleotides long.

Thus, annealing sequences will typically be substantially complementary to the sequence to which it anneals. The term "substantially complementary" means that the annealing sequence has sufficient complementarity to anneal to the sequence on the template nucleic acid and/or amplicon nucleic acid under the amplification reaction conditions. This typically requires that the annealing sequence has at least 70%, 80%, 90%, 95%, 99% or 100% complementarity to the sequence on the template nucleic acid and/or amplicon nucleic acid under the amplification reaction conditions.

Extruding Sequences

For omega amplification, at least one of the foldback primers will include an extruding sequence at its 5' terminus. The extruding sequences can be any kinds of oligonucleotides including natural or unnatural nucleotides. The foldback primers including extruding sequences are called extruding primers. Omega amplification reactions as used herein are a subset of foldback primer amplification reactions. In some embodiments, the extruding sequence is found at one (or both ends) of an amplicon nucleic acid. The extruding sequence therefore will not provide a free '3 OH from which a complementary strand can be synthesized during the omega amplification reaction. The extruding sequence preferably will not anneal to the template nucleic acid at all or at least will not anneal to the template nucleic acid in proximity to the amplified portion of the template nucleic acid.

The extruding sequence is at least 1, 2, 3, 4, 5, 6, 7, 8, 9, 10, 12, 14, 16, 18, 20, 25, 30, 35, 40, 45, 50, 60, 70, 80, 90, 100, 150, or 200 nucleotides. The extruding sequence can be less than 500, 450, 400, 350, 300, 250, 200, 150, 100, 90, 80, 70, 60, 50, 45, 40, 35, 30, 25, or 20 nucleotides. In certain aspects, the extruding sequence can be 1 to 100 nucleotides, 2 to 75 nucleotides, 3 to 50 nucleotides, or 4 to 30 nucleotides in length. The extruding sequence can be of any sequence as long as the sequence will not provide a free '3 OH from which a complementary strand can be synthesized during the omega amplification reaction. By way of example, the extruding sequence in a forward foldback primer will not anneal to the region immediately 3' of the F1T region of the template second strand. In some embodiments, the extruding sequence comprises a G-quadruplex, a T7 promoter sequence, a nicking site, or an FQ sequence. In some embodiments, the extruding sequence will be G rich because G-rich extruding sequences can accelerate the omega amplification reactions.

II. Reaction Accelerators

In addition to the foldback primers discussed above, the amplification reactions may include one or more additional "acceleration primers" that can accelerate the rate of the amplification reaction such as kicker acceleration primers, loop acceleration primers, and stem acceleration primers. In certain embodiments, the amplification reaction may also include other accelerators that can be incorporated into one or more foldback primers and one or more acceleration primers. The acceleration primers and the other accelerators are not mutually exclusive and therefore can be used in any combination.

A. Kicker Acceleration Primers

Kicker acceleration primers are primers that have sequences that anneal to a strand of the target nucleic acid 5' of where the corresponding foldback primer anneals (e.g., F3 and R3 of the target nucleic acid). For example, the forward kicker acceleration primer will comprise an F3 sequence (FIG. 1 and FIG. 2) that anneals 5' of the forward. foldback primer which allows the strand displacement amplification polymerase to displace the newly synthesized strand incorporating the forward foldback primer. The reverse kicker acceleration primer will comprise an R3 sequence (FIG. 1 and FIG. 2) that anneals 5' of the reverse foldback primer which allows the strand displacement amplification polymerase to displace the newly synthesized strand incorporating the reverse foldback primer. Kicker acceleration primers may be simple primers that only comprise the annealing sequence F3 or R3, as applicable. In other embodiments, the kicker acceleration primers may include additional nucleotides on the 5' end such as additional sequences for detection (e.g., an RNA polymerase promoter, an FQ primer complementary sequence, a second strand comprising an FQ primer or an FQ invader, etc.)), further acceleration (e.g., an RNA polymerase promoter or a nicking sequence), or even additional sequences so that the kicker acceleration primer is an additional foldback primer to fold onto downstream of its 3' end extension sequences. In other embodiments, more than one forward kicker acceleration primers or reverse kicker acceleration primers are used to increase the speed and sensitivity of the reaction.

B. Loop Acceleration Primers

Loop acceleration primers are primers that have sequences that anneal to the loop formed when the strand of a foldback primer has been generated or when the complementary strand of a foldback primer that include a loop has been generated. For example, a forward loop acceleration primer will anneal to the template nucleic acid between F2(T) and F1T (FIG. 1). Extension and strand displacement from such a forward loop acceleration primer will allow a new forward foldback primer to anneal to the F2cT sequence of the template nucleic acid. Similarly, a reverse loop acceleration primer will anneal to the template nucleic acid between R2(T) and R1T (FIG. 1). Extension and strand displacement from such a forward loop acceleration primer will allow a new forward foldback primer to anneal to the R2cT sequence of the template nucleic acid. Loop acceleration primers may be simple primers that only comprise the annealing sequence. In other embodiments, the loop acceleration primers may include additional nucleotides on the 5' end such as additional sequences for detection (e.g., an RNA polymerase promoter, an FQ primer complementary sequence, a second strand comprising an FQ primer or an FQ invader, etc.)), further acceleration (e.g., an RNA polymerase promoter or a nicking sequence), or even additional sequences so that the loop acceleration primer is an additional foldback primer or hairpin primer.

The disclosed invention discovered that the 5' end sequence of loop primer folding onto 3' end of loop primer downstream sequences after the 3' end of loop primer is extended by polymerase can speed up the reaction and improve reaction sensitivity. The folding region can have a length of at least 5 nucleotides, at least 10 nucleotides, at least 15 nucleotides, at least 20 nucleotides, at least 30 nucleotides, at least 50 nucleotides, at least 100 nucleotides at least 200 nucleotides, at least 300 nucleotides or at least 500 nucleotides. In another embodiment, the 5' end loop primer sequences can have chemical moiety to stop polymerase extension at a specific or intended location. In a preferred format, the 5' end sequence of the loop primer is F1C sequence when the loop primer is a forward loop primer and the 5' end sequence of the loop primer is R1C sequence when the loop primer is a reverse loop primer. 5' end loop primer can have different kind of sequence. For instance, part of the loop primer has the 5' end folding sequence to speed up the reaction and part of the loop primer can have 5' end artificial sequence to carry FQ probe for detection and part of the loop primer is fully complementary to the template hybridization sequences. In a specific amplification and detection reaction, the types of 5' end sequences of loop primer used depends on specific applications and purpose. An example of foldback primer amplification for mutation detection, the 5' end loop primer can have FQ probe and the 3' end loop primer can be positioned near or overlap with the mutation site. A mismatch at 3' end loop primer will not be extended or less extended to generate detectable amount signal. In order to increase specificity, additional mismatch can be designed near its 3' end. Alternatively, near 3' end loop primer sequences can include ribonucleotides or O-methyl nucleotides. The same approach can be used for methylation detection. In curtain cases, a mixture of 5' end of loop primer sequences can be used. Example of a specific amplification might include both partial of the forward loop accelerator primer fully hybridized to template and also partial of forward loop accelerator primer including 5' end artificial sequences. 5' end of the loop primer folds onto 3' end of loop primer downstream sequences after the loop primer is extended is a new type of primer for use in foldback primer amplification reactions generally (rather than being specific to omega amplification) and are therefore an independent aspect of the disclosure.

C. Stein Acceleration Primers

U.S. Patent publication 2012/0157326 discloses stern accelerated isothermal nucleic acid amplification technology that can be used to accelerate the omega amplification and the foldback primer amplification reactions disclosed herein through use of primers which bind to the stem region, known as "stem primers" (referred to as "stem acceleration primers" herein, and the application is incorporated by reference herein for its teachings regarding stem primers and their use in accelerating isothermal amplification reactions, but not for any definitions therein). The annealing region of the stern acceleration primers preferably do not overlap with the annealing regions of the foldback primers. The region between the forward and reverse foldback primer annealing regions (e.g., F1CT and R1T or F1T and R1cT) represents a region which is guaranteed to form part of the amplicon but does not itself conventionally provide for any primer binding sites in LAMP or SMAP. This region is referred to herein as the "stem region" of the amplicon nucleic acids. The stem region can have a length of at least 5 nucleotides, at least 10 nucleotides, at least 15 nucleotides, at least 20 nucleotides, at least 30 nucleotides, at least 50 nucleotides, at least 100 nucleotides at least 200 nucleotides, at least 300 nucleotides or at least 500 nucleotides.

Stem acceleration primers may be positioned anywhere between the forward and reverse foldback primer annealing sites in the template nucleic acid provided that the annealing site(s) of the stem acceleration primer(s) do(es) not significantly overlap with the forward or reverse foldback primer annealing sites in the template nucleic acid. When one or both of the foldback primers are loop primers, the foldback primer annealing sites in the template nucleic acid are the F1T and/or the R1cT sequences, as applicable, such that the stem acceleration primers are between the R1(c)T and F1(c)T sequences when two loop primers are used.

In some aspects, only one stem acceleration primer is used which binds either the first or second strand of the template nucleic acid (or amplicon nucleic acid). in other aspects, two or more stem acceleration primers may be used which can bind either to different strands of the template nucleic acid (or amplicon nucleic acid) or to the same strand. The stem acceleration primer methods may be practiced with one, two, three, four or more stem acceleration primers which can be used in any spatial combination and which may bind either the first or second strand provided that the annealing sites for the stem acceleration primers do not significantly overlap with the forward or reverse foldback primer annealing regions or do not overlap at all. The stem acceleration primers may further anneal to any part within the stem region of the target nucleic acid. Thus, the stem acceleration primer(s) may have an annealing site which is in close proximity to the forward or reverse foldback primer annealing regions. "Close proximity" means that the annealing region of the stern acceleration primer and the foldback primer annealing region are less than 10, 50, 100, 200, 300, 400, 500, 600, 700, 800, 900 or 1000 nucleotides apart.

The stern acceleration primers may be at least 5 nucleotides, at least 10 nucleotides, at least 20 nucleotides, at least 30 nucleotides, at least 40 nucleotides, at least 50 nucleotides, at least 60 nucleotides, at least 70 nucleotides, at least 80 nucleotides or at least 90 nucleotides in length.

The stem acceleration primers may be simple primers. However, the stem acceleration primers that may include additional sequences for detection (e.g., an RNA polymerase promoter, an FQ primer complementary sequence, a second strand comprising an FQ primer or an FQ invader, etc.)), further acceleration (e.g., an RNA polymerase promoter or a nicking sequence), or even additional sequences so that the loop acceleration primer is an additional folding primer or loop primer. Where more than one stem acceleration primer is used, the stem acceleration primers may be of the same kind or may be a combination of different kinds of primers (e.g., all simple primers, all detection primers, one simple primer and one acceleration primer, etc.).

D. RNA Polymerase Promoters

The amplification reactions herein can also be accelerated by combining with other isothermal amplification techniques that are dependent on transcription as part of the amplification process, for example Nucleic Acid Sequence Based Amplification (NASBA; U.S. Pat. No. 5,409,818, which is incorporated herein for its disclosure on NASBA, but not for definitions that conflict with terms and their use herein) and Transcription Mediated Amplification (TMA; U.S. Pat. No. 5,399,491, which is incorporated herein for its disclosure on TMA, but not for definitions that conflict with terms and their use herein).

The RNA polymerase promoters can be included in any of the primers including: one or more of the extruding primers, one or more of the foldback primers, one or more of the loop acceleration amplification primers, one or more of the kicker amplification primers, one or more of the stem amplification primers, or combinations thereof. In preferred embodiments, the RNA polymerase promoter is included in the extruding sequence on one or more extruding primers. The functional RNA polymerase promoter is generated when the strand complementary to the primer has been synthesized. The RNA polymerase then binds to the double stranded promoter and generates RNA that can be detected. In preferred embodiments, the RNA promoter is the T7 promoter and the RNA polymerase is a thermostable T7 RNA polymerase. In order to carry out RNA polymerase acceleration with the amplification reactions disclosed herein, the reaction will include the strand displacement amplification polymerase and an RNA polymerase which catalyze the strand displacement complementary strand synthesis reaction. Alternatively, the amplification reaction can be configured to further copy the RNA strand to create more amplicons to amplify. To further accelerate the amplification reaction, a polymerase with reverse transcriptase activity can be used to create RNA-DNA hybrids for further amplification. In preferred embodiments, the strand displacement amplification polymerase will have reverse transcriptase activity.

E. Nicking Amplification

The amplification reactions herein can additionally be accelerated by combining with other isothermal amplification techniques that are dependent on strand nicking as part of the amplification process, for example Nicking and Extension Amplification Reaction for the exponential amplification of nucleic acids (NEAR; U.S. Pat. Pub. 2009/0081670, which is incorporated herein for its disclosure on NEAR, but not for definitions that conflict with terms and their use herein). The nicking sequence can be included in any of the primers including: one or more of the extruding primers, one or more of the foldback primers, one or more of the loop acceleration primers, one or more of the kicker acceleration primers, one or more of the stem acceleration primers, or combinations thereof. Once the complementary strand of primer's strand has been generated, the nicking sequence will be created. The nicking enzyme can then nick the double stranded nucleic acid to produce a 3' OH from which the strand displacement amplification polymerase can extend. In some embodiments, the nicking enzyme will be able to continue to nick each new strand extended by the strand displacement amplification polymerase to continue to accelerate the amplification reaction.

F. Chemicals

Certain chemicals when added to the omega amplification reaction can accelerate the reaction significantly. The addition of the at least one bland magnesium chelator to the reaction mixture for nucleic acid amplification may, in some cases, speed up the amplification reactions. The bland magnesium chelator is preferably selected from among: sodium citrate, acetic acid, ADP, aspartic acid, ATP, n-butyric acid, citric acid, cysteine, 3,4-dihydroxybenzoic acid, O,O-dimethylpurpurogallin, EDTA, EGTA, gluconic acid, glutamic acid, glutaric acid, glyceric acid, glycine, glycolic acid, glycylglycine, guanosine, B-hydroxybutyric acid, inosine triphosphate, lactic acid, malic acid, NTA, oxalic acid, polyphosphate, propionic acid, purine, salicylaldehyde, salicylic acid, succinic acid, tartaric acid, tetrametaphosphate, ttimetaphosphate, triphosphate, uridine diphosphate. Preferably the bland magnesium chelator is used in a concentration varying from 0.5 to 2 mM, more preferably from 0.8 to 1.2 mM. The bland magnesium chelator particularly preferred for the aims of the present invention is sodium citrate.

III. Methods of Amplification

The amplification reactions described herein are generally isothermal amplification methods, which means that the amplification reaction does not require a change in the reaction temperature as is required in conventional PCR amplification reactions.

The skilled person will be aware that, in addition to the primers needed for amplification, the amplification reactions often will require further reagents in order to generate the amplicon nucleic acids. One of skill in the art will readily be able to determine the additional reagents (which generally include a suitable buffer, dNTPs, a strand displacement amplification polymerase, etc.).

One of skill in the art will further appreciate that it is also necessary to provide suitable conditions for the generation of the amplicon nucleic acids. This can be achieved by providing a suitable incubation temperature, for example. It is preferred that amplification occurs under isothermal conditions. This means that during amplification the temperature is kept constant. "Constant" means that the temperature varies by no more than ±10° C., preferably no more than ±5° C. However, the amplification reactions also include methods that encompass a single temperature change of greater than 10° C., two temperature changes of greater than 10° C., three temperature changes greater than 10° C., four temperature changes greater than 10° C. or five temperature changes greater than 10° C. during the amplification process.

Preferably, the amplification reactions disclosed herein (including in preferred embodiments of the detection methods) are performed in a sealed vessel. This is of great utility since it reduces or even eliminates the possibility of the sample becoming contaminated. Moreover, it reduces or even eliminates the possibility of the laboratory becoming contaminated. This is particularly important as if even one copy of the template nucleic acid or amplicon nucleic acid were to escape into the laboratory, this could potentially contaminate other samples to be tested and give false-positive results. Thus, the ability to prevent contamination is of particular importance where a method of the invention is used in a diagnostic application.

A. Strand Displacement Amplification Polymerases

The polymerases for use in the amplification reactions disclosed herein are strand displacing polymerases. Many such polymerases are known in the art. Exemplary DNA polymerases include: Bst DNA polymerase, Bca(exo-) DNA polymerase, Klenow fragment of DNA polymerase I, Vent DNA polymerase, Vent(Exo-) DNA polymerase (exonuclease activity-free Vent DNA polymerase), DeepVent DNA polymerase, DeepVent(Exo-) DNA polymerase (exonuclease activity-free DeepVent DNA polymerase), φ29 phage DNA polymerase, MS-2 phage DNA polymerase, Z-Taq DNA polymerase (Takara Shuzo), and KOD DNA polymerase (TOYOBO). In addition, various mutants of these enzymes can be used in the amplification reactions disclosed herein, so long as they have the activity of sequence-dependent complementary strand synthesis and the strand displacement activity. Such mutants include truncated enzymes having only the structures with the catalytic activity or mutant enzymes whose catalytic activity, stability, or thermal. stability has been modified by amino acid mutations, and such.

Among these enzymes, Bst DNA polymerase and Bca (exo-) DNA polymerase are particularly preferred, because they have a high degree of thermal stability and high catalytic activity. Since the amplification reactions often require some heating, the use of thermostable enzymes is preferred. The reaction can be achieved under a wide variety of conditions using thermostable enzymes. For example, Vent(Exo-) DNA polymerase is a highly thermostable enzyme that has strand displacement activity. It has been reported that the addition of a single strand-binding protein accelerates the reaction of strand displacement complementary strand synthesis by DNA polymerase (Paul M. Lizardi et al., *Nature Genetics* 19, 225-232, July 1998). When used in the amplification reactions, acceleration of complementary strand synthesis is expected by the addition of single strand-binding protein. When Vent(Exo-) DNA polymerase is used, T4 gene 32 is effective as the single strand-binding protein.

In certain embodiments, the strand displacement amplification polymerase concentration may be varied to influence the rate of the amplification reaction and, thus decrease the time needed for detection of the production of the amplicon nucleic acid. For example, in one embodiment, the strand displacement amplification polymerase concentration may be greater than or equal to about 8 U, greater than or equal to about 16 U, greater than or equal to about 24 U, or greater than or equal to about 32 U.

B. Reaction Conditions

The amplification reactions disclosed herein are typically carried out in the presence of buffer, providing a pH suitable for the polymerase reaction. In addition, amplification reactions disclosed herein can also include: salts required for annealing of the various primers and for maintaining the activity of the polymerase (and other optional enzymes), preservatives for the maintaining the polymerase (and other optional enzymes), and, if desired, a melting temperature ($T_m$) regulator. Examples of salts that can be included to maintain the polymerase activity and to modulate the melting temperature ($T_m$) of nucleic acids include KCl, NaCl, $(NH_4)_2SO_4$, etc. The preservatives that may be used to maintain the polymerase activity include for example serum albumins such as BSA and sugars such as sucrose, glycerol, etc.

Further, typical melting temperature ($T_m$) modulators include betaine, proline, dimethylsulfoxide (hereinafter abbreviated as DMSO), formamide, and trimethylamine-N-oxide (TMANO). When a melting temperature ($T_m$) modulator is used, annealing of the primers described herein can be regulated within a limited temperature range. Moreover, betaine (N,N,N-trimethylglycine) and tetraalkylammonium salts effectively contribute to the improvement of the efficiency of strand displacement due to its isostabilizing action by eliminating the melting temperature difference between GC rich and AT rich nucleic acids. The addition of betaine, at a concentration of about 0.2 to about 3.0 M, preferably about 0.5 to about 1.5 M, to the reaction can enhance the amplification reactions disclosed herein. Since these melting temperature modulators decrease the melting temperature, a condition giving desired stringency and reactivity is empirically chosen by considering reaction conditions, such as salt concentration and reaction temperature.

Temperature conditions suitable for enzyme reactions can be readily chosen by utilizing a $T_m$ regulator. $T_m$ varies, depending on the relation of the primer and target nucleotide sequence. Thus, it is preferable to adjust the amount of a $T_m$ regulator so that the conditions that maintain the enzyme activity are consistent with the incubation conditions that meet the criterion of the present invention. Based on the disclosure of the present invention, those skilled in the art can readily choose proper amounts of a $T_m$ regulator to be added, depending on the primer nucleotide sequence. For example, $T_m$ can be determined based on the length of the annealing nucleotide sequence, the GC content, the salt concentration, and the concentration of the $T_m$ regulator.

IV. Detection Methods

The generation of amplicon nucleic acids in the amplification reactions disclosed herein may be detected by methods known to those of skill in the art. Suitable methods include but are not limited to the use of fluorescent intercalating dyes, fluorescent primers or probes, measuring turbidity, electrochemical probes, bioluminescent signals and chemiluminescent probes.

The amplification of the target nucleic acid may be detected using real-time methods, i.e., methods that can detect the template nucleic acid and/or the amplicon nucleic acids as they are amplified. Examples of such detection systems include, but are not limited to, fluorescence (e.g., fluorescent probes that are added during the amplification reaction such as described more fully below), bioluminescent signals and electrochemical probes. Other suitable reporter systems are readily available to one of ordinary skill in the art. Alternatively, the amplification product may be detected using end-point measurements, i.e., measurements which take place after the amplification of the template nucleic acid and/or amplicon nucleic acids has been completed.

The amplification of the template nucleic acid and/or amplicon nucleic acids can also be detected by other detection methods employed in other nucleic acid amplification systems. Suitable examples include, but are not limited to, FISH, sequence, gene arrays, lateral flow strips, electrophoresis, mass spectroscopy and acoustic detection.

Further, the primers used in the present invention can be labeled with known labeling substances. Such labeling substances include ligands with binding capacity, such as digoxin and biotin; enzymes; fluorescent substances; luminescent substances; and radioisotopes. In addition, techniques are known for converting nucleotides in the primers to fluorescent analogues (WO 95/05391; Proc. Natl. Acad. Sci. USA, 91, 6644-6648, 1994).

Further, any of the primers used in the amplification reactions can be immobilized on a solid phase. Alternatively, an arbitrary portion of the primers may be labeled with a ligand that has binding capacity, such as biotin, and then can be indirectly immobilized via a binding partner, such as immobilized avidin. When an immobilized primer is used as the synthesis origin, the synthesized nucleic acid product can be immobilized on a solid phase, and thus can be readily separated. The separated product may be detected by nucleic acid-specific indicators or by further hybridizing a labeled probe. Alternatively, a nucleic acid fragment of interest can be recovered by digesting the nucleic acid with an arbitrary restriction enzyme.

A. FQ Probe

The detection method in current invention is based on interaction between the universal detection probe and specific detection probe. The universal detection probe is actually an artificial sequence. The term "universal detection probes" as used herein refers to oligonucleotides that will interact with specific probe sequences directly or indirectly. The universal detection probes can be single stranded or double stranded oligonucleotides. These oligonucleotides can include natural or un-natural nucleotides. The universal detection probe can have secondary structures such as stem loop hairpin structures. The universal detection probes can include one or more than one oligonucleotides. The specific detection probe can initiate sequential interaction amount these universal detection probes if more than one universal detection probes included in order to generate detectable amplification signal. The interaction between specific probe sequence and universal detection probes can be polymerase dependent or independent to polymerase activity. When polymerase involves the interaction between specific probe sequences and universal detection probes, both specific probe sequences and universal detection probe can be used either as a primer or a template. A typical universal detection probe may includes four basic components—a universal primer (FQ invader kicker), a trigger (FQ invader, a part of specific detection probe or complement of the specific detection probe), a spine sequence (the second strand FQ probe), and a spine cover (the first strand of the FQ probe). A trigger refers to an oligonucleotides that can interact with the spine and initiate a cascade of signal amplification and detection reactions. The trigger can be part of the specific detection probe or reverse complementary sequence of the specific detection probe, or it can be any sequence generated or released during amplification. The spine is an oligonucleotides containing complementary sequence of the FQ invader kicker, the FQ invader, and the spine cover (the first strand of the FQ probe). A spine cover is hybridized with spine and prevents the FQ invader kicker from being extended when the trigger is not hybridized with spine. When the trigger is available, it hybridizes with the spine, separates the spine cover form the spine, and allows the FQ invader kicker to hybridize with the spine and to get extended by a DNA polymerase with strand displacement activity. In turn, the trigger gets displaced and hybridizes with another un-reacted spine. Some formats may combine two of the basic components in a single oligonucleotides via a stem loop structure. For instance, the spine its self has hairpin loop structure at its' 3' end. But the 3' end is flipped with a few nucleotides to stop the 3' end extension. In this case, a single stranded hairpin oligonucleotides contains both spine and spine cover. Its 3' end can be dye labeled and fluorescent intensity change can be used to monitor the amplification. In another embodiment, the 3' end of spine has a folding sequence, but cannot fold onto the spine due to spine cover. Upon FQ invader to hybridize to the spine to kick off the spine cover, the 3'end spine will fold onto spine to extend to replace the FQ invader probe. In another embodiment, spine cover is hybridized at the 5' end of spine. During amplification reaction, the 3' end of spine will use FQ invader as a template to extend. The extended spine will fold onto itself to be further extended to replace 5' end spine cover. Some formats of the universal detection probe may already have one or more than one inactivated triggers hybridized with its complementary sequence as part of the spine or as a separate oligonucleotides in order to exponentially amplify fluorescent signal. In one embodiment, a spine may contain more than one spine covers. Some formats of the universal detection probe may carry the fluorophore and quencher on spine and spine cover, or vise versa, whereas other formats may carry fluorophore and quencher in the FQ invader kicker, or a separate universal FQ probe is provided to generate fluorescent signal. Some formats may only carry fluorophore without a quencher in the system, and use intercalating dye as a fluorescence quencher (patent pub. NO.: US 2012/0282617 A1).

The invader kicker is artificial sequence that allows to incorporate full or partial of aptamer sequence into spine. There are many kinds of apatmer sequences available in literatures, such as thrombin aptamer, ATP aptamer, etc. One example of the partial aptamer is G-quadruplex sequences. For instance, the invader kicker may contain partial of G-quadruplex sequences. A full G-quadruplex sequence is formed when the invader kicker is extended with the spin as template. The extended invader kicker will form stable G-quadruplex structure to allow another invader kicker to hybridize to spine to generate exponential amplification. The invader kicker can include artificial sequence at its 5' end. The artificial sequence may include natural or unnatural nucleotides as needed. In another embodiment, in order to prevent invader kicker to interact with the spine and spine cover before FQ invader to trigger the amplification, the 3' end of the invader kicker may include mismatch when it is hybridized to the spine. The mismatch may be at its 3' end or near 3' end. In another embodiment, the newly synthesized double stranded spine from invader kicker can interact with another FQ probe to generate exponential amplification. In another embodiment, the spine may contain chemical moiety to stop polymerase extension.

In another embodiment, invader kicker has a hairpin structure with 5' end fluorescent dye labeled. The reaction system will include intercalating dye to quench the invader kicker fluorescence before it is hybridized with spine. Upon it is hybridized with the spine due to FQ invade to trigger the reaction, 5' end of invader kicker will be single stranded and the 5' end. fluorescent dye will not be quenched by intercalating dye. The changed fluorescent intensity can be used to monitor the amplification.

A preferred detection method for the amplification reactions disclosed herein includes FQ probes. An "FQ probe" is a nucleic acid that includes a fluorophore and a quencher that become sufficiently separated during the amplification reaction and/or the detection method that the fluorophore will fluoresce. An exemplary form of FQ probes is disclosed in U.S. Patent Publ. 2013/0171643, The FQ probes are typically double stranded nucleic acids where the fluorophore is on one strand and the quencher is on the other strand. The FQ probes will typically include a single stranded region for annealing. During the amplification reaction, the strand displacing polymerase will separate the two strands of the FQ probes permitting the fluorophore to fluoresce. In preferred embodiments any of the following may comprise FQ probes: one or both foldback primers, one or more stem acceleration primers, or one or more loop acceleration primers. In particularly preferred embodiments, one or more of the extruding sequences will comprise an FQ probe.

In certain aspects, the FQ probe will be a universal probe. A "universal FQ probe" will not itself anneal to the template nucleic acid, but rather will anneal to an arbitrary sequence included in one or more of the primers involved in the foldback primer amplification reaction including: one or more foldback primers, one or more stem acceleration primers, one or more loop acceleration primers, one or more kicker acceleration primers, or combinations thereof. The universal FQ probes are a new type of probe for use in foldback primer amplification reactions generally (rather than being specific to omega amplification) and are therefore an independent aspect of the disclosure. Because the universal FQ probes do not anneal to the template nucleic acid, the universal FQ probes can be re-used in many different, unrelated amplification reactions simply by including the arbitrary annealing sequence in one of the primers included in the reaction.

Figure 3:
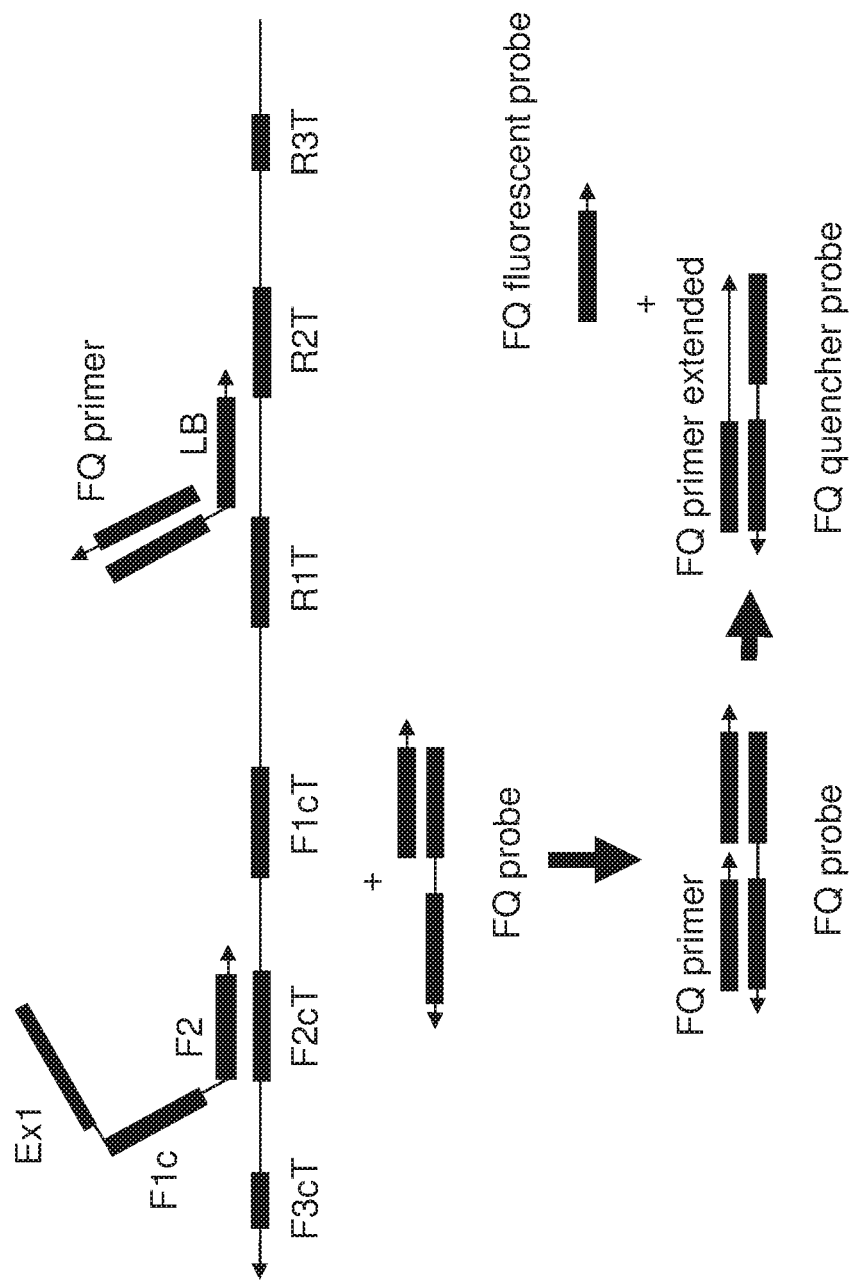
FIG. 3 shows an exemplary implementation of a detection method in omega amplification using a universal fluorescent FQ probe and a loop primer as a specific detection probe. During omega amplification reaction, the complement of the loop primer will be replaced and then hybridize with the universal FQ probe to be extended to kick of the quencher to generate fluorescent signal.
Figure 4:
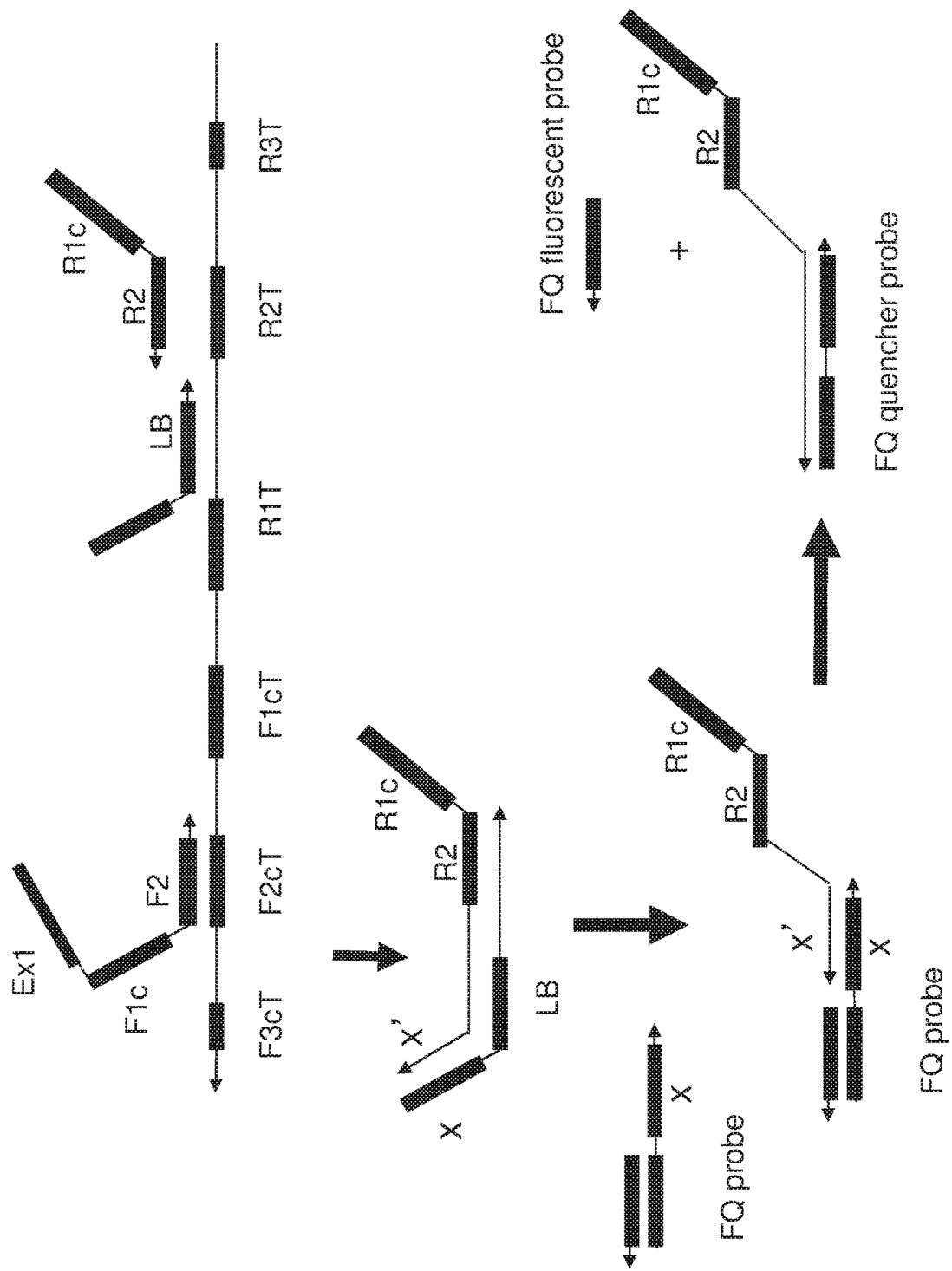
FIG. 4 shows an exemplary implementation of a detection method in omega amplification using a universal fluorescent FQ probe and a loop primer as a specific detection probe. During the amplification reaction, the newly synthesized complement of the loop primer will hybridize with the universal FQ probe to be extended to kick of the quencher to generate fluorescent signal.
Figure 5:
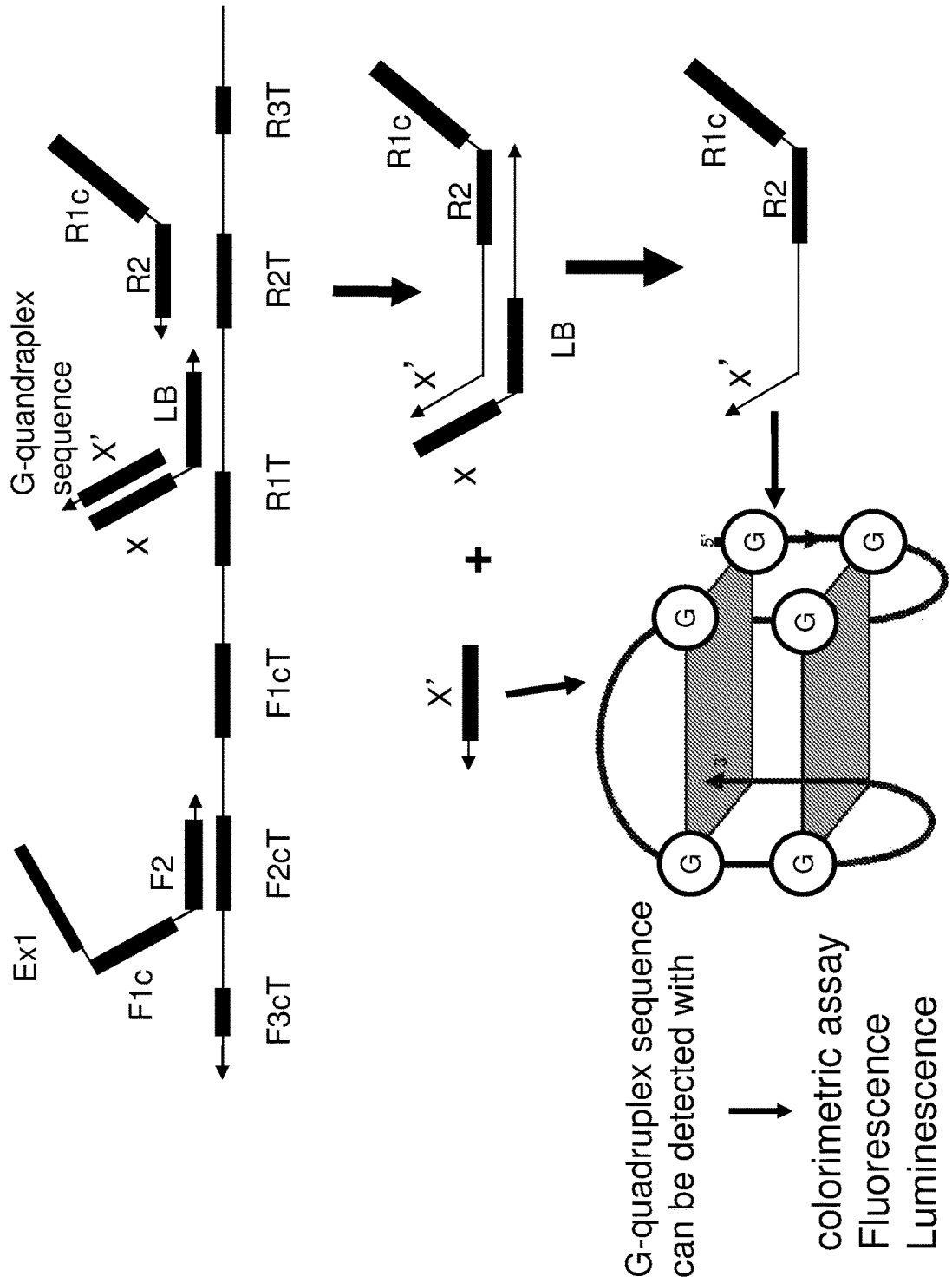
FIG. 5 shows an exemplary implementation of a detection method in omega amplification using loop primer as a detection probe. The complement of the loop primer contains G-quadruplex sequence. During the omega amplification reaction, the complement of the loop primer will be replaced to form a G-quadruplex structure which can interact with all kinds of ligands to generate detection signal.
Figure 6:
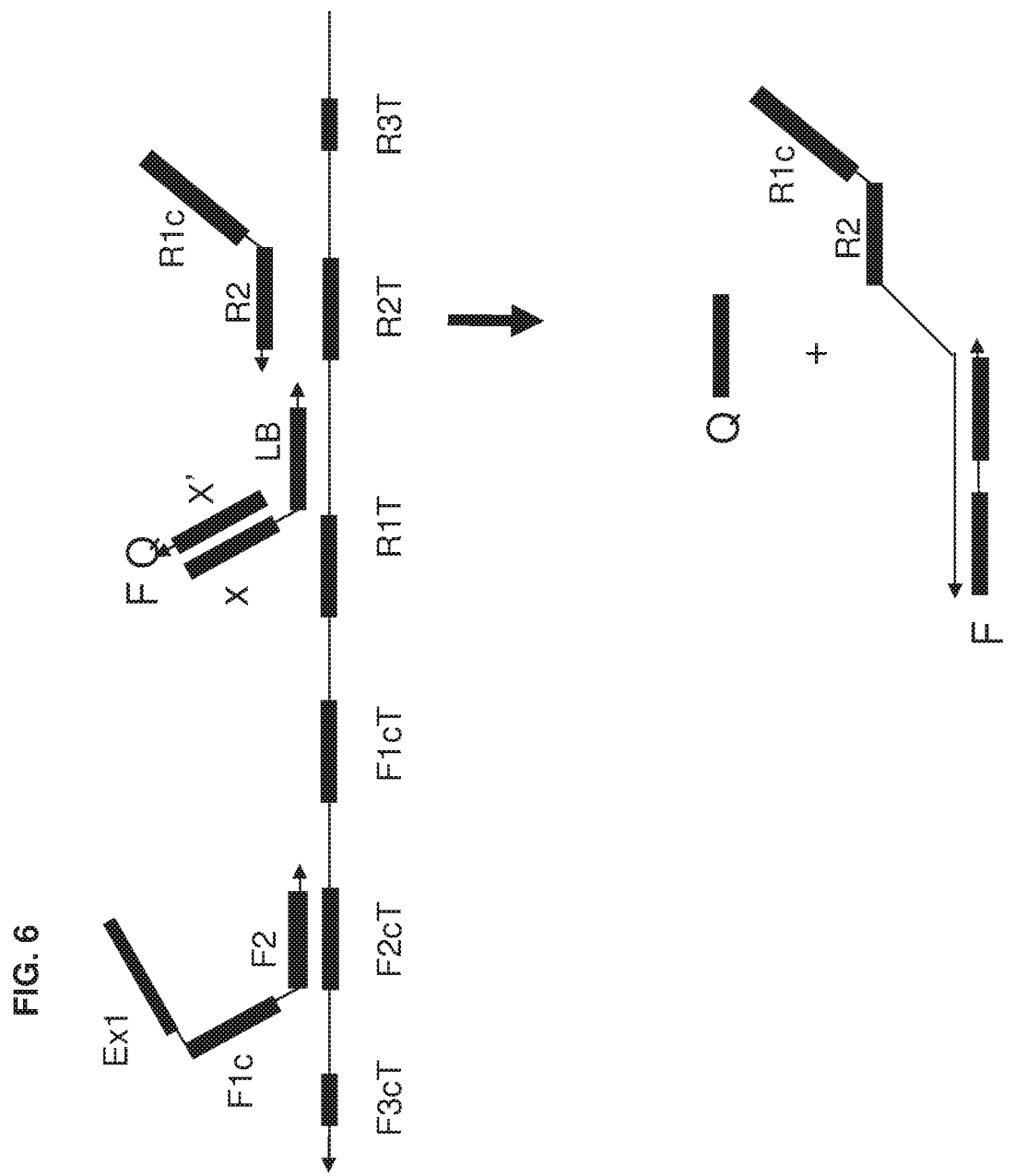
FIG. 6 shows an exemplary implementation of a detection method in omega amplification using loop primer as universal FQ probe.

The universal FQ probes will generally be activated in one of two ways. First, an "FQ invader" behavior as a primer that will anneal to the universal FQ probe, preferably to a single stranded portion of the universal FQ probe. The strand displacement amplification polymerase will then use FQ invader as a primer to extend and displace the double stranded portion of the universal FQ probe so that the fluorophore is separated from the quencher so that the fluorophore fluoresces. The FQ invader can be included as a second strand of any of the primers used for foldback amplification including, without limitation: one or more foldback primers, one or more stem acceleration primers, or one or more loop acceleration primers, or combinations thereof. During amplification, the FQ invader will then be displaced by the strand displacement amplification polymerase when the primer's complementary strand is synthesized. Upon displacement, the FQ invader can then anneal to the universal FQ probe to be used a primer to activate the universal FQ probe. Alternatively, the complementary sequence of the FQ invader can be included in one or more of the primers so that the FQ invader will be generated by the strand displacement amplification polymerase when the primer's complementary strand is generated. Upon subsequent displacement the newly synthesized FQ invader will be able to anneal to the universal FQ probe. In preferred embodiments, the FQ invader is annealed to one or more extruding sequences or the extruding sequence is single stranded but includes the complementary sequence of the FQ invader. FIG. 3 provides an exemplary implementation of a universal FQ probe and an FQ invader that is annealed to a loop acceleration primer. In such case, FQ invader is a primer and the universal FQ probe is its template for extension.

Figure 7:
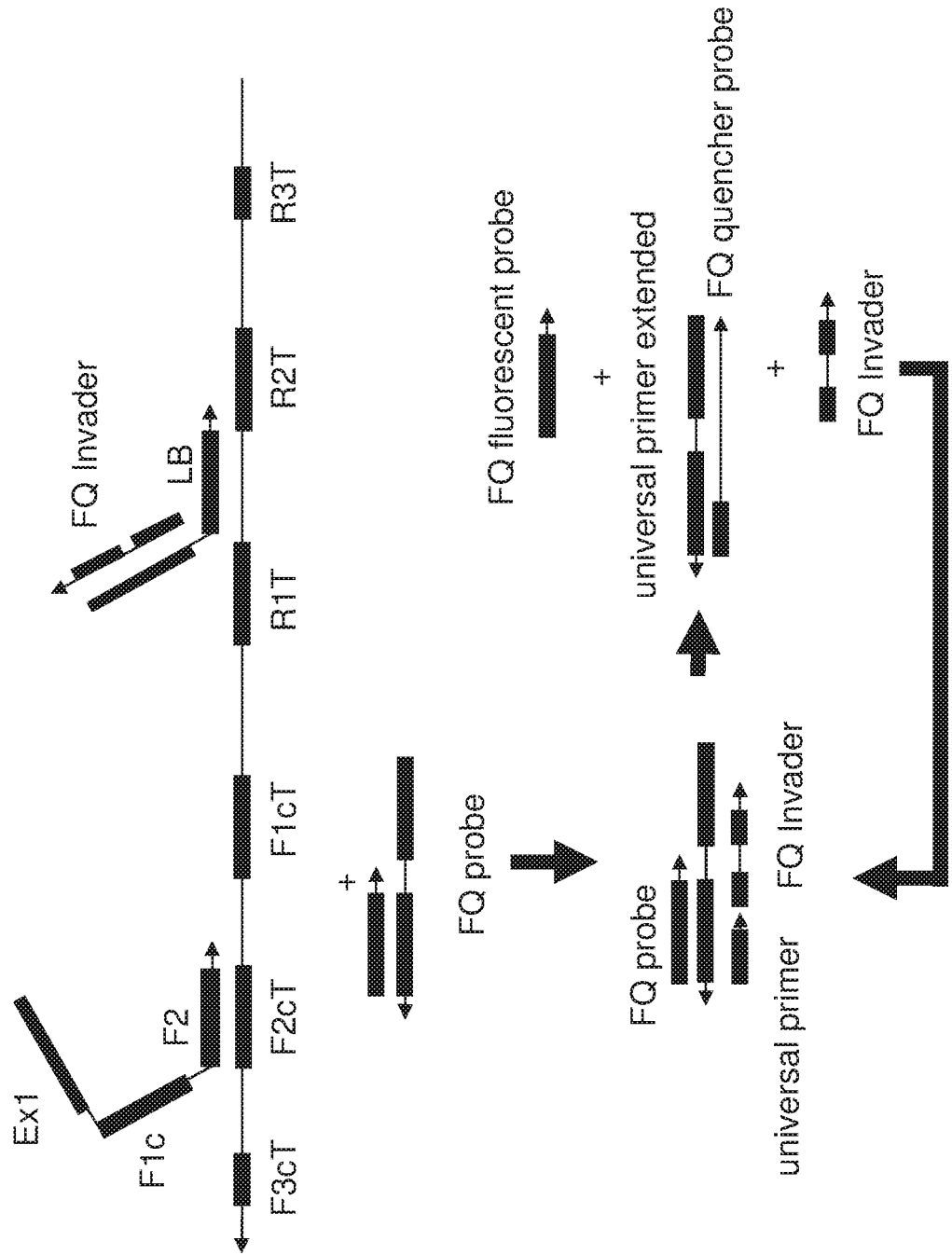
FIG. 7 shows an exemplary implementation of a detection method in omega amplification using a universal FQ probe and a loop primer LB as a specific detection probe. The complement of loop primer is a FQ invader linked at 5' end of loop primer with C3 linker. During omega amplification reaction, the replaced. FQ invader will hybridize with the universal FQ probe to kick off spine cover to generate fluorescent signal. Once the spine cover is off, the invader kicker can hybridize with spine to be extended by a polymerase to displace the FQ invader. The displaced FQ invader can hybridize with another universal FQ probe to cycle fluorescent signal amplification.

Second, an "FQ invader" behavior as a probe in toehold replacement reaction that will anneal to both a single stranded portion of the universal FQ probe and to a double stranded portion of the universal FQ probe. The FQ invader will first anneal to the single stranded portion of the universal FQ probe and then will displace the second strand of the universal FQ probe where the FQ invader overlaps with the double stranded portion of the universal FQ probe. Displacing the second strand of the universal FQ probe from the universal FQ probe will separate the fluorophore from the quencher so that the fluorophore will fluoresce. In a preferred embodiment, an "FQ invader kicker" will anneal to a double stranded portion of the universal FQ probe on the same strand 5' of where the FQ invader anneals. Therefore, when the FQ invader anneals and displaces the second strand of the universal FQ probe, the invader kicker will be able to anneal and provide a free 3' OH group for the strand displacement amplification polymerase to extend. Extension by the strand displacement amplification polymerase will displace the FQ invader allowing it to anneal to another universal FQ probe that has not been activated. Thus, a single FQ invader will be able to activate multiple universal FQ probes thereby further amplifying the signal. FIG. 7 provides an exemplary implementation of a universal FQ probe and an FQ invader that is annealed to a loop acceleration primer. FIG. 7 further illustrates the use of an invader kicker to displace the FQ invader so that it can continue to activate universal FQ probes in a signal amplification cycle.

Examples of the quencher may include, but are not limited to, DABCYL, TAMPA., and the Black Hole Quenchers (BHQ) (Biosearch Technologies, Novato, Calif.). Examples of the fluorophore may include, but are not limited to, fluorescein, cy3, cy5, and any number of quantum dots as known in the art. When the two strands of the FQ probe anneal, the fluorophore and the quencher are sufficiently close so that the fluorophore will not effectively fluoresce.

In certain embodiments, the ratio of the fluorophore containing strand to the quencher containing strand may be selected to be less than about 1:1 (e.g., higher concentrations of the quencher containing strand than fluorophore containing strand). Examples of such ratios may include, but are not limited to, less than about 1:1.1, less than about 1:1.2, less than about 1:1.3, less than about 1:1.4, less than about 1:1.5, less than about 1:1.6, less than about 1:1.7, less than about 1:1.8, less than about 1:1.9, and smaller. Examples of such ratios may further include, but are not limited to, less than about 1:2, less than about 1:3, less than about 1:4, less than about 1:5 and smaller. Higher ratios have been found to reduce the degree to which the presence of the universal FQ probe when incorporated into one of the primers inhibits the rate of the amplification reaction disclosed herein and reduce the degree of background fluorescence confounding detection.

In further embodiments, the manner of mixing the two strands of the FQ probe when incorporated into one of the primers into the amplification reaction mixture may be varied to increase the speed of the amplification reaction and, thus reducing the time needed to generate an amount of amplicon nucleic acid sufficient for detection. The fluorophore containing strand and the quencher containing strand may be in an unannealed state with respect to each other when added to the amplification reactions disclosed herein. In certain embodiments, the fluorophore containing strand to the quencher containing strand may be added to the amplification reactions disclosed herein concurrently with one another or at different times.

It was previously observed that adding the fluorophore containing strand and the quencher containing strand directly to a LAMP reaction mixture individually, as opposed to adding a double-stranded FQ probe to a LAMP reaction mixture, the LAMP reaction rate was relatively uninhibited, resulting in faster indication of a positive reaction (see, e.g., Example 5 of US Patent Publ. 2013/0171643).

The total amount of the FQ probe within the amplification reaction may also be varied to influence the speed of the amplification reaction and the onset of observable fluorescence. The detection time may be significantly reduced by using less amounts of the fluorescent and quencher probe strands that are added to the amplification reaction. For example, the amount of fluorescence probe strand added to the amplification reaction may be greater than about 0.08 µM, greater than or equal to about 0.4 µM, greater than or equal to about 1.6 µM, etc. and respective concentrations of the quencher probes may be greater than or equal to about 0.16 µM, greater than or equal to about 1.6 µM, etc.

In further embodiments, the ratio of fluorescent probe strand to the quencher probe strand may be less than about 1:1. Examples of such ratios may include, but are not limited to, less than less than about 1:1,5, less than about 1:2, less than about 1:2.5, less than about 1:3, less than about 1:3.5, less than about 1:1.4, less than about 1:1.4.5 less than about 1:5, less than about 1:5.5, less than about 1:1.60, less than about 1:1.65, less than about 1:1.70, less than about 1:1.75, less than about 1:1.80, less than about 1:8.5 less than about 1:9, less than about 1:9.5, and smaller. Examples of such ratios may further include, but are not limited to, about 1:2, about 1:3, about 1:4, about 1:5 and smaller.

In certain embodiments, the amount of the fluorescent probe strand and the quencher probe strand may be kept as low as possible while still providing detectable levels of fluorescence when positive amplification of the template nucleic acid by the amplification reaction takes place. In this manner, detection may still be performed while substantially eliminating reduction in the amplification reaction rate due to the presence of the universal FQ probe. In certain embodiments, the amount of the fluorescent probe strand may be within the range between about 0.01 to about 0.4 µM. In further embodiments, the amount of the quencher probe may selected be within the range between about 0.02 to about 0.8 µM. In other embodiments, the total amount of the universal FQ probe may be within the range between about 0.03 µM to about 1.2 µM.

B. Molecular Beacon

In certain aspects, molecular beacon sequences are used for detection of amplification of the target nucleic acid and/or the amplicon nucleic acid. Nucleic acids in beacon configurations are extensively used as specific DNA sensing matrices. The specific linkage of photoactive chromophores/quenchers to the hairpin termini results in chromophore luminescence quenching. The subsequent lighting-up of the chromophore luminescence by the hybridization of the analyzed DNA hairpins and the beacons opening was used as a general motif for the photonic detection of DNA (Tyagi, S.; Kramer, F. R. *Nat. Biotechnol.* 1996, 14, 303-308. (b) Tyagi, S.; Marras, S. A. E.; Kramer, F. R. *Nat. Biotechnol.* 1998, 18, 1191-1196.). The quenching of dyes by molecular or nanoparticle quenchers (Dubertret, B.; Calame, M.; Libchaber, A. *Nat. Biotechnol.* 2001, 19, 365-370.) or the fluorescence resonance energy transfer (FRET) between dyes was used for the optical detection of the hybridization process of the DNA to the beacon.

C. G-Quadruplex Sequences

In certain aspects, G-quadruplex sequences are used for detection of amplification of the target nucleic acid and/or the amplicon nucleic acid. In the presence of certain metal ions (e.g., $K^+$), short guanine (G)-rich sequences fold into a structure known as a G-quartet or quadruplex. Quadruplexes are very stable and biophysical studies have shown that they possess intrinsic optical properties (e.g., absorb light at 300 nm) that distinguish them from other secondary structures. Previously, quadruplex-formation assays have been developed that exploit this unique quadruplex signature to study enzymes that cleave DNA [Kankia, B. I. (2006) *A real-time assay for monitoring nucleic acid cleavage by quadruplex formation*, Nucleic acids research, 34, p. 141] or facilitate strand-exchange reactions [Kankia, B. I. (2004) *Optical absorption assay for strand-exchange reactions in unlabeled nucleic acids*, Nucleic acids research, 32, p. 154]. Briefly, when G-rich sequences with the potential to form a quadruplex are incorporated into DNA substrates they are initially in the quenched state. Upon enzymatic activity (e.g. strand cleavage or strand-exchange) the released sequence folds into a quadruplex and becomes visible when monitored by absorption and fluorescence spectroscopy. There are many publications in literature to describe how to detect G-quadruplex formation by fluorescence (Top Curr Chem (2013) 330: 111-178, Chem. Commun., 2015,51, 16033, Critical Reviews in Biochemistry and Molecular Biology, 2011; 46(6): 478-492). For instance, the porphyrins meso-5,10,15, 20-Tetrakis-(N-methyl-4-pyridyl) porphine (TMPyP4) and N-methytmesoporphyrin IX (NMM), Thioflavin have been used as quadruplex detection probes. Porphyrin interaction with DNA in the presence of low cation concentrations showed that NMM can serve as an effective fluorescent probe for quadruplex structures in presence of all cations, unlike TMPyP4. TMPyP4 was an effective probe in presence of potassium only. G-quadruplex can be detected by antibody (NATURE CHEMISTRY, VOL 5, MARCH 2013, 182). Moreover, biochemical studies show that G-quadruplex is a catalytic DNA that possesses peroxidase-like activities. Ci-quadrup1 ex can form a supramolecular complex with hemin. This complex was reported to catalyze the oxidation of 2,2'-azinobis(3-ethylbenzothiozoline)-6-sulfonic acid, ABTS, by $H_2O_2$ (a common reaction used for the assay of peroxidase activity). It was suggested that the supramolecular docking of the guanine-quadruplex layers facilitates the intercalation of hemin into the complex, and the formation of the biocatalytically active hemin center. In certain aspects, G-quadruplex sequences are used for detection of amplification of the target nucleic acid and/or the amplicon nucleic acid. The G-quadruplex sequences can be included in any of the primers in the foldback primer amplifications reaction including: one or both foldback primers, one or more stem acceleration primers, one or more loop acceleration primers, one or more kicker acceleration primers, or combinations thereof. The G quadruplex sequences are a new type of probe for use in foldback primer amplification reactions generally (rather than being specific to omega amplification) and are therefore an independent aspect of the disclosure.

D. Intercalating agents

Different types of detectable moieties have been described for the detection of amplification products. One class of detectable moieties is intercalating agents, which bind non-specifically to double-stranded nucleic acid. Intercalating agents have a relatively low fluorescence when unbound, and a relatively high fluorescence upon binding to double-stranded nucleic acids. As such, intercalating agents can be used to monitor the accumulation of double strained nucleic acids during a nucleic acid amplification reaction. Examples of such non-specific dyes include intercalating agents such as SYBR Green I (Molecular Probes), propidium iodide, ethidium bromide, and the like. Other types of detectable moieties employ derivatives of sequence-specific nucleic acid probes. For example, oligonucleotide probes are labeled with one or more dyes, such that upon hybridization to a template nucleic acid, a detectable change in fluorescence is generated.

E. Pyrophosphate

A large amount of inorganic pyrophosphate is produced as a result of the amplification reactions disclosed herein generating the amplicon nucleic acids. Pyrophosphate has been used in detection methods in the art. Exemplary detection methods are discussed below.

1. Turbidity

The robust nucleic acid amplification of the invention can generate large amounts of insoluble pyrophosphate as a reaction product. Detection using the insoluble substance as an indicator can be carried out by measuring turbidity or by detecting precipitation. Measurement of turbidity or detection of precipitation can be carried out by adding a coagulant (e.g., polyacrylic acid or carboxymethyldextran). The obtained turbidity can be used as an indicator to detect nucleic acid amplification. When measuring the absorbance, commonly employed measuring apparatuses can be used. The wavelength for measuring the absorbance can be suitably determined, and measurement is generally carried out at 300 to 800 nm, preferably at the dominant wavelength of 340 to 400 nm, and at the complementary wavelength of 600 to 800 nm. When measuring the scattered light intensity, commonly employed measuring apparatuses can be used. Specifically, measurement of changes in the absorbance over time enables the monitoring of the progress on nucleic acid amplification depending on the duration of the reaction time. (U.S. Pat. No. 7,374,879). Addition of a coagulant such as polyacrylic acid or carboxymethyldextran increases the precipitate yield and can improve the detection sensitivity. Further, these insoluble substances can be colored or labeled, thereby facilitating the detection or improving the detection sensitivity. For example, addition of Acid Orange colorizes the insoluble substances and detection is facilitated.

2. HNB Dye

Hydroxynaphthol blue (HNB) is a metal ion indicator. As disclosed above, during the Omega amplification reaction, magnesium concentration decreases since magnesium forms complexes with pyrophosphate and precipitates. The decrease in magnesium concentration accompanying nucleic acid amplification causes a change in the color of a reaction mixture to which HNB has been added in a concentration varying from 0.05 to 0.2 mM and, more preferably from 0.1 to 0.15 mM. In particular, the color of the mixture passes from a purple tone to a light blue tone. The colorimetric metal indicator particularly preferred for the aims of the present invention is hydroxynaphthol blue. Other colorimetric metal indicators can also be used, which are preferably selected from among: hydroxynaphthol blue, eriochrome black T, 8-hydroxyquinoline+butylamide, titanium yellow, xylidyl blue, calmagite, magon, thymol blue, eriochrome cyanine R, alizarin S, o-cresolphthalein, 1,2,3-trihydroxy-anthraquinone, leucoquinizarin, quinalizarin, p-nitrobenzene-azo-p-nitrobenzene-resorcinol, butylamide, chromotrope 2B, ammonia+phenolphthalein, alkaline hypoiodites, pentamethinedibarbituric acid and diphenylcarbazide. Calcein, or fluorexon, is a chelating agent that fluoresces in the presence of bound $Ca^{2+}$ and can be used as a colorimetric metal indicator.

3. Luminescence

In one embodiment, the Bioluminescent Assay in Real-Time (BART) reporter system is used to detect the synthesis of the amplicon nucleic acids. This system has been explained in detail in WO2004/062338 and WO2006/010948 (which are hereby incorporated by reference). BART is an example of a reporter system designed for isothermal amplification reactions which produces a single type of signal from a sample: a bioluminescent signal. BART uses the firefly luciferase-dependent detection of inorganic pyrophosphate. As such, molecular diagnostics can be achieved with BART simply by measuring the light emitted from closed tubes, in a homogeneous phase assay. BART has been used in a number of isothermal amplification reactions, including those operating between 50-63° C. The BART reporter is a particularly effective means to follow the rate of amplification in a reaction since the light output represents a measure of the instantaneous rate of amplification. In contrast, fluorescent detection methods typically show the accumulation of a signal and therefore the amplification rate has to be determined based upon the rate of change of fluorescent signal.

V. Applications of the Disclosed Methods

The amplification reactions disclosed herein may be used in various applications. One application includes methods for determining whether a particular target nucleic acid sequence within a template nucleic acid is present in an organism's genetic code. For example, it could be used for determining whether the nucleic acid sequence of the template nucleic acid has been genetically modified, for detection of DNA associated with a particular non-genetically modified breed of plant or a genetically modified plant, for detection of DNA associated with pedigree breeds of animal or for medical or veterinary diagnostic applications such as genetic testing or forensic. The methods of using the amplification reactions disclosed herein are also suitable for the detection of single-nucleotide polymorphisms (SNPs).

The amplification reactions disclosed herein may be also used in diagnostic methods. In particular the reactions allow identification and quantification of organisms in a patient sample and other samples. The organism may be any microorganisms, such as viruses, bacteria, mycoplasma and fungi. The microorganism can be pathogenic but it may also be a non-pathogenic microorganism. The microorganism may also be a genetically modified organism (GMO). Furthermore, the amplification reactions disclosed herein can be used to identify genetically modified crops and animals, for the detection of a disease state, for the prediction of an adverse reaction from a therapy and also for the prediction of a disease state susceptibility.

"Patient samples" include any sample taken from a subject and can include blood, stool, swabs, sputum, Broncho Alveolar Lavage Fluid, tissue samples, urine or spinal fluids. Other suitable patient samples and methods of extracting them are well known to those of skill in the art. A patient or subject from whom the sample is taken may be a human or a non-human animal. When a sample is not specifically referred to as a patient sample, the term also comprises samples taken from other sources. Examples include swabs from surfaces, water samples (for example waste water, marine water, lake water, drinking water), food samples, cosmetic products, pharmaceutical products, fermentation products, cell and microorganism cultures and other samples in which the detection of a microorganism is desirable.

VI. Kits

In a further aspect, this disclosure includes kit for use in performing the amplification reactions disclosed herein, which can be for a specific application or detection method disclosed herein. The kits preferably include all the components necessary to practice the amplification reaction or detection method disclosed herein, except the target nucleic acid which is to be amplified or tested (except where a target nucleic acid may be included as a positive control).

The kit for use in the amplification reactions and methods disclosed herein preferably comprises a polymerase, the substrates for the nucleic acid polymerase and foldback primers suitable for isothermal amplification of the target nucleic acid as well as appropriate acceleration primers. More preferably, the kit further comprises buffer reagents, such as a source of magnesium ions, or additives known to improve the shelf-life of kit reagents such as trehelose or additives known to help preserve reagents such as sodium azide. Alternatively, a kit for use in a method according to the invention may comprise only some of these components and/or additional components. The sample and any other components that have been omitted from the kit may then be added to the kit during use.

The kits may include additional components suitable for any detection methods to be performed during or after the amplification reaction of the kit. For example, the kit may include a thermostable luciferase, luciferin and an enzyme that converts inorganic pyrophosphate (PPi) to ATP, such as ATP sulphurylase, and any other required substrates or cofactors of the enzyme that converts PPi to ATP, such as adenosine 5' phosphosulphate, may be included in the kit.

Preferably, at least one of the components of the kit is lyophilized or is in another form which is suitable for storage in the kit. More preferably, all of the components of the kit are lyophilized or in one or more other forms suitable for storage. Such other forms include components to which stabilizing factors have been added and/or a refrigerated or frozen master mix that contains the components of the kit.

EXAMPLES

The following are examples of methods and compositions of the present disclosure. It is understood that various other embodiments may be practiced, given the general description provided above.

Example 1

Figure 9:
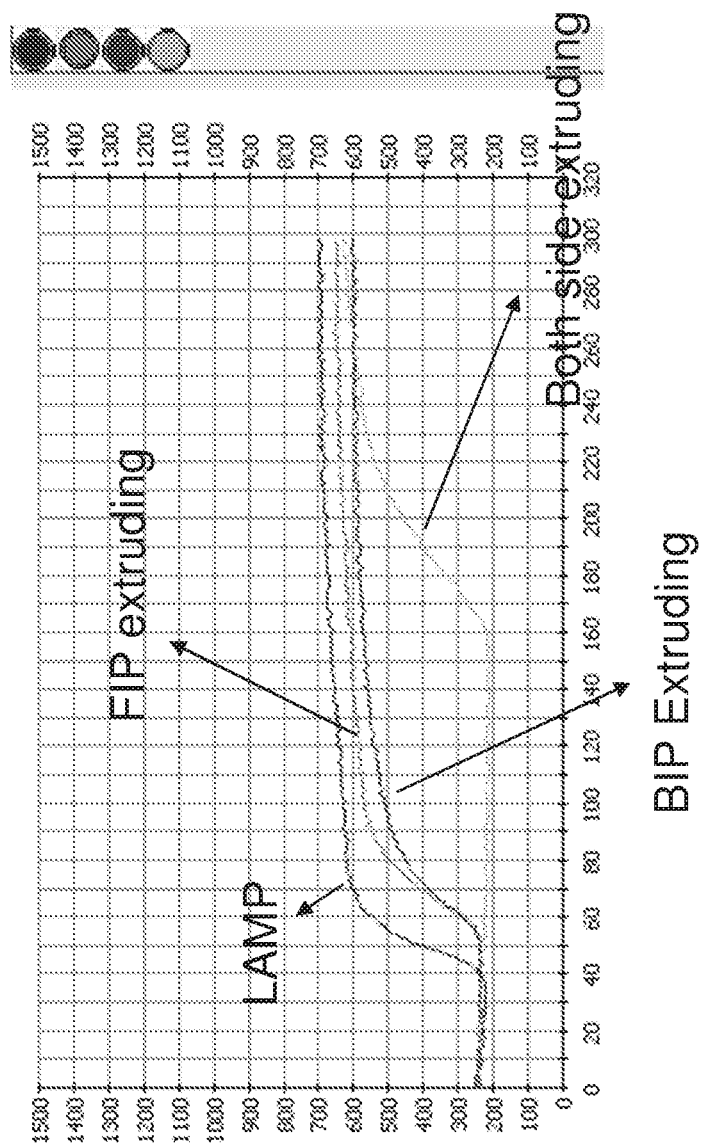
FIG. 9 shows a comparison of real time amplification with Omega primers containing extruding sequences on the first (FIP), second (BIP), or on both primers as compared to LAMP primers not containing extruding sequences.

Comparison of HPV18 Real Time Isothermal Amplification with Omega Primers and LAMP Primers Omega primers containing extruding sequences on either the first primer (exFIP), second primer (ex:BIP), or both primers were utilized in real-time isothermal amplification reactions. Amplification reaction were carried out in a 25 ul reaction containing 20 mM Tris-HCl, 10 mM (NH4)2SO4, 10 mM KCl, 4 mM MgSO4, 0.1% Triton X-100, 0.4 mM each dNTP, 0.2 M Betaine, foldback primers 0.8 µM 18FIP (SEQ ID NO:1.) or ex18FIP (SEQ ID NO:2) and 0.8 µM 18BIP (SEQ ID NO:3) or ex18BIP (SEQ ID NO:4), loop acceleration primers 0.4 µM 18LF (SEQ ID NO:5) and 0.3 µM18LB (SEQ ID NO:6), FQ probe 0.1 µM FAM-18LB (SEQ ID NO:7) and 0.1 µM Q-oligo (SEQ ID NO:8), kicker acceleration primers 0.2 µM 18KF (SEQ :ID NO:9) and 0.2 µM 18KB (SEQ ID NO:10), 8 Units of Bst DNA polymerase Large Fragment (New England Biolabs) and 20,000 copies of non-denatured recombinant plasmids containing HPV18 sequences (SEQ ID NO:11). The reaction was carried out at 60° C. for 150 minutes with FAM fluorescence measured at 30 second interval in a Biorad IQ-5 Real-time PCR Instrument. The real-time amplification profile was compared to that of LAMP primers (FIG. 9). Both LAMP primers and extruding omega primers were able to amplify target DNA and gave comparable real-time fluorescent signal intensity. Amplification with a single-side omega primer showed a slightly slower rate comparing to a standard LAMP reaction using this primer set. Amplification with omega primers on both sides showed a dramatic delay comparing to a standard LAMP reaction.

```
                                            (SEQ ID NO: 1)
5'-ACGTCTGGCCGTAGGTCTTTGCAGCTACAGCACACCCCTCA (SEQ ID NO: 2)
5'-TTTTTTTTTT-
ACGTCTGGCCGTAGGTCTTTGCAGCTACAGCACACCCCTCA (SEQ ID NO: 3)
5'-TGCTACACGACCTGGACACTGTGGA-
TGTAGGTGTAGCTGCACCGAGA (SEQ ID NO: 4)
5'-TTTTTTTTTT-TGCTACACGACCTGGACACTGTGGA-
TGTAGGTGTAGCTGCACCGAGA (SEQ ID NO: 5)
5'-CGGACACGGTGCTGGAATAC (SEQ ID NO: 6)
5'-CATTGTGGACCTGTCAACCCA (SEQ ID NO: 7)
5'-Fam-CACAGCCACTCCGCAGGGTCCACGCACGATCGCACCTG-
CATTGTGGACCTGTCAACCCA (SEQ ID NO: 8)
5'-CAGGTGCGATCGTGCGTGGACCCTGCGGAGTGGCTGTG-BHQ (SEQ ID NO: 9)
5'-CGGTATCCGCTACTCAGCTTGT (SEQ ID NO: 10)
5'-TGTTACCACTACAGAGTTTCCGTCTT (SEQ ID NO: 11)
5'-
AATATGGGAACACAGGTACGTGGGAAGTACATTTTGGGAATAATGTAATT
GATTGTAATGACTCTATGTGCAGTACCAGTGACGACACGGTATCCGCTAC
TCAGCTTGTTAAACAGCTACAGCACACCCCCTCACCGTATTCCAGCACCG
TGTCCGTGGGCACCGCAAAGACCTACGGCCAGACGTCGGCTGCTACACGA
CCTGGACACTGTGGACTCGCGGAGAAGCAGCATTGTGGACCTGTCAACCC
ACTTCTCGGTGCAGCTACACCTACAGGCAACAACAAAAGACGGAAACTCT
GTAGTGGTAACACTACGCCTATAATACATTTAAAAGGTGAGAGAAACAGT
TTAAAATGTTTACGGTACAGATTGCGAAAACATAGCGACCACTATAGAGA
```

Example 2

Comparison of Omega and LAMP Amplification Product Size

Figure 10:
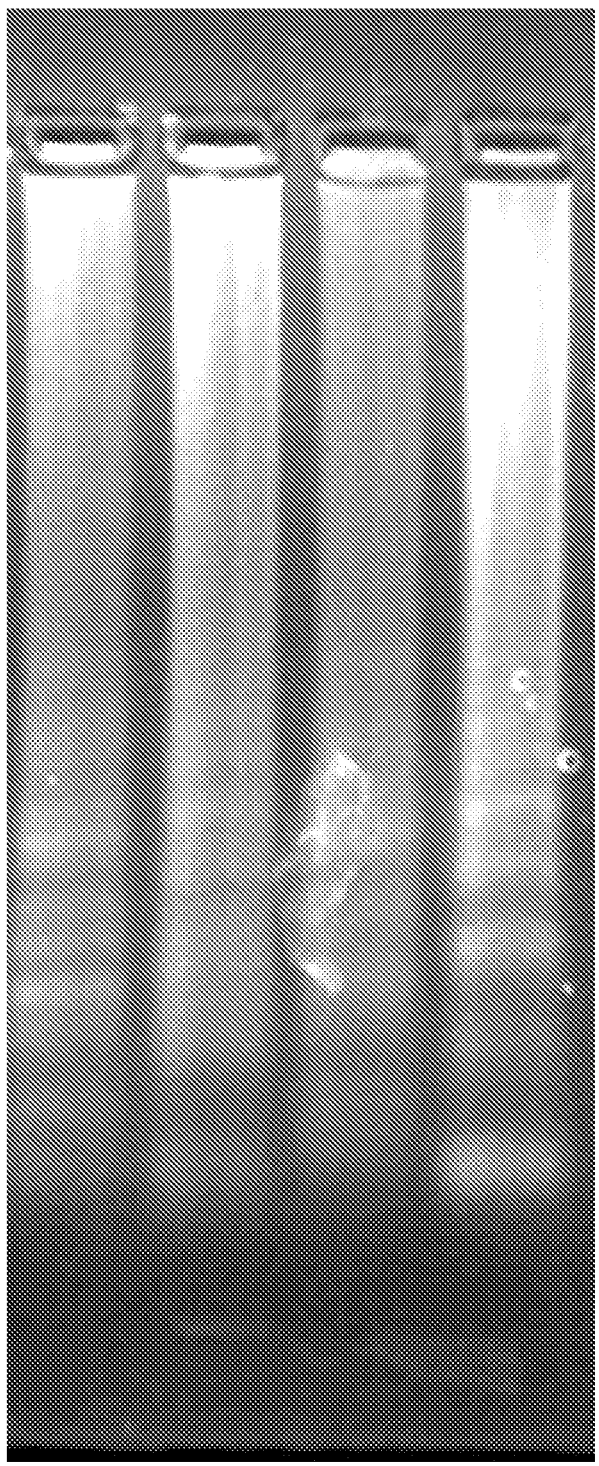
FIG. 10 shows a gel image of :KR amplification products produced using Omega primers containing extruding sequences as compared to LAMP primers not containing extruding sequences. Lane 1: Omega FIP with extruding sequences, 10 NT long. Lane 2: Omega BIP with extruding sequences, 10 NT long. Lane 3: Omega FIP and BIP both contain extruding sequences, 10 NT long. Lane 4: LAMP amplification as a control.

Amplification products were run on a 1.5% agarose gel with 0.5 µg/ml Ethidium Bromide in TBE buffer. The amplified DNA products were visualized under UV light. Both Omega and LAMP primers generated large amplification products with a similar size pattern (FIG. 10).

Example 3

Comparison of Omega and LAMP Products by Restriction Enzyme Digestion Analysis Experiments were performed as described in Example 1 except with following fold-back primer pairs for each reaction: Lane 1&5, EcoRI-ex18FIP (SEQ ID NO:12) and 18BIP (SEQ ID NO:3); Lane 2&6, 18FIP (SEQ ID NO:1) and EcoRI-ex18BIP (SEQ ID NO:13); Lane 3,4,7,8 EcoRI-18HP (SEQ ID NO:14) and 18BIP (SEQ ID NO:3). Amplification products were separated on a 1.5% agarose gel in TBE buffer. The gel was stained with Ethidium Bromide and the amplified DNA products were visualized under UV light.

Figure 11:
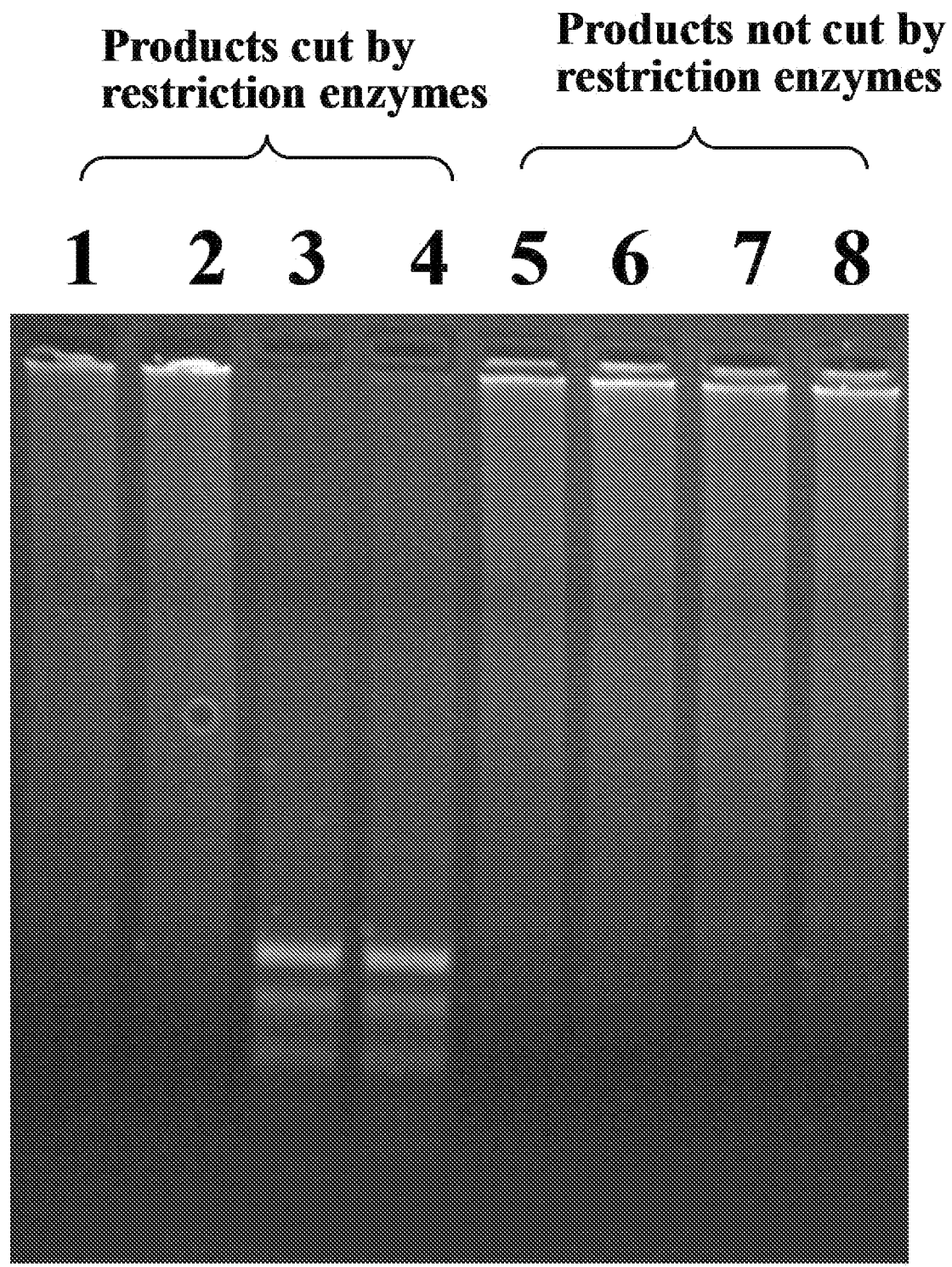
FIG. 11 shows a gel image of Omega amplification products and LAMP amplification products cut by restriction enzymes. Lane 1: Omega amplification product by a 10 nt extruding HP primer was cut by the restriction enzyme EcoRI whose recognition site was located in the E2 position (joint sequence inserted between extruding sequence and fold-back sequence of FIP). Lane 2: Omega amplification product by a 22 nt extruding BIP primer was cut by the restriction enzyme EcoRI whose recognition site was located in the E2 position (between extruding sequence and fold-back sequence of BIP). Lane 3: Standard LAMP amplification product was cut by the restriction enzyme EcoRI whose recognition site was located in the El position (joint sequence inserted between F1c and F2 of FIP). Lane 4: Replicate of lane 3. For comparison, lanes 5-8 show the amplification products from lanes 1-4 without restriction enzyme digestion.
Figure 12:
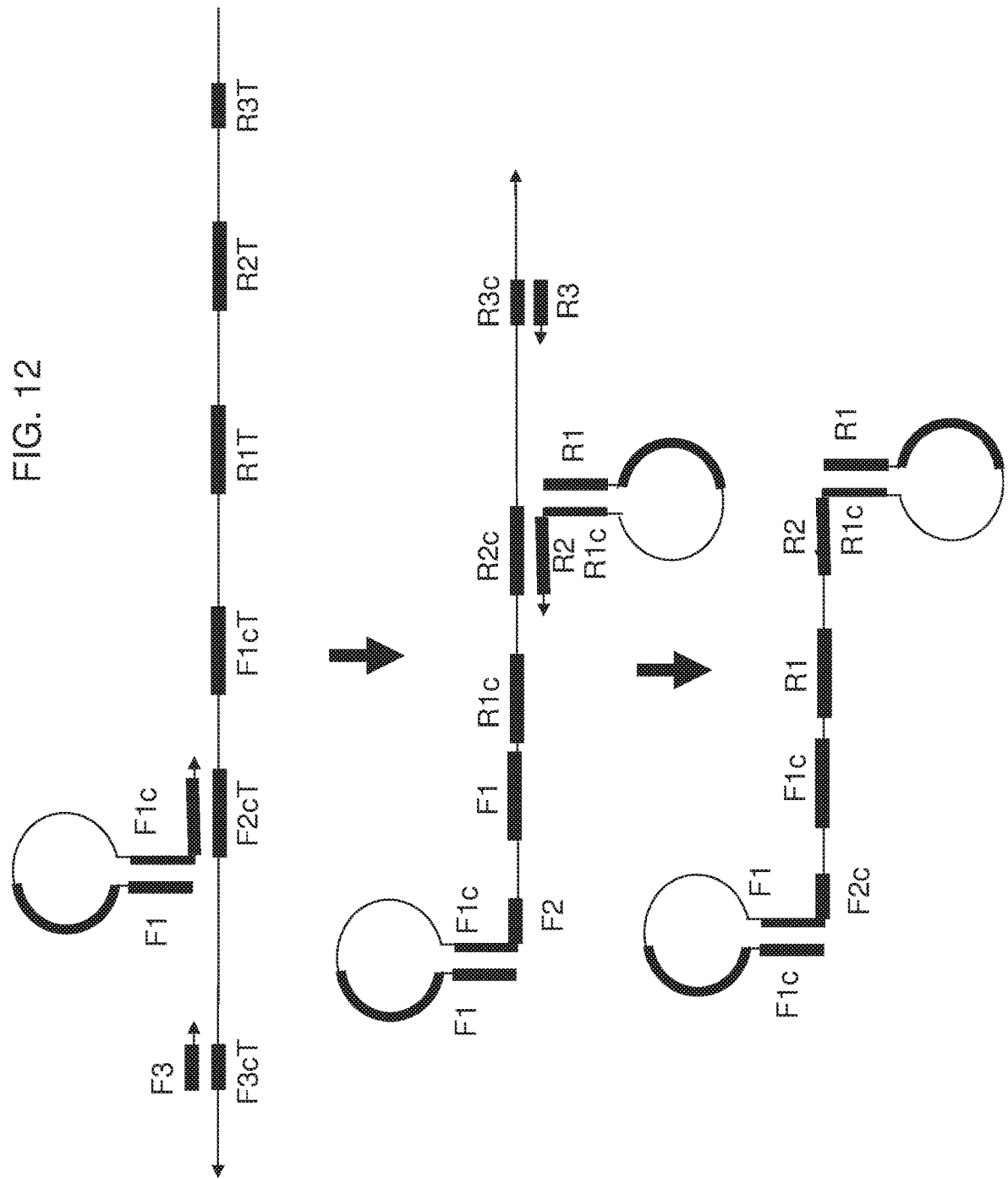
FIG. 12 shows an exemplary implementation of omega amplification by either a forward extruding primer having hairpin structure at 5' terminus or a reverse extruding primer having hairpin structure at 5' terminus, or both.
Figure 13:
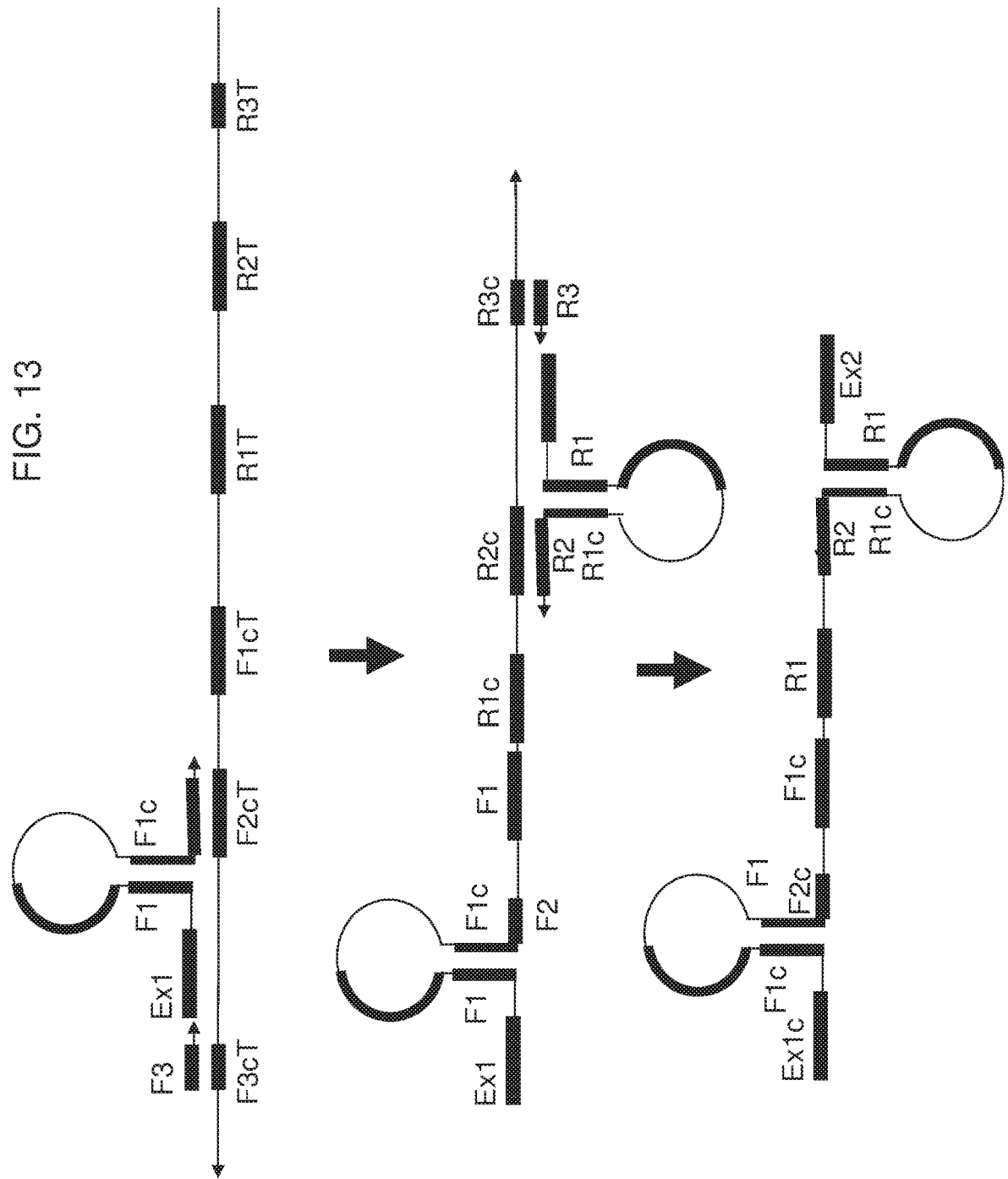
FIG. 13 shows an exemplary implementation of omega amplification by either a forward extruding primer having hairpin structure at middle or a reverse extruding primer having hairpin structure at middle, or both.

Amplification products produced using Omega and LAMP primers were treated with restriction enzymes EcoRI, and subsequently run on a gel to determine the size patterns of the digested products (FIG. 11). Lanes 1-4 display amplification products cut by the restriction enzymes. Lanes 5-8 display amplification products not cut by the restriction enzymes. These results demonstrate that, unlike in the LAMP amplification where the HP and BIP sequences are duplicated repeatedly in the final amplification products, the Omega extruding sequence is not repeatedly duplicated in the amplification product. Therefore, the Omega amplification products were not cut by the restriction enzyme EcoRI repeatedly to produce short and distinguishable fragments, while the LAMP amplification products were cut into short and distinguishable fragments by restriction enzymes.

```
                                            (SEQ ID NO: 12)
5'-TTTTGAATTC-
ACGTCTGGCCGTAGGTCTTTGCAGCTACAGCACACCCCTCA (SEQ ID NO: 13)
5'-TTTTTTTTTTTTTTTTGAATTC-
TGCTACACGACCTGGACACTGTGGA-TGTAGGTGTAGCTGCACCGAGA (SEQ ID NO: 14)
5'-ACGTCTGGCCGTAGGTCTTTGC-GAATTC-
AGCTACAGCACACCCCTCA
```

Example 4

Omega Amplification with Both Folding Primer Fold to the Same Region in the Template Experiments were performed as described in Example 1 except with following primers: omega amplification primers 0.8 µM 73ovlp-exFIP (SEQ ID NO:15) (or 7350ovlp-exHP (SEQ ID NO:16) or 73-exFIP (SEQ ID NO:17)), 0.8 µM 73-BIP (SEQ ID NO:18), loop acceleration primers 0.4 µM 73ovlp-LF (SEQ ID NO:19) (or 7350ovlp-LF (SEQ ID NO:20) or 73-LF (SEQ ID NO:21), correspondingly), and 0.3 µM 73-LB (SEQ ID NO:22), FQ probe 0.1 µM Fam-73-LB (SEQ ID NO:23), 0.1 µM Q-oligo (SEQ ID NO: 8), and kicker acceleration primers 0.2 µM 73-KF (SEQ ID NO:24) and 0.2 µM 73-KB (SEQ NO:25), with 20,000 copies of recombinant plasmids containing HPV73 sequences as template DNA (SEQ ID NO:26). The reaction was carried out at 60° C. for 100 minutes with fluorescence measured at 30 second interval in a Biorad IQ-5 Real-time PCR Instrument. Both standard Omega amplification and overlapping folding Omega amplification were able to amplify target DNA and gave comparable real-time fluorescent signal curves.

```
                                              (SEQ ID NO: 15)
5'-TTTTTTTTTT-ACTCTCGTTCAGCTTGTCTGTCTAGAT-
CTTACATGTTACGAGTCATTGGACA (SEQ ID NO: 16)
5'-TTTTTTTTTT-TTGTCTGTCTAGATGGCTGTCTGTTTC-
CCGAAATTGACCTTACATGTTACGAGT (SEQ ID NO: 17)
5'-TTTTTTTTTT-GCTGTCTGTTTCATCCTCATCCTCTG-
GAAACCAACAACCGAAATTGACCTT (SEQ ID NO: 18)
5'-ATCTAGACAGACAAGCTGAACGAGAGT-
TGTTGCTTTCAATGGCAAGGC (SEQ ID NO: 19)
5'-GTCTGTTTCATCCTCATCCTCT (SEQ ID NO: 20)
5'-CTCATCCTCTGAGTTGTCCA (SEQ ID NO: 21)
5'-AGTTGTCCAATGACTCGTAACATG (SEQ ID NO: 22)
5'-AGAATAGTTACTGACTGCACGAAGT (SEQ ID NO: 23)
5'-Fam-CACAGCCACTCCGCAGGGTCCACGCACGATCGCACCTG-
AGAATAGTTACTGACTGCACGAAGT (SEQ ID NO: 24)
5'-CCTTGCAGGACATTACTTTAGACCT (SEQ ID NO: 25)
5'-ACCCATAAGCAACTCTTCTATCACTC (SEQ ID NO: 26)
5'-
AAGATGCATGGAAAAAAACAACCTTGCAGGACATTACTTTAGACCTGAA

ACCAACAACCGAAATTGACCTTACATGTTACGAGTCATTGGACAACTCAG
AGGATGAGGATGAAACAGACAGCCATCTAGACAGACAAGCTGAACGAGAG

TGTTACAGAATAGTTACTGACTGCACGAAGTGTCAGTGCACAGTATGCCT

TGCCATTGAAAGCAACAAAGCTGATTTAAGAGTGATAGAAGAGTTGCTTA

TGGGTACACTAGGTATTGTGTGCCCCAACTGTTCCAGA
```

Example 5

STEM Primer Accelerates Omega Amplification

Experiments were performed as described in Example 1 except with following primers: 0.8 µM HPV6G-FIP (SEQ ID NO:27), 0.8 µM HPV6G-BIP (SEQ ID NO:28) or 0.8 µM HPV6G BIP-22nt (SEQ ID NO:29), forward loop accelerator primer 0.4 µM HPV6G-LF (SEQ ID NO:30), FQ Probe 0.1 µM HPV6G-LB-Fam (SEQ ID NO:31) and 0.1 µM Q-oligo (SEQ ID NO:8), reverse loop accelerator primer 0.3 µM HPV6G-LB (SEQ ID NO:32), and kicker accelerator primers 0.2 µM HPV6G-KF (SEQ ID NO:33) and 0.2 µM HPV6G-KB (SEQ ID NO:34), with or without 0.4 µM HPV6GP (SEQ ID NO:47) in the presence of 20,000 copies of recombinant plasmids containing HPV6 sequences as template DNA (SEQ ID NO:35). The reaction was carried out at 60° C. for 90 minutes with fluorescence measured at 30 second interval in a Biorad IQ-5 Real-time PCR Instrument. Real-time amplification curves showed that the stem primer significantly accelerated Omega amplification.

```
                                              (SEQ ID NO: 27)
5'-CGAACGTTGCTGTCACATCCACAG-
TGGACGGACAAGATTCACAACCTT (SEQ ID NO: 28)
5'-GAGAAGTGCAACAGCTTCTGTTGGG-
CTGAATCGTCCGCCATCGTT (SEQ ID NO: 29)
5'-TTTTTTTTTTTTTTTTTTTTTT-
GAGAAGTGCAACAGCTTCTGTTGGG-CTGAATCGTCCGCCATCGTT (SEQ ID NO: 30)
5'-CAACAGGTCACTATTTGGTAATGTTGTT (SEQ ID NO: 31)
5'-FAM-CACAGCCACTCCGCAGGGTCCACGCACGATCGCACCTG-
CATCTGCGCACCGAAGACA (SEQ ID NO: 32)
5'-CATCTGCGCACCGAAGACA (SEQ ID NO: 33)
5'-GCAATTAGTAGACAGCTCAGAAGATGA (SEQ ID NO: 34)
5'-TGTACACCCAGACCCCTCAT (SEQ ID NO: 47)
5'-TGGTTGTGCAGTGTACAGAAACAGACATCA (SEQ ID NO: 35)
5'-
CCCTGTAGGGTTACATTGCTATGAGCAATTAGTAGAGAGCTCAGAAGATG

AGGTGGACGAAGTGGACGGACAAGATTCACAACCTTTAAAACAACATTAC

CAAATAGTGACCTGTTGCTGTGGATGTGACAGCAACGTTCGACTGGTTGT

GCAGTGTACAGAAACAGACATCAGAGAAGTGcAACAGCTTCTGTTGGGAA

CACTAAACATAGTGTGTCCCATCTGCGCACCGAAGACATAACAACGATGG
```

-continued

CGGACGATTCAGGTACAGAAA<u>ATGAGGGGTCTGGGTGTACA</u>GGATGGTTT

ATGGTAGAAGCTA

Example 6

Fold-Back Loop Primers Accelerate LAMP and Omega Amplification

Experiments were performed as described in Example 1 except with following primers for LAMP amplification reactions: 35-FIP (SEQ ID NO: 36), 35-BIP (SEQ ID NO: 37), 35-LF (SEQ ID NO: 38) or 35-FBLF (SEQ ID NO: 39), 35-LB (SEQ ID NO: 40) or 35-FBLB (SEQ ID NO: 41), 35-KF (SEQ ID NO: 42), 35-KB (SEQ ID NO: 43) and 0.1 μM 35-LF-FAM (SEQ ID NO: 44); and for Omega amplification reactions: 35-exFIP (SEQ ID NO: 45), 35-BIP, 35-LF or 35-FBLF, 35-LB or 35-FBLB, 35-KF, 35-KB and 0.1 μM 35-LF-FAM, in the presence of 2,0000 copies of recombinant plasmids containing HPV35 sequences as template DNA (SEQ ID NO: 46). The reaction was carried out at 60° C. for 40 minutes with fluorescence measured at 60 second interval in a Biorad CFX-96 Real-time PCR Instrument. Compared to regular loop primers, fold-back loop primers accelerated isothermal amplification reactions both in the LAMP and Omega amplifications.

(SEQ ID NO: 36)
5'-AGGCTTTGGTATGGGTCTCGGTGGT-
GCACAGAACTATCCACTGCTGA (SEQ ID NO: 37)
5'-GGCACCACAGAAACGCAGAAGACA-CTGAGTCGCACTCGCTTGG (SEQ ID NO: 38)
5'-GGCGTGTAGCTGTGTAGCAAT (SEQ ID NO: 39)
5'-AGGCTTTGGTATGGGTCTCGGTGGT-
GGCGTGTAGCTGTGTAGCAAT (SEQ ID NO: 40)
5'-AATCACAAACGACTTCGAGGGG (SEQ ID NO: 41)
5'-GGCACCACAGAAACGCAGAAGACA-
AATCACAAACGACTTCGAGGGG (SEQ ID NO: 42)
5'-GTAATTGTTTGTCCTGAATCTGTATTTAGC (SEQ ID NO: 43)
5'-GTCAACACTGTCCACGGCA (SEQ ID NO: 44)
5'-FAM-CACAGCCACTCCGCAGGGTCCACGCACGATCGCACCTG
GGCGTGTAGCTGTGTAGCAAT (SEQ ID NO: 45)
5'-TTTTTTTTTT-AGGCTTTGGTATGGGTCTCGGTGGT-
GCACAGAACTATCCACTGCTGA (SEQ ID NO: 46)
5'-
TATGGGAAGTGCATGTGGGTGGTCAG<u>GTAATTGTTTGTCCTGAATCTGTA

TTTAGC</u>AGCACAGAACTATCCACTGCTGAAATTGCTACACAGCTACACGC

CTACAACACCACCGAGACCCATACCAAAGCCTGCTCCGTGGGCACCACAG

AAACCCAGAAGACAAATCACAAACGACTTCGAGGGGGTACCGAGCTCCCC

-continued
TACAACCCCACCAAGCGAGTGCGACTCAG<u>TGCCGTGGACAGTGTTGA</u>CAG

AGGGGTCTACTCTACATCTGA

Example 7

Figure 14:
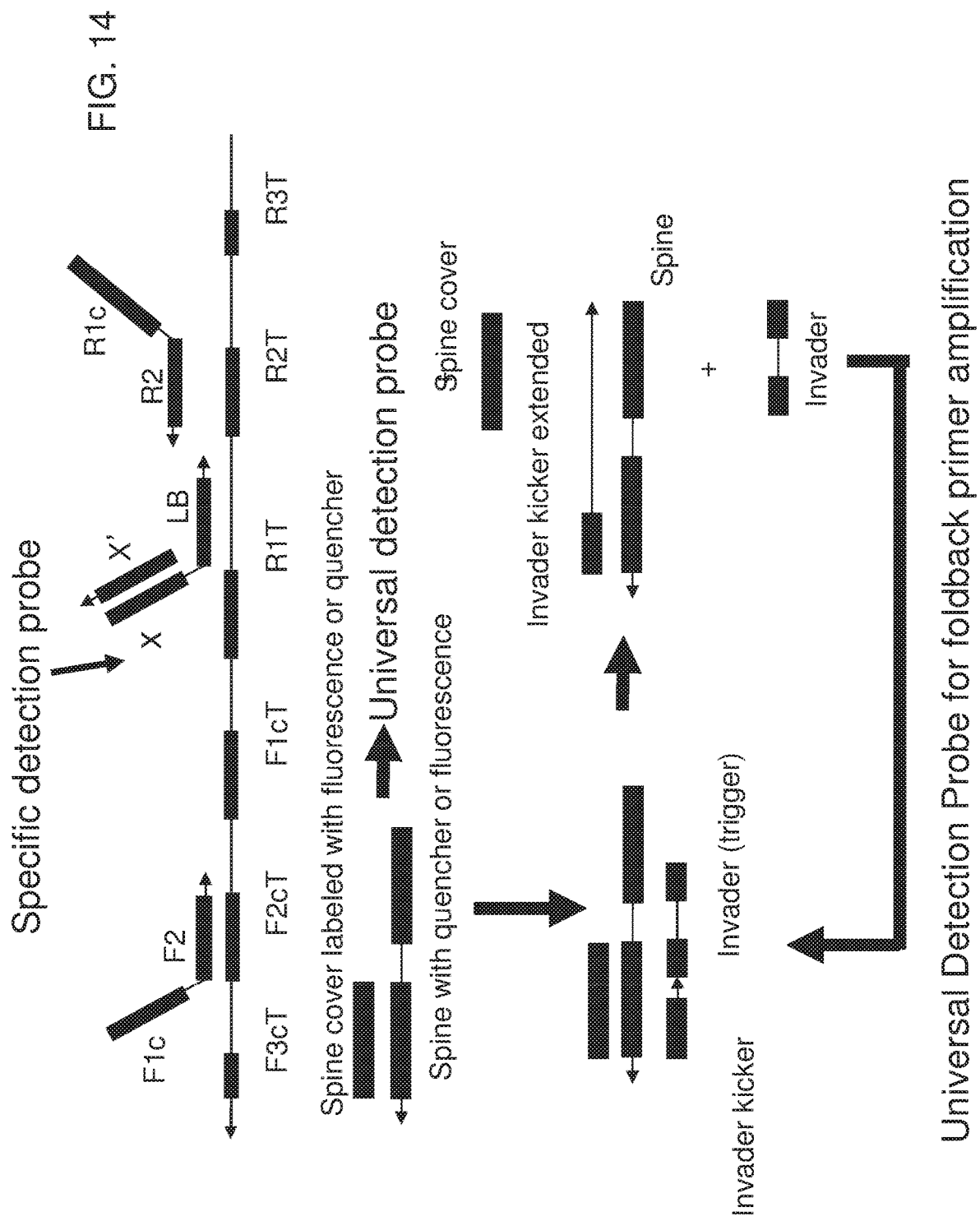
FIG. 14 shows an exemplary implementation of a signal detection method in foldback primer amplification using one type of universal detection probes system. The universal detection probe having spine sequence (the second strand of FQ probe) is labeled with fluorescence at the 3' end and correspondingly the spine cover (the first strand of FQ probe labeled with quencher at 5' end) hybridized with spine sequence is labeled with quencher at its 5' end. Reverse complementary of the specific detection probe of the loop primer in LAMP amplification is replaced and becomes single stranded from the reaction, and then serves as a trigger (FQ invader) to replace spine cover to generate detection fluorescent signal. After displacing the spine cover by the trigger, the trigger in turn gets displaced by FQ invader kicker primer extension and can therefore be used in the next round of signal generation.

Universal Detection Probes can be Used as a Signal Amplification and Detection Method for an Target Sequence Detection or for an Isothermal Amplification Reaction Universal detection probes were utilized to detect an invader trigger in a real-time isothermal reaction using the format as shown in FIG. 14. Reaction were carried out in a 25 ul reaction containing 20 mM Tris-HCl, 10 mM (NH4) 2SO4, 10 mM KCl, 4 mM MgSO4, 0.1% Triton X-100, 0.4 mM each dNTP, 0.2 M Betaine, 0.1 μM spine sequence (SEQ ID NO: 74), 0.1 μM spine cover (SEQ ID NO: 48), 0.8 μM universal primer (SEQ ID NO: 49), 8 Units of Bst DNA polymerase Large Fragment (New England Biolabs) and various concentration of invader trigger (SEQ ID NO: 50) as the target. Spine sequence and spine cover were mix together before universal primer and polymerase were added. The reaction was carried out at 60° C. for 60 minutes with FAM fluorescence measured at 60 second interval in an ABI StepOne Real-time PCR Instrument. This universal detection system was able to amplify and detect signal generated from less than 8 nM invader trigger (FIG. 23A).

Figure 23B:
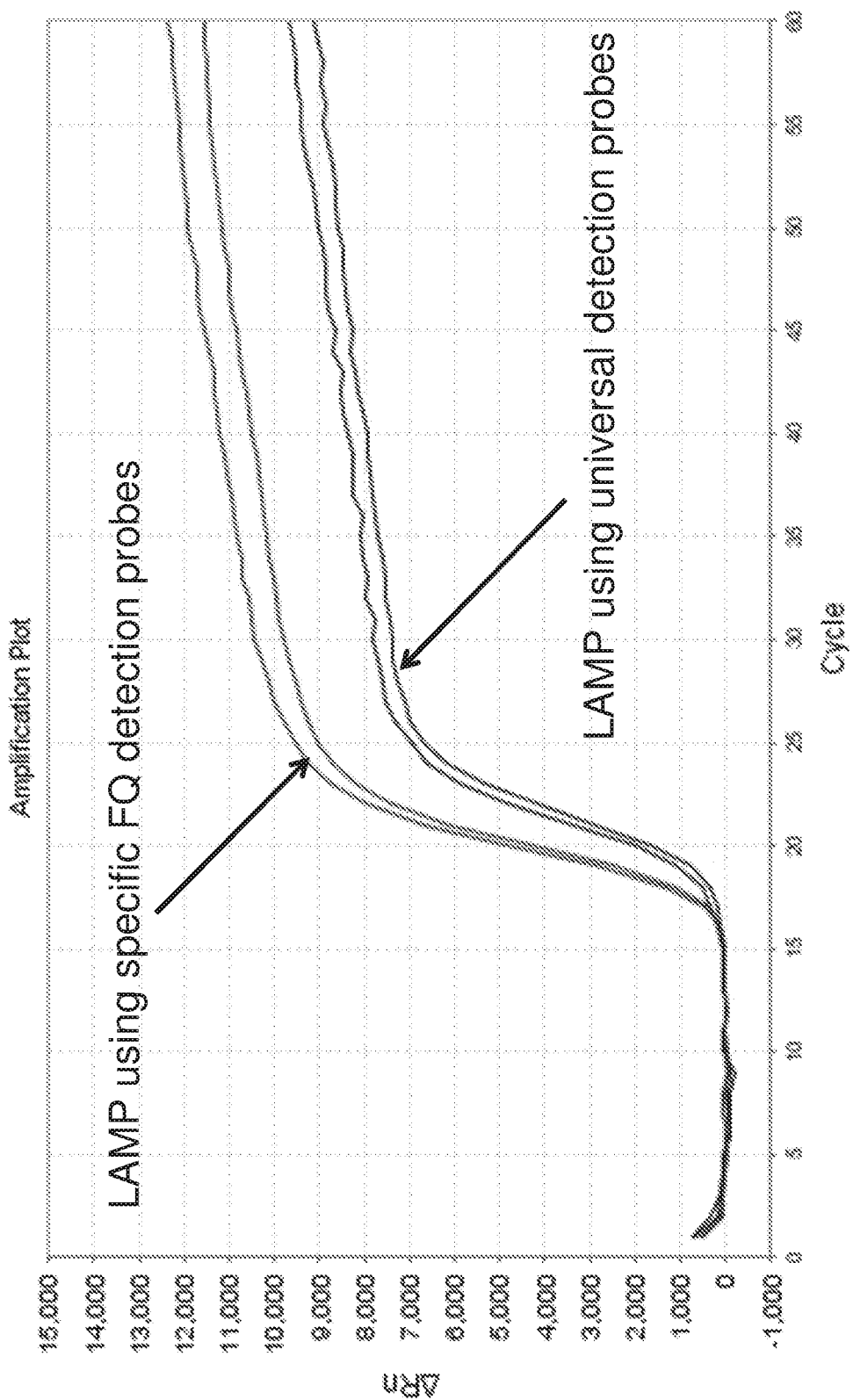
FIG. 23B shows comparison result of a LAMP reaction using universal detection probe as shown in FIG. 9 as compared to a LAMP reaction using specific FQ probe

Moreover, these universal detection probes were utilized in a LAMP reaction in replacement of a specific FQ probe using a design shown in FIG. 9. Experiments were performed as described above except with following primers for LAMP amplification reactions and signal detection: 33-FIP (SEQ ID NO: 51), 33-B1P (SEQ ID NO: 52), 33-LF (SEQ ID NO: 53), 33-LB (SEQ ID NO: 54), 33-KF (SEQ ID NO: 55), 33-KB (SEQ ID NO: 56), and 0.1 μM 33-FQ-LB (SEQ ID NO: 57) with quencher probe (SEQ ID NO:8) or 0.1 μM 33-TRIGGER'-LB (SEQ ID NO: 58) with universal detection probes (SEQ ID NO: 48-50 and 74). 10000 copies of plasmid containing HPV33 target sequence (SEQ ID NO: 59) were used as template. 33-FQ-LB and quencher probe, or 33-TRIGGER'-LB and trigger sequence were pre-mixed before being added to the reaction. Signal detection using universal detection probe showed comparable speed as that using specific probe detection (FIG. 23B)

(SEQ ID NO: 74)
5'-
AGCCTGAGTGCGTCCAACCGTGCGACAGGTGCGATCGTGCGTGGACCCTGC
GGAGTGGCTGTG-BHQ (SEQ ID NO: 48)
5'-Fam-CACAGCCACTCCGCAGGGTCCACGC-TT (SEQ ID NO: 49)
5-CACAGCCACTCCGC (SEQ ID NO: 50)
5'-AGGGTCCACGC-ACGATCGCACCTGTCGCACGGTTGGACGCACTC (SEQ ID NO: 51)
5'-CACAGGTAGGGCACACAATATTCACTG-
CAACAGTACAGCAAGTCACCTACGA (SEQ ID NO: 52)
5-AACATCATCTACAATGGCCGATCCTGA-
GACTGCTTCTACCTCAAACCAACC

-continued (SEQ ID NO: 53)
5'-TGCCCATAAGTAGTTGCTGTATGGT (SEQ ID NO: 54)
5'-GTACAAATGGGGCTGGGATG (SEQ ID NO: 55)
5'-CACTTGTAACACCACAGTTCGTT (SEQ ID NO: 56)
5'-TCTGAAATATTATCTCCTGTTCTTCTCTCT (SEQ ID NO: 57)
5'-Fam-CACAGCCACTCCGCAGGGTCCACGCACGATCGCACCTG-
GTACAAATGGGGCTGGGATG (SEQ ID NO: 58)
5-
GAGTGCGTCCAACCGTGCGACAGGTGCGATCGTGCGTGGACCCT-
GTACAAATGGGGCTGGGATG (SEQ ID NO: 59)
5'-
CACTTGTAACACCACAGTTCGTTTATGTGTCAACAGTACAGCAAGTGACC

TACGAACCATACAGCAACTACTTATGGGCACAGTGAATATTGTGTGCCCT

ACCTGTGCACAACAATAAACATCATCTACAATGGCCGATCCTGAAGGTAC

AAATGGGCTGGGATGGGGTGTACTGGTTGGTTTGAGGTAGAAGCAGTCA

TAGAGAGAAGAACAGGAGATAATATTTCAGA

Example 8

Figure 15:
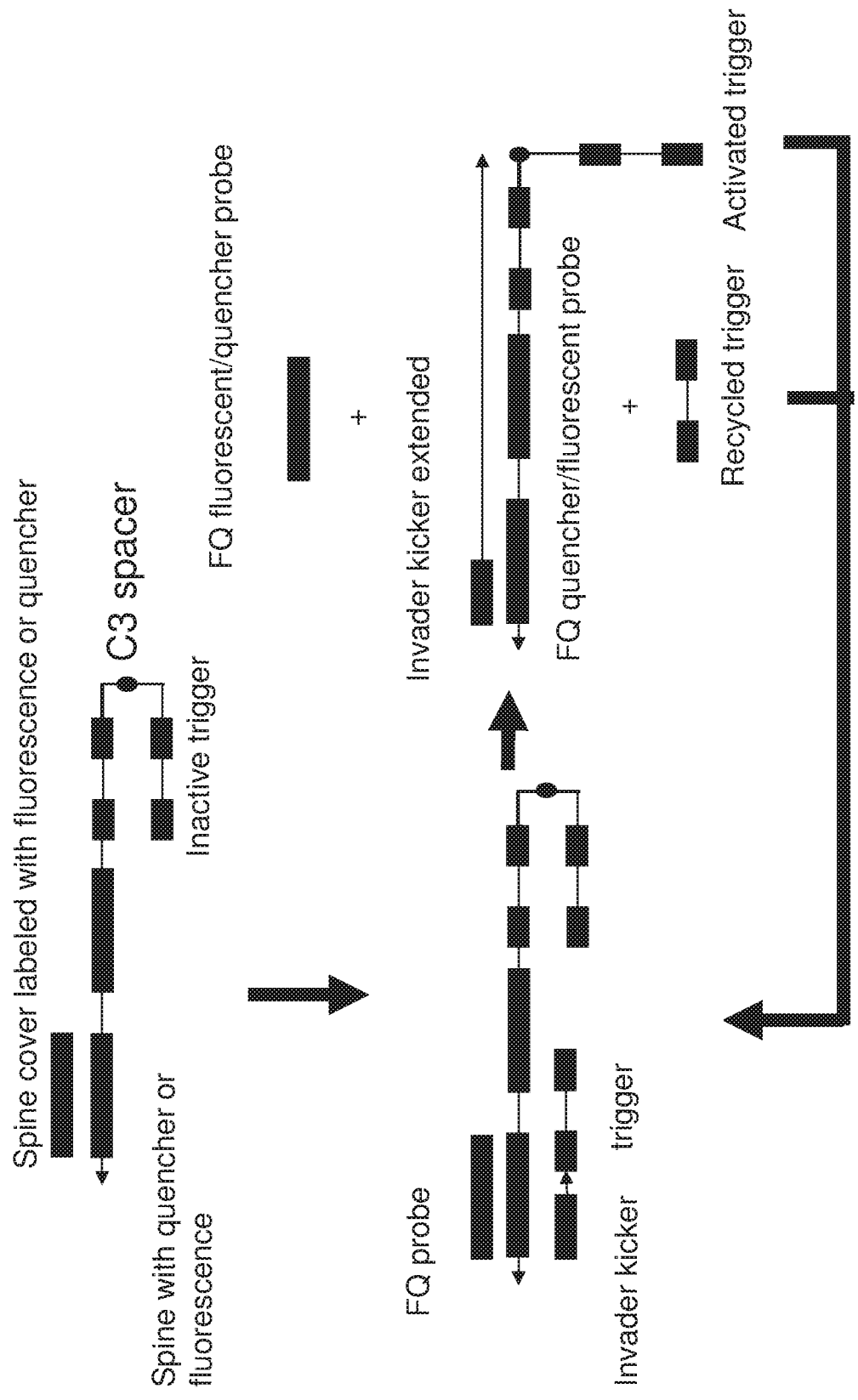
FIG. 15 shows an exemplary implementation of an exponential signal detection method in foldback primer amplification using one type of universal detection probes system describe in FIG. 14. The spine is labeled with fluorescence or quencher at the 3' end and correspondingly the spine cover hybridized with spine is labeled with quencher or fluorescence at its 5' end. The spine contains a copy of a trigger sequence (inactivated trigger) at its 5' end and keeps it inactive by hybridizing it with its reverse complementary sequence. Specific probe or reverse complementary of specific probe becomes single stranded from the reaction, serves as the trigger, and displaces the spine cover with the universal primer (FQ invader kicker) to separate fluorescent dye from quencher to generate signal, The trigger from the reaction and the inactive trigger gets displaced by universal primer extension and both can therefore be used in the next round of signal generation.

Universal Detection Probes with Additional Trigger in Spine can be Used as a Signal Amplification and Detection Method Universal detection probes with additional trigger in spine were utilized to detect an invader trigger in a real-time isothermal reaction using the format as shown in FIG. 15. Reaction were carried out in a 25 ul reaction containing 20 mM Tris-HCl, 10 mM (NH4)2SO4, 10 mM KCl, 4 mM MgSO4, 0.1% Triton X-100, 0.4 mM each dNTP, 0.2 M Betaine, 0.1 µM spine sequence (SEQ ID NO: 75-C3spacer-SEQ ID NO: 76), 0.1 µM spine cover (SEQ ID NO: 77), 0.2 µM invader kicker (SEQ ID NO: 49), 8 Units of Bst DNA polymerase Large Fragment (New England Biolabs) and various concentration of invader trigger (SEQ ID NO: 50) as the target. Spine sequence and spine cover were mix together before universal primer and polymerase were added. The reaction was carried out at 60° C. for 60 minutes with FAM fluorescence measured at 60 second interval in an ABI StepOne Real-time PCR Instrument.

5'-CGAGA-AGGGTCC-

ACGCACGATCGCACCTGTCGCACGGTTGGACGCACTC-GA-C3spacer-

GA-GAGTGCGTCCAACCGTGCGACAGGTGCGATCGTGCGT-GGACCCT-

TCTCG-TTTTTGAGTGCGTCCAACCGTGCGACAGGTGCGATCGTGCGTG

GACCCTGCGGAGTGGCTGTC-Fam (SEQ ID NO: 75-C3spacer-

SEQ ID NO: 76)

(SEQ ID NO: 77)
5-BHQ-GACAGCCACTCCGCAGGGTCCACGCACG-TTT

Example 9

Figure 16:
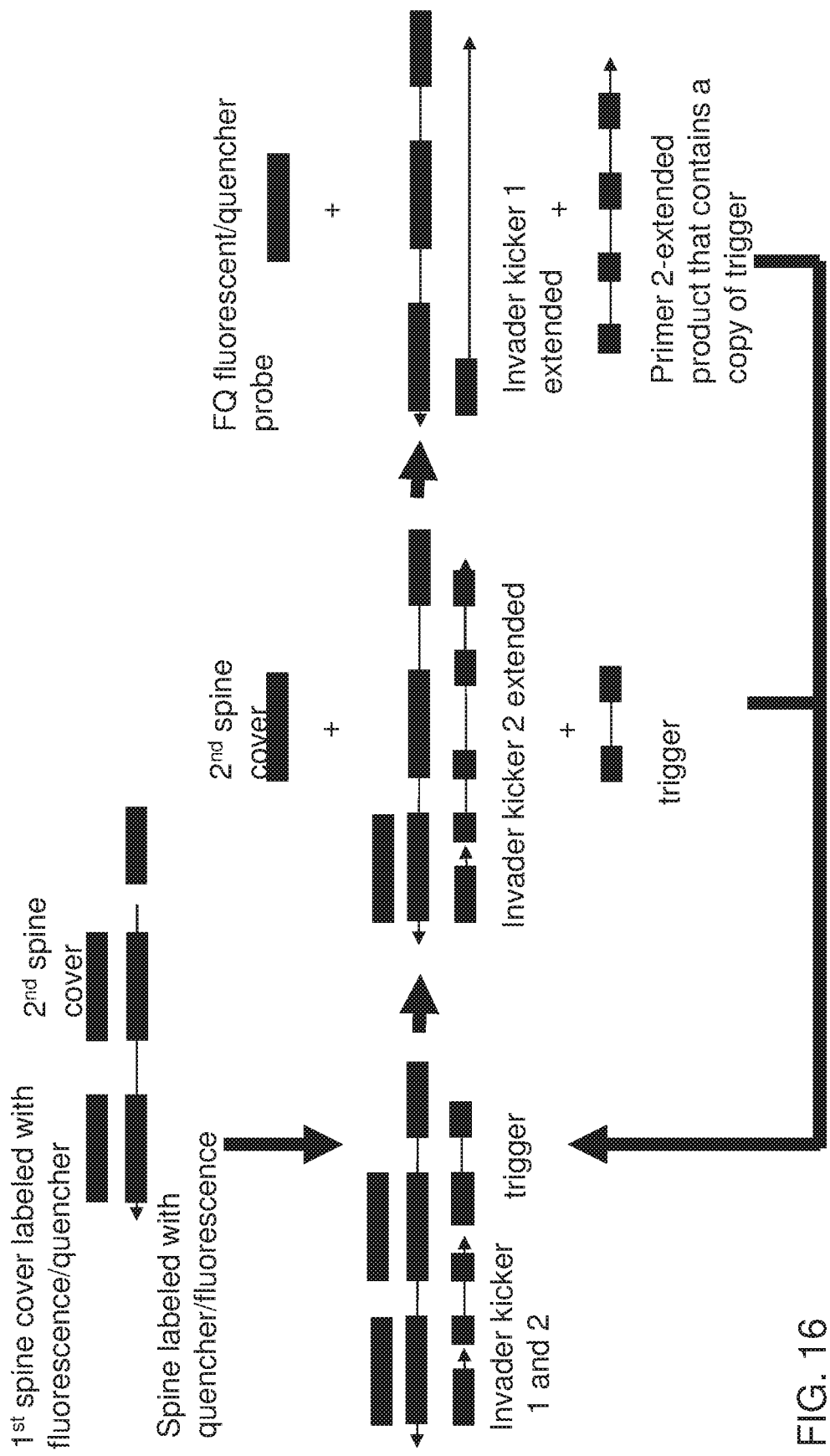
FIG. 16 shows an exemplary implementation of an exponential signal detection method in foldback primer amplification using one type of universal detection probes systems containing two spine covers. The spine is labeled with fluorescence or quencher at the 3' end and correspondingly the 1st spine cover hybridized with spine is labeled with quencher or fluorescence at its 5' end. A single-stranded specific probe or reverse complementary of specific probe generated from the reaction serves as the invader trigger and displaces the 2nd spine cover with the help from the invader kicker 2. Extension of invader kicker 2 leads to not only displacement of the trigger, but also separation of the 1 st spine cover from the spine with the help from the invader kicker 1, which in turn leads to separation of fluorescent dye from quencher to generate signal. The trigger from the reaction and the extended product of invader kicker 2 can therefore be used in the next round of signal generation.

Universal Detection Probes with an Additional Spine Cover and a Second Invader Kicker can be Used as a Signal Amplification and Detection Method Universal detection probes with an additional spine cover and a second universal primer were utilized to detect an invader trigger in a real-time isothermal reaction using the format as shown in FIG. 16. Reaction were carried out in a 25 ul reaction containing 20 mM Tris-HCl, 10 mM (NH4)2SO4, 10 mM KCl, 4 mM MgSO4, 0.1% Triton X-1.00, 0.4 mM each dNTP, 0.2 M Betaine, 0.1 µM spine sequence (SEQ ID NO: 47), 0.1 µM spine cover 1 (SEQ ID NO: 48), 0.1 µM spine cover 2 (SEQ ID NO: 53), 0.1 µM universal primer 1 (SEQ ID NO: 79), 0.1 µM universal primer 2 (SEQ ID NO: 80), 8 Units of Bst DNA polymerase Large Fragment (New England Biolabs) and various concentration of invader trigger (SEQ ID NO: 81) as the target. Spine sequence and spine covers were mix together before invader kicker and polymerase were added.

The reaction was carried out at 60° C. for 60 minutes with FAM fluorescence measured at 60 second interval in an AIM StepOne Real-time PCR Instrument.

(SEQ ID NO: 78)
5'-ACGATCGCACCTGTCGCACG-TTTT (SEQ ID NO: 79)
5'-CAGCCACTCCGC (SEQ ID NO: 80)
5'-GTCCACGC-ACGA (SEQ ID NO: 81)
5'-GCACCTGTCGCACGGTTGGACGCACTCAGGCT

Example 10

Figure 17:
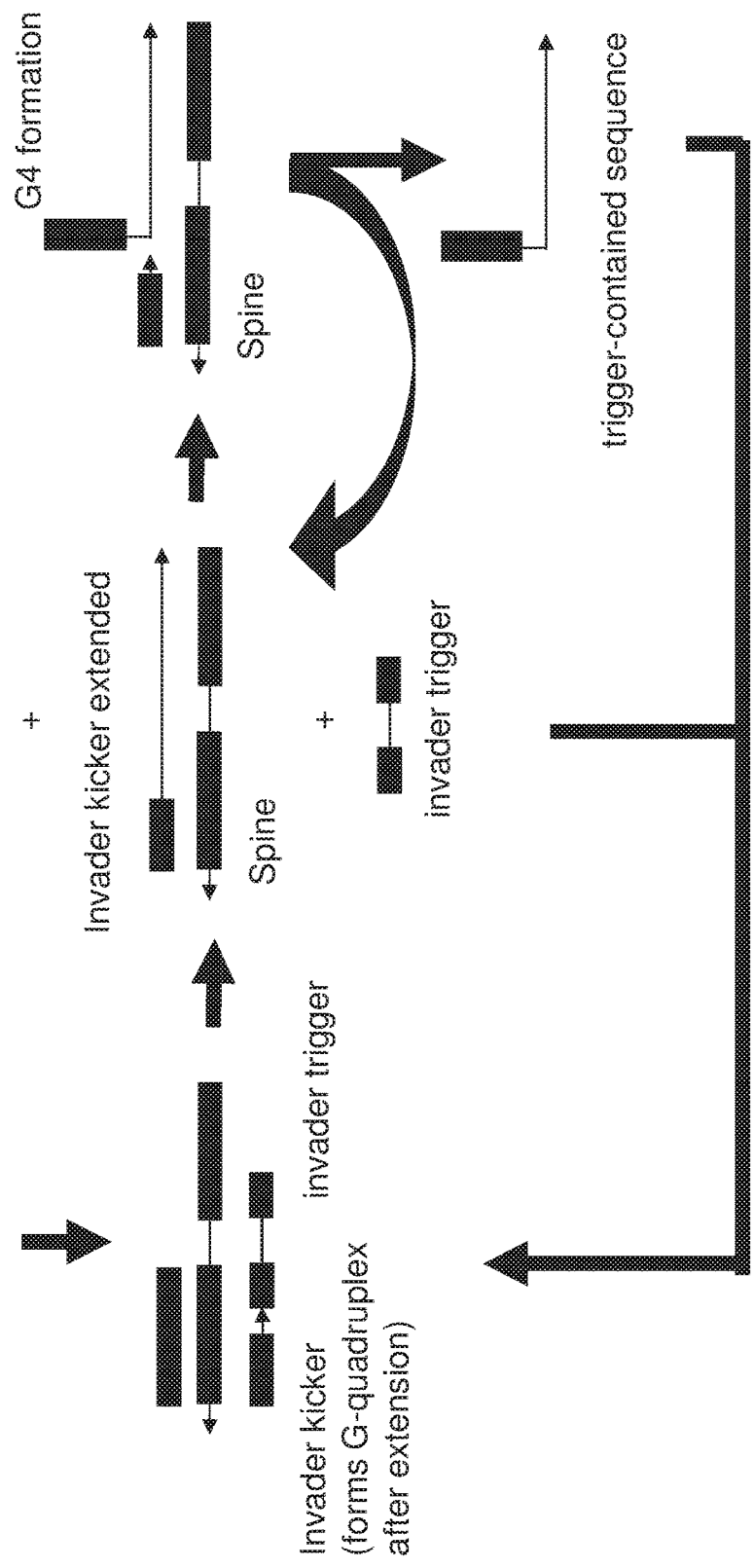
FIG. 17 shows an exemplary implementation of a G-quadruplex motif mediated exponential signal detection method in foldback primer amplification using one type of universal detection probe systems. Spine is labeled with fluorescence or quencher at the 3' end and correspondingly the spine cover hybridized with spine is labeled with quencher or fluorescence at its 5' end, A single-stranded specific probe or reverse complementary of specific probe generated from the reaction serves as the invader trigger and displaces the spine cover with the help from the invader kicker to generate fluorescence. The invader kicker contains a partial G-quadruplex forming sequence and the extension of invader kicker along the spine completes the full G-quadruplex sequence and leads G-quadruplex formation, which in turn allows another invader kicker to hybridize with the spine and to displace the G-quadruplex-contained elongated product. The trigger from the reaction and the G-quadruplex-contained extended product of invader kicker can therefore be used in the next round of signal generation.

Universal Detection Probes can be Applied Together with a G-Quadruplex Motif Mediated Exponential Signal Detection Method Universal detection probes with G-quadruplex motif mediated exponential signal detection mechanism were utilized to detect an invader trigger in a real-time isothermal reaction using the format as shown in FIG. 17. Reaction were carried out in a 25 ul reaction containing 20 mM Tris-HCl, 10 mM $(NH_4)_2SO_4$, 10 mM KCl, 4 mM $MgSO_4$, 0.1% Triton X-100, 0.4 mM each dNTP, 0.2 M Betaine, 0.1 µM spine sequence (SEQ ID NO: 82), 0.1 µM spine cover (SEQ ID NO: 83), 0.1 µM invader kicker (SEQ ID NO: 84), 8 Units of Bst DNA polymerase Large Fragment (New England Biolabs) and various concentration of invader trigger (SEQ ID NO: 50) as the target. Spine sequence and spine cover were mix together before invader kicker and polymerase were added. The reaction was carried out at 60° C. for 60 minutes with FAM fluorescence measured at 60 second interval in an ABI StepOne Real-time PCR Instrument.

(SEQ ID NO: 82)
5'-GAGTGCGTCCAACCGTGCGACAGGTGCGAT-CGTGCGTGGACCCT-CCCACCCACCCTC-BHQ (SEQ ID NO: 83)
5'-Fam-GAGGGTGGGTGGG-AGGGTCCACGCACG-TAA (SEQ ID NO: 84)
5'-GG-GAGGGTGGGTG

Example 11

Figure 18:
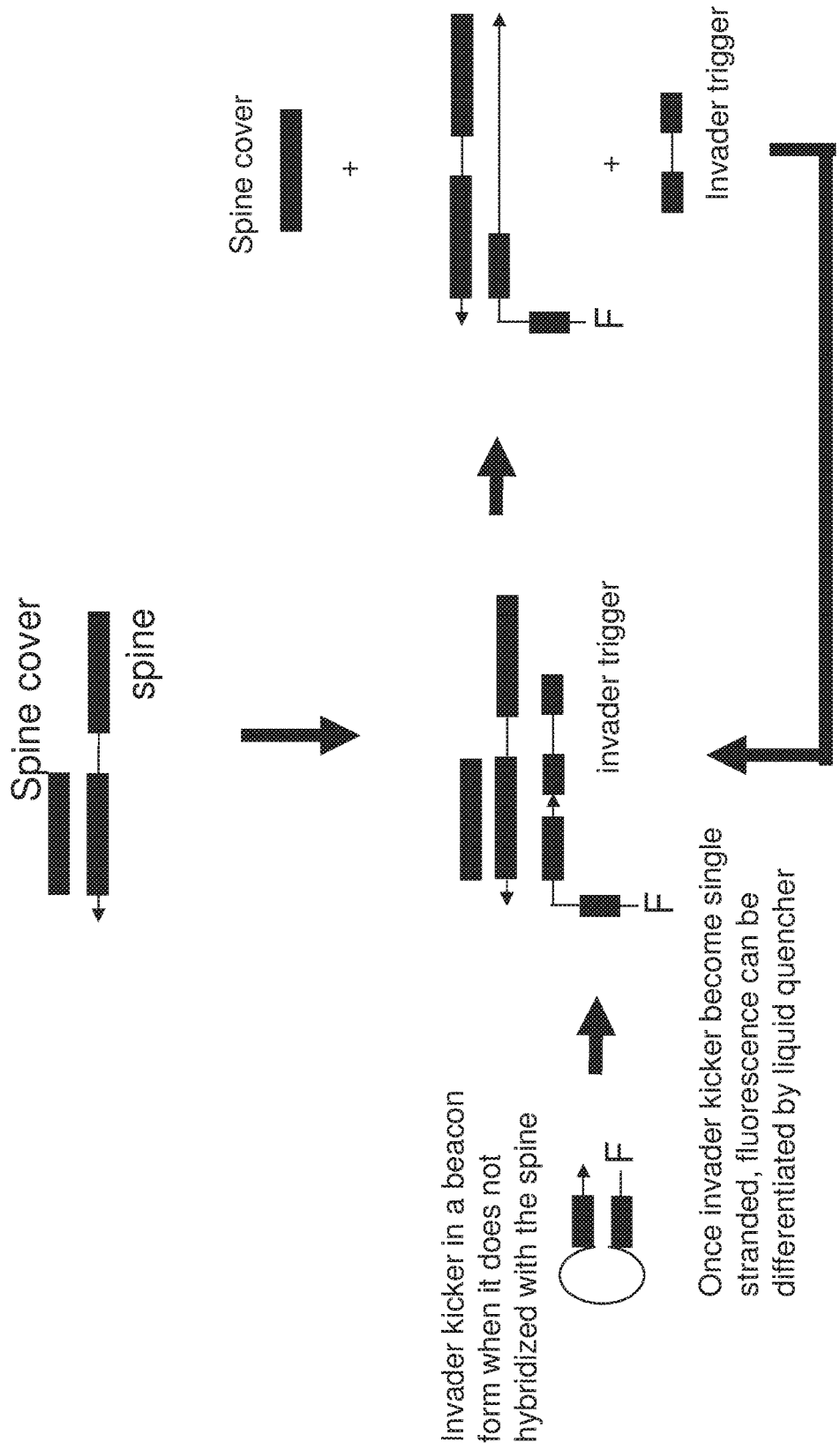
FIG. 18 shows an exemplary implementation of a signal detection method in foldback primer amplification using one type of universal detection probe system featuring signal generation from the invader kicker. When invader trigger is not active in the system, invader kicker forms a molecular beacon structure. Fluorescence labeled at its 5' end is quenched either by liquid quencher or by a quenching dye internally labeled near its 3' end. When the invader trigger becomes available, it displaces the cover with the invader kicker. During this process, invader kicker becomes linear and gets extended, leaving the 5' portion single stranded, which leads to increase of fluorescent signal. The invader trigger gets displaced by invader kicker extension and can therefore be used in the next round of signal generation.

Universal Detection Probes with a Fam-Labeled, Molecular Beacon-Formed Invader Kicker can be Used as a Signal Amplification and Detection Method Universal detection probes with a Fam-labeled, molecular beacon (MB)-formed universal primer were utilized to detect an invader trigger in a real-time isothermal reaction using the format as shown in FIG. 18. Reaction were carried out in a 25 ul reaction containing 20 mM Tris-HCl, 10 mM (NH4)2SO4, 10 mM KCl, 4 mM MgSO4, 0.1% Triton X-100, 0.4 mM each dNTP, 0.2 M Betaine, 6.25 µg/ml methylene blue as liquid quencher, 0.1 µM spine sequence (SEQ ID NO: 60), 0.12 µM spine cover (SEQ ID NO: 61), 0.1 µM MB-formed invader kicker (SEQ ID NO: 62-C3 spacer-SEQ ID NO: 85), 8 Units of Bst DNA polymerase Large Fragment (New England Biolabs) and various concentration of invader trigger (SEQ ID NO: 50) as the target. Spine sequence and spine cover were mix together before invader kicker and polymerase were added. The reaction was carried out at 60° C. for 60 minutes with FAM fluorescence measured at 60 second interval in an ABI StepOne Real-time PCR Instrument.

(SEQ ID NO: 60)
5'-AGCCTGAGTGCGTCCAACCGTGCGACAGGTGCGATCGTGCGTGGACCCTG CGGAGTGGCTGTG (SEQ ID NO: 61)
5'-CACAGCCACTCCGCAGGGTCCACGC-TT

5'-Fam-GCGGA-C3 spacer-CACAGCCACTCCGC (SEQ ID NO: 62-C3 spacer-SEQ ID NO: 85)

Example 12

Figure 19:
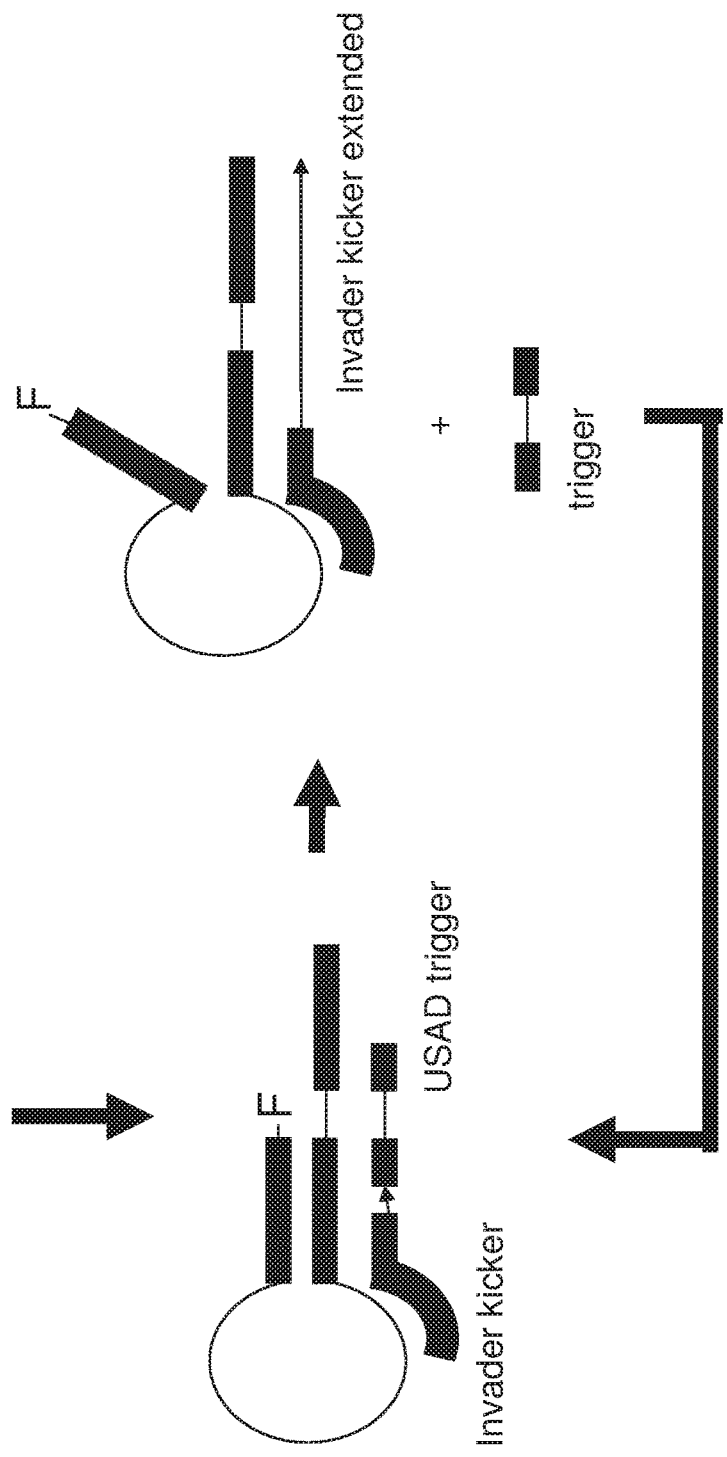
FIG. 19 shows an exemplary implementation of a signal detection method in foldback primer amplification using one type of universal detection probe system featuring a probe containing both spine and cover. Fluorescent dye is labeled at 3' end functioning with intercalating quencher dye, or self quencher primer (nucleic acid research 2002, vol 30, No 9, e37), both of which allows lower fluorescent signal whereby cover portion and spine portion are hybridized with each other to form a hairpin-loop structure. Presence of invader trigger leads to extension of universal primer along the spine all the way to the 5' end of the spine-cover probe and displacement of the cover portion. Single strand tagged with fluorescent dye showed increased fluorescent signal by intercalating quencher dye or self quencher primer (nucleic acid research 2002, vol 30, No 9, e37).

Universal Detection Probes with Spine and Cover Sequence in One Oligo can be Used as a Signal Amplification and Detection Method Universal detection probes with spine and cover sequence in one oligo were utilized to detect an invader trigger in a real-time isothermal reaction using the format as shown in FIG. 19. Reaction were carried out in a 25 ul reaction containing 20 mM. Tris-HCl, 10 mM (NH4)2SO4, 10 mM KCl, 4 mM MgSO4, 0.1% Triton X-100, 0.4 mM each dNTP, 0.2 M Betaine, 6.25 µg/ml methylene blue as liquid quencher, 0.1 µM spine-cover sequence (SEQ ID NO: 63), 0.2 µM invader kicker (SEQ ID NO: 64), 8 Units of Bst DNA polymerase Large Fragment (New England Biolabs) and various concentration of invader trigger (SEQ ID NO: 65) as the target. The reaction was carried out at 60° C. for 60 minutes with FAM fluorescence measured at 60 second interval in an ABI StepOne Real-time PCR Instrument.

(SEQ ID NO: 63)
5'-CCACGAGTGCCAGTGCGTC-CAACGCGTCGACAGGTGCGATCGT-GATCTCTCGTTAT-GCGGAGTGGCTGTG-ATCCGC-ATAACGAGAGA/T-FAM/CTT (SEQ ID NO: 64)
5'-CAGCCAC-TCCGC (SEQ ID NO: 65)
5'-ATAACGAGAGATC-ACGATCGCACCTGTCGACGCGTTG

Example 13

Figure 20:
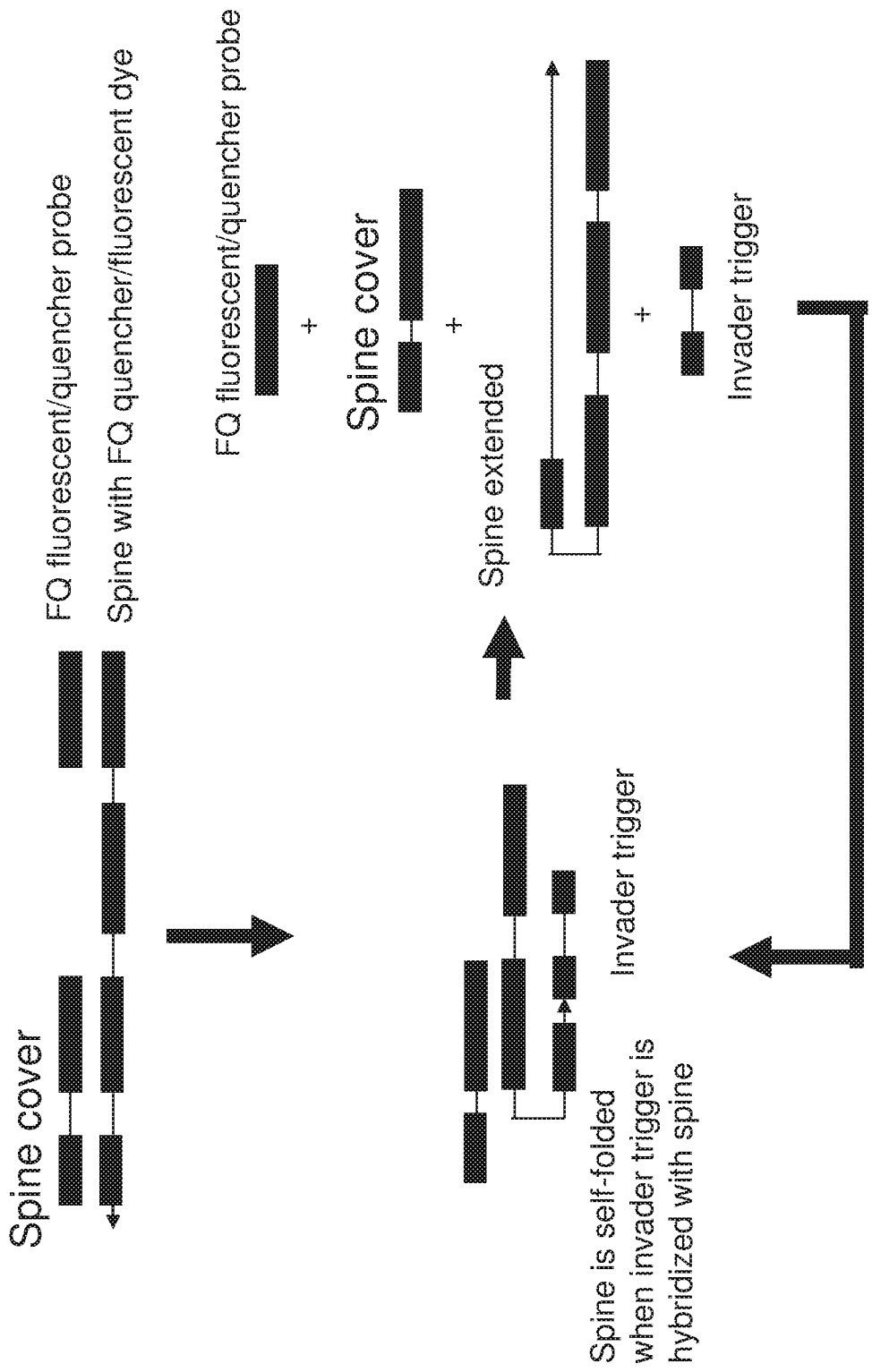
FIG. 20 shows an exemplary implementation of a signal detection method in foldback primer amplification using one type of universal detection probe system featuring a spine that is capable of self-priming when it is not hybridized with a spine cover. Presence of invader trigger leads to displacement of the cover and self-priming of the spine. Extension of the spine along itself leads to generation of signal as well as recycling of invader trigger for the next round.

Universal Detection Probes with a Self-Priming Spine can be Used as a Signal Amplification and Detection Method Universal detection probes with a self-priming spine were utilized to detect an invader trigger in a real-time isothermal reaction using the format as shown in FIG. 20. Reaction were carried out in a 25 ul reaction containing 20 mM Tris-HCl, 10 mM (NH4)2SO4, 10 mM KCl, 4 mM MgSO4, 0.1% Triton X-100, 0.4 mM each dNTP, 0.2M Betaine, 0.1 µM spine sequence (SEQ ID NO: 66), 0.11 µM quencher probe (SEQ ID NO: 67), 0.12 µM spine cover (SEQ ID NO: 68), 8 Units of Bst DNA polymerase Large Fragment (New England. Biolabs) and various concentration of invader trigger (SEQ ID NO: 69) as the target. Spine sequence, spine cover and quencher probe were mix together before polymerase were added. The reaction was carried out at 60° C. for 60 minutes with FAM fluorescence measured at 60 second interval in an ABI StepOne Real-time PCR Instrument.

(SEQ ID NO: 66)
5'-Fam-GCGTGGACCCTGCGGAGTGGCTGTG-AT-CACTCCCTCCAACCCTCCCACACCTCCCATCCT-CCCTCCACCCT-GAGCTA-CACATC-TAGCTC (SEQ ID NO: 67)
5'-CACAGCCACTCCGCAGGGTCCACGC-BHQ (SEQ ID NO: 68)
5'-GAGCTAGATGTGTAGCTCAGGGTGGAGGGAGGATGGGAG-TTT (SEQ ID NO: 69)
5'-AGGGTGGAGGGAGGATGGGAGGTGTGGGAGGGTTGGAGGGA-TTT

Example 14

Figure 21:
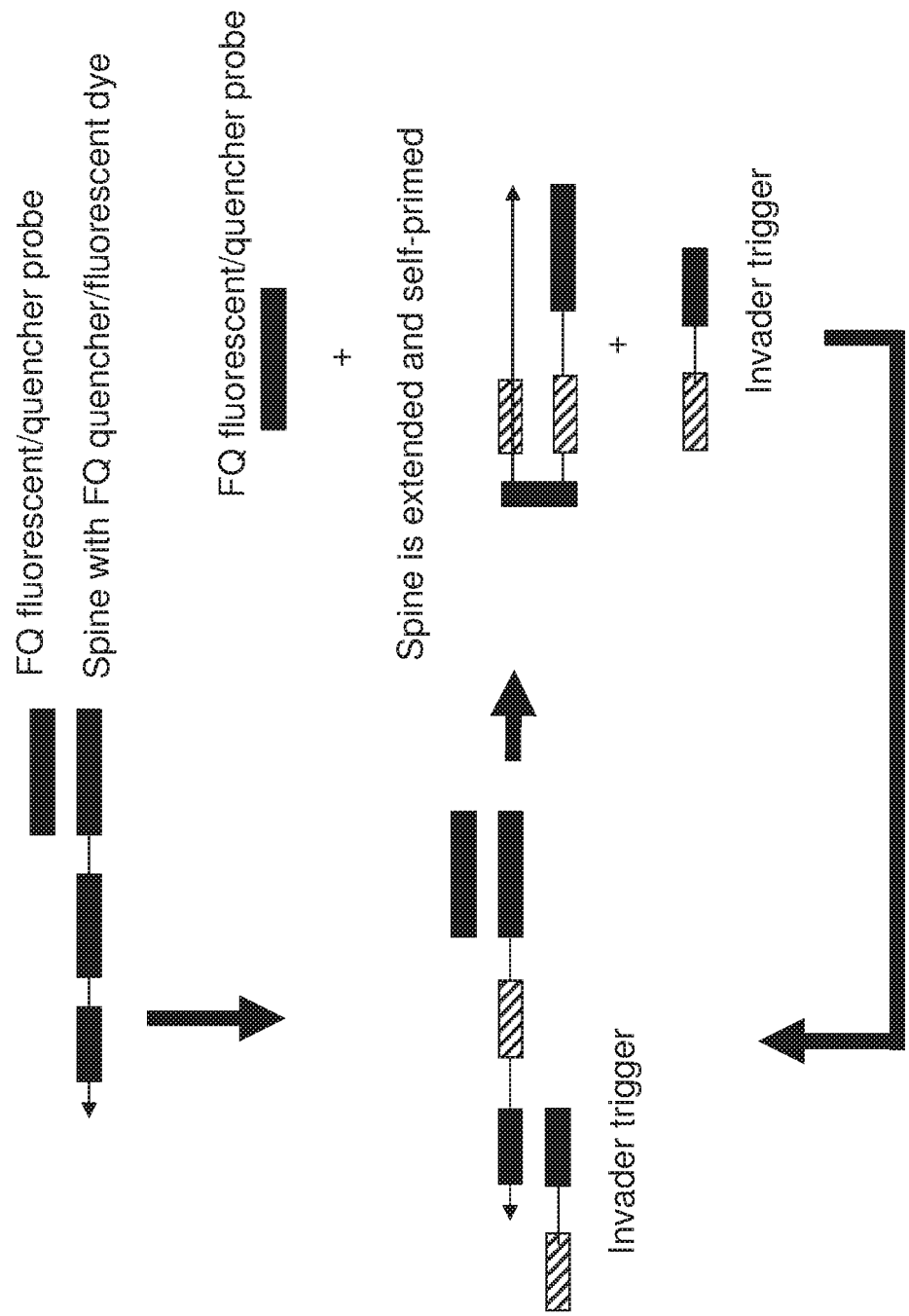
FIG. 21 shows an exemplary implementation of a signal detection method in foldback primer amplification using one type of universal detection probe system featuring a spine that is capable of self-priming after extension along the invader trigger. When the invader trigger is present in the system, it serves as a template for the spine. Extension of the spine along the invader trigger generates the sequence that can be folded back onto its reverse complementary sequence located on the spine. Therefore, FQ fluorescent/quencher probe is displaced and signal is generated upon this self-folding and extension.

Universal Detection Probes Featuring a Spine that is Capable of Self-Priming after Extension along the Invader Trigger can be Used as a Signal Amplification and Detection Method Universal detection probes with a spine that is capable of self-priming after extension along the invader trigger were utilized to detect an invader trigger in a real-time isothermal reaction using the format as shown in FIG. 21. Reaction were carried out in a 25 ul reaction containing 20 mM Tris-HCl, 10 mM (NH4)2SO4, 10 mM KCl, 4 mM MgSO4, 0.1% Triton X-100, 0.4 mM each dNTP, 0.2 M Betaine, 0.1 µM spine sequence (SEQ ID NO: 70), 0.12 µM quencher probe (SEQ ID NO: 67), 8 Units of Bst DNA polymerase Large Fragment (New England Biolabs) and various concentration of invader trigger (SEQ ID NO: 71) as the target. Spine sequence and quencher probe were mix together before polymerase was added. The reaction was carried out at 60° C. for 60 minutes with FAM fluorescence measured at 60 second interval in an ABI StepOne Real-time PCR Instrument.

(SEQ ID NO: 70)
5'-Fam-GCGTGGACCCTGCGGAGTGGCTGTG-AT-
GCATGCACGATCGCACCTGTCGCAC-GAGTCCTCCCAACC (SEQ ID NO: 71)
5'-GCATGCACGATCGCACCTGTCGCACGGTTGGGAGGACTC-TAT

Example 15

Figure 22:
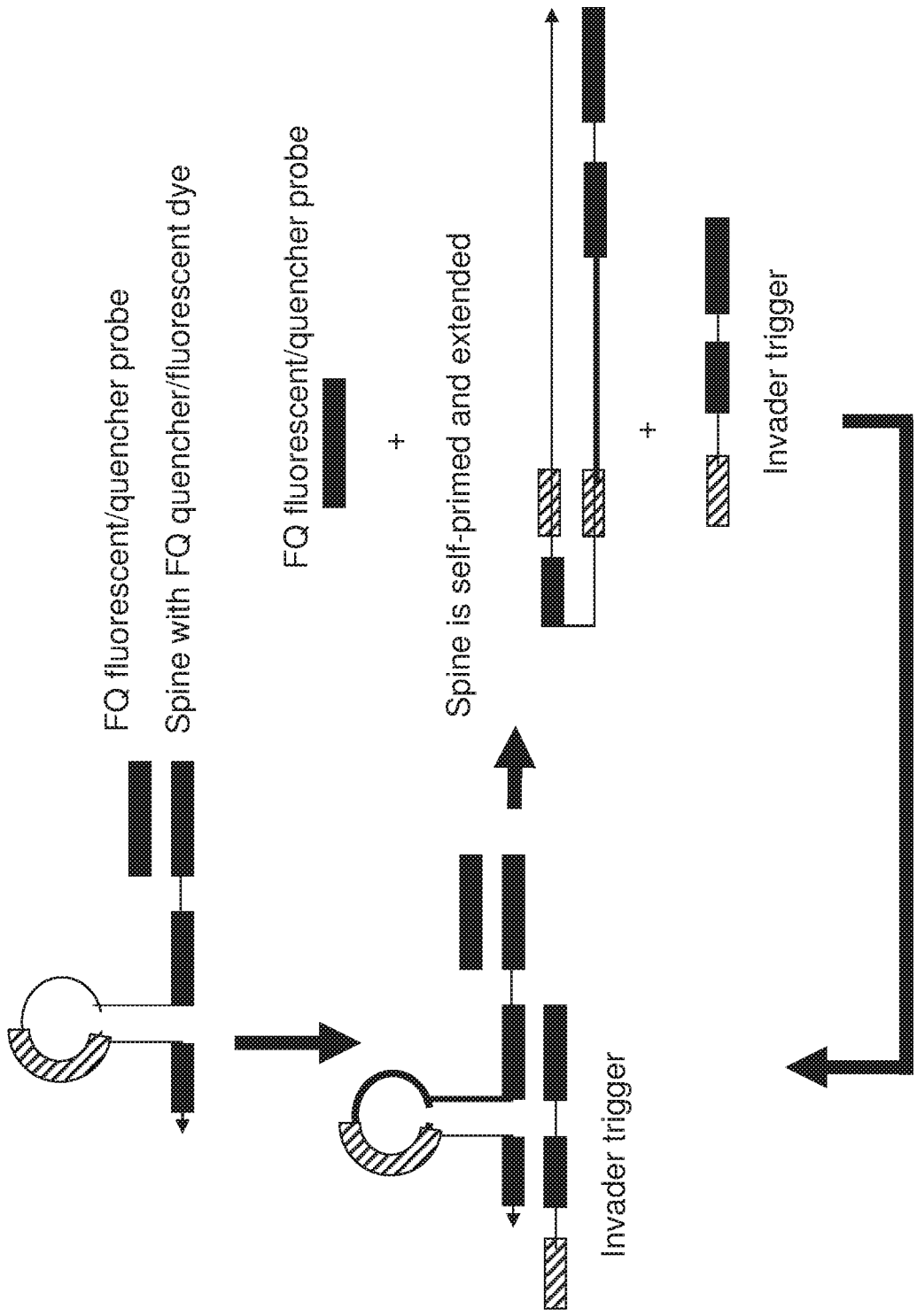
FIG. 22 shows an exemplary implementation of a signal detection method in foldback primer amplification using one type of universal detection probe system featuring an alternative design of a spine that is capable of self-priming after extension along the invader trigger. The spine contains a stem-loop structure within the invader trigger binding region. When the invader trigger is present in the system, it serves as a template for the spine. Extension of the spine along the invader trigger generates the sequence that can be folded back onto its reverse complementary sequence located in the loop region. Therefore, FQ fluorescent/quencher probe is displaced and signal is generated upon this self-folding and extension.

Universal Detection Probes Featuring a Hairpin-Structured Spine that is Capable of Self-Priming after Extension along the Invader Trigger can be Used as a Signal Amplification and Detection Method Universal detection probes featuring an alternative design of a spine that is capable of self-priming after extension along the invader trigger were utilized to detect an invader trigger in a real-time isothermal reaction using the format as shown in FIG. 22. Reaction were carried out in a 25 ul reaction containing 20 mM Tris-HCl, 10 mM (NH4)2SO4, 10 mM KCl, 4 mM MgSO4, 0.1% Triton X-100, 0.4 mM each dNTP, 0.2 M Betaine, 0.1 µM spine sequence (SEQ ID NO: 72), 0.12 µM quencher probe (SEQ ID NO: 67), 8 Units of Bst DNA polymerase Large Fragment (New England Biolabs) and various concentration of invader trigger (SEQ ID NO: 73) as the target. Spine sequence and quencher probe were mix together before polymerase was added. The reaction was carried out at 60° C. for 60 minutes with FAM fluorescence measured at 60 second interval in an ABI StepOne Real-time PCR Instrument.

(SEQ ID NO: 72)
5'-Fam-GCGTGGACCCTGCGGAGTGGCTGTG-AT-
GCCGAGAGTCCTCCCAACCGTCTGT-AGCGAGAC-ATAT-GTCGCAC-
GTCTCGCA-TCCCAC (SEQ ID NO: 73)
5'-GTCGCACGTGGGA-
ACAGACGGTTGGGAGGACTCTCGGC-/3phos/

Example 16

Example 16 shows an exemplary experiment result using universal detection probes in a real-time isothermal reaction based on the format as shown in FIG. 14. 0 nM (green), 0.8 nM (black). 8 nM (red), 80 nM (light blue) and 800 nM (dark blue) invader trigger was detected in a 25 ul reaction containing 0.1 µM spine sequence, 0.1 µM spine cover, 0.8 µM invader kicker. The reaction was carried out at 60° C. for 48 minutes with FAM fluorescence measured at 60 second interval in an ABI StepOne Real-time PCR instrument. FIGS. 23A and 23B shows comparison result of a LAMP reaction using universal detection probe as shown in FIG. 9 as compared to a LAMP reaction using universal FQ probe detection.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would he achieved. All such similar substitutes and modifications apparent to those skilled in the art are deemed to be within the spirit, scope and concept of the invention as defined by the appended claims.

The invention claimed is:

1. An omega amplification primer set comprising a first foldback primer and a second foldback primer that allow isothermal amplification under suitable omega amplification conditions of a portion of a target nucleic acid sequence, wherein the first foldback primer comprises a first extruding sequence at its 5' terminus or the second foldback primer comprises a second extruding sequence at its 5' terminus wherein the first extruding sequence or the second extruding sequence is at least 2 nucleotides in length and will not anneal to a template nucleic acid and cannot hybridize to a first strand or a complementary strand of the target nucleic acid sequence.

2. The omega amplification primer set of claim 1, wherein:
   (i) the target nucleic acid sequence has a first strand, wherein the first strand is complementary to a complementary strand;
   (ii) the first foldback primer includes from 5' to 3':
      (1-b) a sequence (F1c), wherein the sequence (F1c) hybridizes to a sequence (F1T) in the complementary strand of the target nucleic acid sequence; and
      (1-c) at the 3' terminus, a sequence (F2), wherein the sequence (F2) hybridizes to a sequence (F2cT) in the first strand of the target nucleic acid sequence,
      wherein the sequence (F1T) is 3' of a sequence (F2T) in the complementary strand; and the sequence (F2T) is complementary to the sequence (F2cT);
   (iii) the second foldback primer includes from 5' to 3':
      (2-b) a second sequence comprising: a sequence (R1c), wherein the sequence (R1c) hybridizes to a sequence (R1T) in the first strand of the target nucleic acid sequence,
      (2-c) at the 3' terminus, a sequence (R2), wherein the sequence (R2) hybridizes to a sequence (R2cT) in the complementary strand of the target nucleic acid sequence, wherein the sequence (R1T) is 3' of a sequence (R2T) in the first strand; and the sequence (R2T) is complementary to the sequence (R2cT); and (iv) the primer set further comprises:
(X) (1-a) a first extruding sequence at the 5' terminus of the first foldback primer, wherein the first extruding sequence is at least 4 nucleotides and cannot hybridize to the first strand or the complementary strand, and wherein the sequence (R1c) is at the 5' terminus of the second foldback primer;
(Y) (2-a) a second extruding sequence at the 5' terminus of the second foldback primer, wherein the second extruding sequence is at least 4 nucleotides and cannot hybridize to the first strand or the complementary strand, and wherein the sequence (F1c) is at the 5' terminus of the first foldback primer; or
(Z) (1-a) a first extruding sequence at the 5' terminus of the first foldback primers, wherein the first extruding sequence is at least 4 nucleotides and cannot hybridize to the first strand or the complementary strand, and (2-a) a second extruding sequence at the 5' terminus of the second primer, wherein the second extruding sequence is at least 4 nucleotides and cannot hybridize to the first strand or the complementary strand.

3. The omega amplification primer set of claim 2, wherein a portion of the sequence (F1c) can hybridize to a portion of the sequence (R1c).

4. The omega amplification primer set of claim 2, wherein the sequence (F1c) and the sequence (R1c) overlap by at least 1, 2, 3, 4, 5, 6, 7, 8, 9, 10, 12, 14, 16, 18, 20, 25, or 30 nucleotides.

5. The omega amplification primer set of claim 1, wherein the first extruding sequence or the second extruding sequence is at least 3, 4, 5, 6, 7, 8, 9, 10, 12, 14, 16, 18, 20, 25, 30, 35, 40, 45, 50, 60, 70, 80, 90, 100, 150, or 200 nucleotides.

6. The omega amplification primer set of claim 1, wherein the first extruding sequence or the second extruding sequence is less than 500, 450, 400, 350, 300, 250, 200, 150, 100, 90, 80, 70, 60, 50, 45, 40, 35, 30, 25, or 20 nucleotides.

7. The omega amplification primer set of claim 1, wherein the first extruding sequence or the second extruding sequence is 3 to 100 nucleotides, 3 to 75 nucleotides, 3 to 50 nucleotides, or 4 to 30 nucleotides in length.

8. The omega amplification primer set of claim 1, wherein the first extruding sequence or the second extruding sequence comprises a G-quadruplex, an aptamer sequence, an RNA promoter sequence, a nicking sequence, or an FQ detection sequence.

9. The omega amplification primer set of claim 1, wherein the first extruding sequence or the second extruding sequence is G rich.

10. The omega amplification primer set of claim 1, wherein the omega amplification reaction comprises one or more than one kicker accelerator primers, or one or more than one stem accelerator primers, or one or more than one loop accelerator primers.

11. The omega amplification primer set of claim 1, wherein the kicker accelerator primer or loop accelerator primer or stem accelerator primer comprises folding sequences at its 5' end to fold onto its 3' end downstream sequences after 3' end is extended by a polymerase.

12. The omega amplification primer set of claim 1, wherein the first extruding primer or the second extruding primer has hairpin structure at its 5' terminus.

13. The omega amplification primer set of claim 1, wherein foldback primer includes unnatural nucleotides.

14. A method of generating amplicon nucleic acids from a template nucleic acid in a sample using an omega amplification reaction comprising
(i) combining the sample with the set of omega amplification primers of claim 1, and a strand displacement amplification polymerase; and
(ii) generating amplicon nucleic acids by maintaining the combination under suitable omega amplification conditions.

15. A method of making an amplicon nucleic acid from a target nucleic acid molecule, wherein the amplicon nucleic acid is capable of forming a first stem and loop at a first end, is capable of forming either a second stem and loop or a foldback loop at a second end, and has (i) the first extruding sequence located at the terminus of the first end, and/or (ii) the second extruding sequence located at the terminus of the second end, the method comprising:
(a) combining a sample with the target nucleic acid molecule with the set of primers of any one of claim 2;
(b) annealing the sequence (F2) of the first primer to the sequence (F2cT) in the first strand of the target nucleic acid molecule;
(c) extending the first primer from its 3' end, using a suitable polymerase, to form a first single-stranded nucleic acid molecule comprising the first primer at the 5' end and the sequence (R2cT);
(d) displacing the first single-stranded nucleic acid molecule from the target nucleic acid sequence;
(e) annealing the sequence (R2) of the second primer to the sequence (R2cT) in the first single-stranded nucleic acid molecule; and
(f) making the replicated portion of the target nucleic acid molecule by extending the second primer from its 3' end, using a suitable polymerase, to form a second single-stranded nucleic acid molecule comprising the second primer at the 5' end and a sequence complementary to the first primer;
wherein the displacing step (d) is carried out by:
(i) annealing the sequence (F2) of an additional first primer to the sequence (F2cT) in the first strand of the target nucleic acid molecule and extending the additional first primer from its 3' end, using a suitable polymerase, to displace the first single-stranded nucleic acid molecule;
(ii) steps (d) and (e); or
(iii) (1) providing a first kicker primer comprising, at its 3' terminus, a sequence (F3), wherein the sequence (F3) hybridizes to a sequence (F3cT) and the sequence (F3cT) is 5' of the sequence (F2cT) in the first strand of the target nucleic acid sequence;
(2) annealing the sequence (F3) in the first kicker primer to the sequence (F3cT) in the first strand of the target nucleic acid molecule; and
(3) extending the first kicker primer from its 3' end, using a suitable polymerase, to displace the first single-stranded nucleic acid molecule.

16. A kit comprising the set of primers of claim 1.

17. An amplicon nucleic acid derived from a target nucleic acid sequence comprising from 5' to 3':
(2) a second sequence comprising a sequence (R1c);
(3) a sequence (R2), wherein the sequence (R2) hybridizes to a sequence (R2cT) in a complementary strand of the target nucleic acid sequence;
(4) a sequence (R1T), wherein the sequence (R1T) hybridizes to the sequence (R1c);

(5) a sequence (F1cT);
(6) a sequence (F2c), wherein the sequence (F2c) hybridizes to a sequence (F2T) in the complementary strand of the target nucleic acid sequence; and
(7) a sequence (F1), wherein the sequence (F1) hybridizes to (F1cT) wherein the nucleic acid further comprises:
  (X) (8) a first extruding sequence at the 3' terminus, wherein the first extruding sequence is at least 4 nucleotides and cannot hybridize to the template nucleic acid or its complement, and wherein the sequence (R1c) is at the 5' terminus;
  (Y) (1) a second extruding sequence at the 5' terminus, wherein the second extruding sequence is at least 4 nucleotides and cannot hybridize to the template nucleic acid or its complement, and wherein the sequence (F1) is at the 3' terminus; or (Z) (8) a first extruding sequence at the 3' terminus, wherein the first extruding sequence is at least 4 nucleotides and cannot hybridize to the template nucleic acid or its complement, and (1) a second extruding sequence at the 5' terminus, wherein the second extruding sequence is at least 4 nucleotides and cannot hybridize to the template nucleic acid or its complement.

* * * * *

SEQUENCE LISTING

```
<160> NUMBER OF SEQ ID NOS: 86

<210> SEQ ID NO 1
<211> LENGTH: 42
<212> TYPE: DNA
<213> ORGANISM: Artificial Sequence
<220> FEATURE:
<223> OTHER INFORMATION: Synthetic Construct

<400> SEQUENCE: 1
acgtctggcc gtaggtcttt gcagctacag cacacccct ca                42

<210> SEQ ID NO 2
<211> LENGTH: 52
<212> TYPE: DNA
<213> ORGANISM: Artificial Sequence
<220> FEATURE:
<223> OTHER INFORMATION: Synthetic Construct

<400> SEQUENCE: 2
tttttttttt acgtctggcc gtaggtcttt gcagctacag cacacccct ca      52

<210> SEQ ID NO 3
<211> LENGTH: 47
<212> TYPE: DNA
```

```
<213> ORGANISM: Artificial Sequence
<220> FEATURE:
<223> OTHER INFORMATION: Synthetic Construct

<400> SEQUENCE: 3
tgctacacga cctggacact gtggatgtag gtgtagctgc accgaga                    47

<210> SEQ ID NO 4
<211> LENGTH: 57
<212> TYPE: DNA
<213> ORGANISM: Artificial Sequence
<220> FEATURE:
<223> OTHER INFORMATION: Synthetic Construct

<400> SEQUENCE: 4
tttttttttt tgctacacga cctggacact gtggatgtag gtgtagctgc accgaga         57

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
cggacacggt gctggaatac                                                  20

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
cattgtggac ctgtcaaccc a                                                21

<210> SEQ ID NO 7
<211> LENGTH: 59
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 7
cacagccact ccgcagggtc cacgcacgat cgcacctgca ttgtggacct gtcaaccca       59

<210> SEQ ID NO 8
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 38
<223> OTHER INFORMATION: Attached to BHQ group

<400> SEQUENCE: 8
caggtgcgat cgtgcgtgga ccctgcggag tggctgtg                              38

<210> SEQ ID NO 9
<211> LENGTH: 22
```

<212> TYPE: DNA
<213> ORGANISM: Artificial Sequence
<220> FEATURE:
<223> OTHER INFORMATION: Synthetic Construct

<400> SEQUENCE: 9
cggtatccgc tactcagctt gt                                           22

<210> SEQ ID NO 10
<211> LENGTH: 26
<212> TYPE: DNA
<213> ORGANISM: Artificial Sequence
<220> FEATURE:
<223> OTHER INFORMATION: Synthetic Construct

<400> SEQUENCE: 10
tgttaccact acagagtttc cgtctt                                       26

<210> SEQ ID NO 11
<211> LENGTH: 400
<212> TYPE: DNA
<213> ORGANISM: Artificial Sequence
<220> FEATURE:
<223> OTHER INFORMATION: Synthetic Construct

<400> SEQUENCE: 11
aatatgggaa cacaggtacg tgggaagtac attttgggaa taatgtaatt gattgtaatg    60
actctatgtg cagtaccagt gacgacacgg tatccgctac tcagcttgtt aaacagctac   120
agcacacccc ctcaccgtat tccagcaccg tgtccgtggg caccgcaaag acctacggcc   180
agacgtcggc tgctacacga cctggacact gtggactcgc ggagaagcag cattgtggac   240
ctgtcaaccc acttctcggt gcagctacac ctacaggcaa caacaaaaga cggaaactct   300
gtagtggtaa cactacgcct ataatacatt taaaaggtga cagaaacagt ttaaaatgtt   360
tacggtacag attgcgaaaa catagcgacc actatagaga                         400

<210> SEQ ID NO 12
<211> LENGTH: 52
<212> TYPE: DNA
<213> ORGANISM: Artificial Sequence
<220> FEATURE:
<223> OTHER INFORMATION: Synthetic Construct

<400> SEQUENCE: 12
ttttgaattc acgtctggcc gtaggtcttt gcagctacag cacccccct ca            52

<210> SEQ ID NO 13
<211> LENGTH: 69
<212> TYPE: DNA
<213> ORGANISM: Artificial Sequence
<220> FEATURE:
<223> OTHER INFORMATION: Synthetic Construct

<400> SEQUENCE: 13
tttttttttt tttttgaat tctgctacac gacctggaca ctgtggatgt aggtgtagct    60
gcaccgaga                                                          69

<210> SEQ ID NO 14
<211> LENGTH: 48
<212> TYPE: DNA
<213> ORGANISM: Artificial Sequence
<220> FEATURE:
<223> OTHER INFORMATION: Synthetic Construct

<400> SEQUENCE: 14
acgtctggcc gtaggtcttt gcgaattcag ctacagcaca ccccctca    48

<210> SEQ ID NO 15
<211> LENGTH: 62
<212> TYPE: DNA
<213> ORGANISM: Artificial Sequence
<220> FEATURE:
<223> OTHER INFORMATION: Synthetic Construct

<400> SEQUENCE: 15
tttttttttt actctcgttc agcttgtctg tctagatctt acatgttacg agtcattgga    60
ca    62

<210> SEQ ID NO 16
<211> LENGTH: 64
<212> TYPE: DNA
<213> ORGANISM: Artificial Sequence
<220> FEATURE:
<223> OTHER INFORMATION: Synthetic Construct

<400> SEQUENCE: 16
tttttttttt ttgtctgtct agatggctgt ctgtttcccg aaattgacct tacatgttac    60
gagt    64

<210> SEQ ID NO 17
<211> LENGTH: 61
<212> TYPE: DNA
<213> ORGANISM: Artificial Sequence
<220> FEATURE:
<223> OTHER INFORMATION: Synthetic Construct

<400> SEQUENCE: 17
tttttttttt gctgtctgtt tcatcctcat cctctggaaa ccaacaaccg aaattgacct    60
t    61

<210> SEQ ID NO 18
<211> LENGTH: 48
<212> TYPE: DNA
<213> ORGANISM: Artificial Sequence
<220> FEATURE:
<223> OTHER INFORMATION: Synthetic Construct

<400> SEQUENCE: 18
atctagacag acaagctgaa cgagagttgt tgctttcaat ggcaaggc    48

<210> SEQ ID NO 19
<211> LENGTH: 22
<212> TYPE: DNA
<213> ORGANISM: Artificial Sequence
<220> FEATURE:
<223> OTHER INFORMATION: Synthetic Construct

<400> SEQUENCE: 19
gtctgtttca tcctcatcct ct    22

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
ctcatcctct gagttgtcca                                            20

<210> SEQ ID NO 21
<211> LENGTH: 24
<212> TYPE: DNA
<213> ORGANISM: Artificial Sequence
<220> FEATURE:
<223> OTHER INFORMATION: Synthetic Construct

<400> SEQUENCE: 21
agttgtccaa tgactcgtaa catg                                       24

<210> SEQ ID NO 22
<211> LENGTH: 25
<212> TYPE: DNA
<213> ORGANISM: Artificial Sequence
<220> FEATURE:
<223> OTHER INFORMATION: Synthetic Construct

<400> SEQUENCE: 22
agaatagtta ctgactgcac gaagt                                      25

<210> SEQ ID NO 23
<211> LENGTH: 63
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 23
cacagccact ccgcagggtc cacgcacgat cgcacctgag aatagttact gactgcacga   60
agt                                                              63

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
ccttgcagga cattacttta gacct                                      25

<210> SEQ ID NO 25
<211> LENGTH: 26
<212> TYPE: DNA
<213> ORGANISM: Artificial Sequence
<220> FEATURE:
<223> OTHER INFORMATION: Synthetic Construct

<400> SEQUENCE: 25
acccataagc aactcttcta tcactc                                     26

<210> SEQ ID NO 26
<211> LENGTH: 288
<212> TYPE: DNA
<213> ORGANISM: Artificial Sequence
<220> FEATURE:
<223> OTHER INFORMATION: Synthetic Construct

<400> SEQUENCE: 26

```
aagatgcatg gaaaaaaaac aaccttgcag gacattactt tagacctgaa accaacaacc      60
gaaattgacc ttacatgtta cgagtcattg gacaactcag aggatgagga tgaaacagac     120
agccatctag acagacaagc tgaacgagag tgttacagaa tagttactga ctgcacgaag     180
tgtcagtgca cagtatgcct tgccattgaa agcaacaaag ctgatttaag agtgatagaa     240
gagttgctta tgggtacact aggtattgtg tgccccaact gttccaga                  288
```

<210> SEQ ID NO 27
<211> LENGTH: 48
<212> TYPE: DNA
<213> ORGANISM: Artificial Sequence
<220> FEATURE:
<223> OTHER INFORMATION: Synthetic Construct

<400> SEQUENCE: 27

```
cgaacgttgc tgtcacatcc acagtggacg gacaagattc acaacctt                   48
```

<210> SEQ ID NO 28
<211> LENGTH: 45
<212> TYPE: DNA
<213> ORGANISM: Artificial Sequence
<220> FEATURE:
<223> OTHER INFORMATION: Synthetic Construct

<400> SEQUENCE: 28

```
gagaagtgca acagcttctg ttgggctgaa tcgtccgcca tcgtt                      45
```

<210> SEQ ID NO 29
<211> LENGTH: 67
<212> TYPE: DNA
<213> ORGANISM: Artificial Sequence
<220> FEATURE:
<223> OTHER INFORMATION: Synthetic Construct

<400> SEQUENCE: 29

```
tttttttttt tttttttttt ttgagaagtg caacagcttc tgttgggctg aatcgtccgc      60
catcgtt                                                                67
```

<210> SEQ ID NO 30
<211> LENGTH: 28
<212> TYPE: DNA
<213> ORGANISM: Artificial Sequence
<220> FEATURE:
<223> OTHER INFORMATION: Synthetic Construct

<400> SEQUENCE: 30

```
caacaggtca ctatttggta atgttgtt                                         28
```

<210> SEQ ID NO 31
<211> LENGTH: 57
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 31

```
cacagccact ccgcagggtc cacgcacgat cgcacctgca tctgcgcacc gaagaca         57
```

<210> SEQ ID NO 32
<211> LENGTH: 19

```
<212> TYPE: DNA
<213> ORGANISM: Artificial Sequence
<220> FEATURE:
<223> OTHER INFORMATION: Synthetic Construct

<400> SEQUENCE: 32
catctgcgca ccgaagaca                                                    19

<210> SEQ ID NO 33
<211> LENGTH: 27
<212> TYPE: DNA
<213> ORGANISM: Artificial Sequence
<220> FEATURE:
<223> OTHER INFORMATION: Synthetic Construct

<400> SEQUENCE: 33
gcaattagta gacagctcag aagatga                                           27

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
tgtacaccca gacccctcat                                                   20

<210> SEQ ID NO 35
<211> LENGTH: 313
<212> TYPE: DNA
<213> ORGANISM: Artificial Sequence
<220> FEATURE:
<223> OTHER INFORMATION: Synthetic Construct

<400> SEQUENCE: 35
ccctgtaggg ttacattgct atgagcaatt agtagacagc tcagaagatg aggtggacga       60
agtggacgga caagattcac aacctttaaa acaacattac caaatagtga cctgttgctg      120
tggatgtgac agcaacgttc gactggttgt gcagtgtaca gaaacagaca tcagagaagt      180
gcaacagctt ctgttgggaa cactaaacat agtgtgtccc atctgcgcac cgaagacata      240
acaacgatgg cggacgattc aggtacagaa aatgaggggt ctgggtgtac aggatggttt      300
atggtagaag cta                                                         313

<210> SEQ ID NO 36
<211> LENGTH: 47
<212> TYPE: DNA
<213> ORGANISM: Artificial Sequence
<220> FEATURE:
<223> OTHER INFORMATION: Synthetic Construct

<400> SEQUENCE: 36
aggctttggt atgggtctcg gtggtgcaca gaactatcca ctgctga                     47

<210> SEQ ID NO 37
<211> LENGTH: 43
<212> TYPE: DNA
<213> ORGANISM: Artificial Sequence
<220> FEATURE:
<223> OTHER INFORMATION: Synthetic Construct

<400> SEQUENCE: 37
ggcaccacag aaacgcagaa gacactgagt cgcactcgct tgg                         43
```

<210> SEQ ID NO 38
<211> LENGTH: 21
<212> TYPE: DNA
<213> ORGANISM: Artificial Sequence
<220> FEATURE:
<223> OTHER INFORMATION: Synthetic Construct

<400> SEQUENCE: 38
ggcgtgtagc tgtgtagcaa t                                     21

<210> SEQ ID NO 39
<211> LENGTH: 46
<212> TYPE: DNA
<213> ORGANISM: Artificial Sequence
<220> FEATURE:
<223> OTHER INFORMATION: Synthetic Construct

<400> SEQUENCE: 39
aggctttggt atgggtctcg gtggtggcgt gtagctgtgt agcaat          46

<210> SEQ ID NO 40
<211> LENGTH: 22
<212> TYPE: DNA
<213> ORGANISM: Artificial Sequence
<220> FEATURE:
<223> OTHER INFORMATION: Synthetic Construct

<400> SEQUENCE: 40
aatcacaaac gacttcgagg gg                                    22

<210> SEQ ID NO 41
<211> LENGTH: 46
<212> TYPE: DNA
<213> ORGANISM: Artificial Sequence
<220> FEATURE:
<223> OTHER INFORMATION: Synthetic Construct

<400> SEQUENCE: 41
ggcaccacag aaacgcagaa gacaaatcac aaacgacttc gagggg          46

<210> SEQ ID NO 42
<211> LENGTH: 30
<212> TYPE: DNA
<213> ORGANISM: Artificial Sequence
<220> FEATURE:
<223> OTHER INFORMATION: Synthetic Construct

<400> SEQUENCE: 42
gtaattgttt gtcctgaatc tgtatttagc                            30

<210> SEQ ID NO 43
<211> LENGTH: 19
<212> TYPE: DNA
<213> ORGANISM: Artificial Sequence
<220> FEATURE:
<223> OTHER INFORMATION: Synthetic Construct

<400> SEQUENCE: 43
gtcaacactg tccacggca                                        19

<210> SEQ ID NO 44
<211> LENGTH: 59
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: 1
<223> OTHER INFORMATION: Attached to FAM group

<400> SEQUENCE: 44
cacagccact ccgcagggtc cacgcacgat cgcacctggg cgtgtagctg tgtagcaat      59

<210> SEQ ID NO 45
<211> LENGTH: 57
<212> TYPE: DNA
<213> ORGANISM: Artificial Sequence
<220> FEATURE:
<223> OTHER INFORMATION: Synthetic Construct

<400> SEQUENCE: 45
tttttttttt aggctttggt atgggtctcg gtggtgcaca gaactatcca ctgctga       57

<210> SEQ ID NO 46
<211> LENGTH: 271
<212> TYPE: DNA
<213> ORGANISM: Artificial Sequence
<220> FEATURE:
<223> OTHER INFORMATION: Synthetic Construct

<400> SEQUENCE: 46
tatgggaagt gcatgtgggt ggtcaggtaa ttgtttgtcc tgaatctgta tttagcagca    60
cagaactatc cactgctgaa attgctacac agctacacgc ctacaacacc accgagaccc   120
ataccaaagc ctgctccgtg ggcaccacag aaacccagaa gacaaatcac aaacgacttc   180
gagggggtac cgagctcccc tacaaccccc ccaagcgagt gcgactcagt gccgtggaca   240
gtgttgacag aggggtctac tctacatctg a                                  271

<210> SEQ ID NO 47
<211> LENGTH: 30
<212> TYPE: DNA
<213> ORGANISM: Artificial Sequence
<220> FEATURE:
<223> OTHER INFORMATION: Synthetic Construct

<400> SEQUENCE: 47
tggttgtgca gtgtacagaa acagacatca                                     30

<210> SEQ ID NO 48
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 48
cacagccact ccgcagggtc cacgctt                                        27

<210> SEQ ID NO 49
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49
```

-continued

```
cacagccact ccgc                                                 14
```

<210> SEQ ID NO 50
<211> LENGTH: 44
<212> TYPE: DNA
<213> ORGANISM: Artificial Sequence
<220> FEATURE:
<223> OTHER INFORMATION: Synthetic Construct

<400> SEQUENCE: 50

```
agggtccacg cacgatcgca cctgtcgcac ggttggacgc actc                 44
```

<210> SEQ ID NO 51
<211> LENGTH: 52
<212> TYPE: DNA
<213> ORGANISM: Artificial Sequence
<220> FEATURE:
<223> OTHER INFORMATION: Synthetic Construct

<400> SEQUENCE: 51

```
cacaggtagg gcacacaata ttcactgcaa cagtacagca agtcacctac ga        52
```

<210> SEQ ID NO 52
<211> LENGTH: 51
<212> TYPE: DNA
<213> ORGANISM: Artificial Sequence
<220> FEATURE:
<223> OTHER INFORMATION: Synthetic Construct

<400> SEQUENCE: 52

```
aacatcatct acaatggccg atcctgagac tgcttctacc tcaaaccaac c         51
```

<210> SEQ ID NO 53
<211> LENGTH: 25
<212> TYPE: DNA
<213> ORGANISM: Artificial Sequence
<220> FEATURE:
<223> OTHER INFORMATION: Synthetic Construct

<400> SEQUENCE: 53

```
tgcccataag tagttgctgt atggt                                     25
```

<210> SEQ ID NO 54
<211> LENGTH: 20
<212> TYPE: DNA
<213> ORGANISM: Artificial Sequence
<220> FEATURE:
<223> OTHER INFORMATION: Synthetic Construct

<400> SEQUENCE: 54

```
gtacaaatgg ggctgggatg                                           20
```

<210> SEQ ID NO 55
<211> LENGTH: 23
<212> TYPE: DNA
<213> ORGANISM: Artificial Sequence
<220> FEATURE:
<223> OTHER INFORMATION: Synthetic Construct

<400> SEQUENCE: 55

```
cacttgtaac accacagttc gtt                                       23
```

<210> SEQ ID NO 56
<211> LENGTH: 30
<212> TYPE: DNA
<213> ORGANISM: Artificial Sequence
<220> FEATURE:
<223> OTHER INFORMATION: Synthetic Construct

<400> SEQUENCE: 56
tctgaaatat tatctcctgt tcttctctct          30

<210> SEQ ID NO 57
<211> LENGTH: 58
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 57
cacagccact ccgcagggtc cacgcacgat cgcacctggt acaaatgggg ctgggatg          58

<210> SEQ ID NO 58
<211> LENGTH: 64
<212> TYPE: DNA
<213> ORGANISM: Artificial Sequence
<220> FEATURE:
<223> OTHER INFORMATION: Synthetic Construct

<400> SEQUENCE: 58
gagtgcgtcc aaccgtgcga caggtgcgat cgtgcgtgga ccctgtacaa atggggctgg          60
gatg          64

<210> SEQ ID NO 59
<211> LENGTH: 231
<212> TYPE: DNA
<213> ORGANISM: Artificial Sequence
<220> FEATURE:
<223> OTHER INFORMATION: Synthetic Construct

<400> SEQUENCE: 59
cacttgtaac accacagttc gtttatgtgt caacagtaca gcaagtgacc tacgaaccat          60
acagcaacta cttatgggca cagtgaatat tgtgtgccct acctgtgcac aacaataaac          120
atcatctaca atggccgatc ctgaaggtac aaatgggggct gggatggggt gtactggttg          180
gtttgaggta gaagcagtca tagagagaag aacaggagat aatatttcag a          231

<210> SEQ ID NO 60
<211> LENGTH: 63
<212> TYPE: DNA
<213> ORGANISM: Artificial Sequence
<220> FEATURE:
<223> OTHER INFORMATION: Synthetic Construct

<400> SEQUENCE: 60
agcctgagtg cgtccaaccg tgcgacaggt gcgatcgtgc gtggaccctg cggagtggct          60
gtg          63

<210> SEQ ID NO 61
<211> LENGTH: 27
<212> TYPE: DNA
<213> ORGANISM: Artificial Sequence
<220> FEATURE:
<223> OTHER INFORMATION: Synthetic Construct

<400> SEQUENCE: 61
cacagccact ccgcagggtc cacgctt                                        27

<210> SEQ ID NO 62
<211> LENGTH: 5
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 62 gcgga                                                                 5

<210> SEQ ID NO 63
<211> LENGTH: 91
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 88
<223> OTHER INFORMATION: Attached to FAM group

<400> SEQUENCE: 63
ccacgagtgc cagtgcgtcc aacgcgtcga caggtgcgat cgtgatctct cgttatgcgg    60
agtggctgtg atccgcataa cgagagatct t                                   91

<210> SEQ ID NO 64
<211> LENGTH: 12
<212> TYPE: DNA
<213> ORGANISM: Artificial Sequence
<220> FEATURE:
<223> OTHER INFORMATION: Synthetic Construct

<400> SEQUENCE: 64
cagccactcc gc                                                        12

<210> SEQ ID NO 65
<211> LENGTH: 37
<212> TYPE: DNA
<213> ORGANISM: Artificial Sequence
<220> FEATURE:
<223> OTHER INFORMATION: Synthetic Construct

<400> SEQUENCE: 65
ataacgagag atcacgatcg cacctgtcga cgcgttg                             37

<210> SEQ ID NO 66
<211> LENGTH: 89
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 66
gcgtggaccc tgcggagtgg ctgtgatcac tccctccaac cctcccacac ctcccatcct    60
ccctccaccc tgagctacac atctagctc                                      89

<210> SEQ ID NO 67
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 25
<223> OTHER INFORMATION: Attached to BHQ group

<400> SEQUENCE: 67
cacagccact ccgcagggtc cacgc                                         25

<210> SEQ ID NO 68
<211> LENGTH: 42
<212> TYPE: DNA
<213> ORGANISM: Artificial Sequence
<220> FEATURE:
<223> OTHER INFORMATION: Synthetic Construct

<400> SEQUENCE: 68
gagctagatg tgtagctcag ggtggaggga ggatgggagt tt                      42

<210> SEQ ID NO 69
<211> LENGTH: 44
<212> TYPE: DNA
<213> ORGANISM: Artificial Sequence
<220> FEATURE:
<223> OTHER INFORMATION: Synthetic Construct

<400> SEQUENCE: 69
agggtggagg gaggatggga ggtgtgggag ggttggaggg attt                    44

<210> SEQ ID NO 70
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 70
gcgtggaccc tgcggagtgg ctgtgatgca tgcacgatcg cacctgtcgc acgagtcctc   60
ccaacc                                                              66

<210> SEQ ID NO 71
<211> LENGTH: 42
<212> TYPE: DNA
<213> ORGANISM: Artificial Sequence
<220> FEATURE:
<223> OTHER INFORMATION: Synthetic Construct

<400> SEQUENCE: 71
gcatgcacga tcgcacctgt cgcacggttg ggaggactct at                      42

<210> SEQ ID NO 72
<211> LENGTH: 85
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1

<223> OTHER INFORMATION: Attached to FAM group

<400> SEQUENCE: 72
gcgtggaccc tgcggagtgg ctgtgatgcc gagagtcctc ccaaccgtct gtagcgagac     60
atatgtcgca cgtctcgcat cccac     85

<210> SEQ ID NO 73
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 38
<223> OTHER INFORMATION: Attached to 3phos group

<400> SEQUENCE: 73
gtcgcacgtg ggaacagacg gttgggagga ctctcggc     38

<210> SEQ ID NO 74
<211> LENGTH: 63
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 63
<223> OTHER INFORMATION: Attached to BHQ group

<400> SEQUENCE: 74
agcctgagtg cgtccaaccg tgcgacaggt gcgatcgtgc gtggaccctg cggagtggct     60
gtg     63

<210> SEQ ID NO 75
<211> LENGTH: 51
<212> TYPE: DNA
<213> ORGANISM: Artificial Sequence
<220> FEATURE:
<223> OTHER INFORMATION: Synthetic Construct

<400> SEQUENCE: 75
cgagaagggt ccacgcacga tcgcacctgt cgcacggttg gacgcactcg a     51

<210> SEQ ID NO 76
<211> LENGTH: 114
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 114
<223> OTHER INFORMATION: Attached to FAM group

<400> SEQUENCE: 76
gagagtgcgt ccaaccgtgc gacaggtgcg atcgtgcgtg gacccttctc gtttttgagt     60
gcgtccaacc gtgcgacagg tgcgatcgtg cgtggaccct gcggagtggc tgtc     114

<210> SEQ ID NO 77
<211> LENGTH: 31
<212> TYPE: DNA
<213> ORGANISM: Artificial Sequence
<220> FEATURE:
<223> OTHER INFORMATION: Synthetic Construct -continued

```
<220> FEATURE:
<221> NAME/KEY: misc_feature
<222> LOCATION: 1
<223> OTHER INFORMATION: Attached to BHQ group

<400> SEQUENCE: 77
gacagccact ccgcagggtc cacgcacgtt t                              31

<210> SEQ ID NO 78
<211> LENGTH: 24
<212> TYPE: DNA
<213> ORGANISM: Artificial Sequence
<220> FEATURE:
<223> OTHER INFORMATION: Synthetic Construct

<400> SEQUENCE: 78
acgatcgcac ctgtcgcacg tttt                                      24

<210> SEQ ID NO 79
<211> LENGTH: 12
<212> TYPE: DNA
<213> ORGANISM: Artificial Sequence
<220> FEATURE:
<223> OTHER INFORMATION: Synthetic Construct

<400> SEQUENCE: 79
cagccactcc gc                                                   12

<210> SEQ ID NO 80
<211> LENGTH: 12
<212> TYPE: DNA
<213> ORGANISM: Artificial Sequence
<220> FEATURE:
<223> OTHER INFORMATION: Synthetic Construct

<400> SEQUENCE: 80
gtccacgcac ga                                                   12

<210> SEQ ID NO 81
<211> LENGTH: 32
<212> TYPE: DNA
<213> ORGANISM: Artificial Sequence
<220> FEATURE:
<223> OTHER INFORMATION: Synthetic Construct

<400> SEQUENCE: 81
gcacctgtcg cacggttgga cgcactcagg ct                             32

<210> SEQ ID NO 82
<211> LENGTH: 57
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 57
<223> OTHER INFORMATION: Attached to BHQ group

<400> SEQUENCE: 82
gagtgcgtcc aaccgtgcga caggtgcgat cgtgcgtgga ccctcccacc caccctc   57

<210> SEQ ID NO 83
<211> LENGTH: 30
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: 1
<223> OTHER INFORMATION: Attached to FAM group

<400> SEQUENCE: 83
gagggtgggt gggagggtcc acgcacgtaa                                    30

<210> SEQ ID NO 84
<211> LENGTH: 13
<212> TYPE: DNA
<213> ORGANISM: Artificial Sequence
<220> FEATURE:
<223> OTHER INFORMATION: Synthetic Construct

<400> SEQUENCE: 84
gggagggtgg gtg                                                      13

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
cacagccact ccgc                                                     14

<210> SEQ ID NO 86
<211> LENGTH: 400
<212> TYPE: DNA
<213> ORGANISM: Human papillomavirus

<400> SEQUENCE: 86
aatatgggaa cacaggtacg tgggaagtac attttgggaa taatgtaatt gattgtaatg    60
actctatgtg cagtaccagt gacgacacgg tatccgctac tcagcttgtt aaacagctac   120
agcacacccc ctcaccgtat tccagcaccg tgtccgtggg caccgcaaag acctacggcc   180
agacgtcggc tgctacacga cctggacact gtggactcgc ggagaagcag cattgtggac   240
ctgtcaaccc acttctcggt gcagctacac ctacaggcaa caacaaaaga cggaaactct   300
gtagtggtaa cactacgcct ataatacatt taaaaggtga cagaaacagt ttaaaatgtt   360
tacggtacag attgcgaaaa catagcgacc actatagaga                        400
```